United States Patent
Chilla et al.

(10) Patent No.: US 11,604,178 B2
(45) Date of Patent: Mar. 14, 2023

(54) CARBON MONOXIDE WARNING SYSTEM AND DEVICES

(71) Applicant: QUALCOMM Incorporated, San Diego, CA (US)

(72) Inventors: Rajashekar Chilla, San Diego, CA (US); Abhi Umeshkumar Shah, San Diego, CA (US); Sanjeet Pandit, San Diego, CA (US); Lakshmi Bhavani Garimella Srivenkata, San Diego, CA (US); Michael Franco Taveira, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 3 days.

(21) Appl. No.: 17/324,825

(22) Filed: May 19, 2021

(65) Prior Publication Data

US 2021/0349066 A1    Nov. 11, 2021

Related U.S. Application Data

(63) Continuation-in-part of application No. 17/246,165, filed on Apr. 30, 2021.
(Continued)

(51) Int. Cl.
*G01N 33/00* (2006.01)
*G08B 25/00* (2006.01)
(Continued)

(52) U.S. Cl.
CPC .......... *G01N 33/004* (2013.01); *G08B 21/14* (2013.01); *G08B 25/007* (2013.01); *G08B 25/10* (2013.01)

(58) Field of Classification Search
CPC ...... G08B 21/14; G08B 25/007; G08B 25/10; G08B 29/188; G08B 17/005; G08B 17/117; G01N 33/004; Y02A 50/20
See application file for complete search history.

(56) References Cited

U.S. PATENT DOCUMENTS

| | | | |
|---|---|---|---|
| 2008/0016253 A1* | 1/2008 | Boctor | G06F 8/34 709/250 |
| 2010/0238019 A1* | 9/2010 | Richman | G08B 25/08 340/521 |

(Continued)

FOREIGN PATENT DOCUMENTS

CN    210221944 U    3/2020

OTHER PUBLICATIONS

Andre Z., et al., "Smart Environment—Early Wildfire Detection using IoT", Department Of Electrical And Information Technology Faculty Of Engineering, LTH, Lund University, Jun. 26, 2020 (Jun. 26, 2020), XP055829568, 57 Pages, Retrieved from the Internet: URL: https://lup.lub.lu.se/student-papers/record/9022505/file/9022959. pdf. [Retrieved on Aug. 2, 2021], Sections 1.3, 2.6.2, 2.6.3, 2.8, 4-6.

(Continued)

*Primary Examiner* — Ojiako K Nwugo
(74) *Attorney, Agent, or Firm* — The Marbury Law Group, PLLC

(57) ABSTRACT

Various embodiments include a carbon monoxide (CO) detection device and methods for operating a FDS or CO detection device to detect carbon monoxide and communicate information regarding CO detection events to a remote server via communication network. Various embodiments include receiving information from one or more CO sensors configured to detect CO, determining whether the information from the one or more CO sensors satisfies one or more threshold criteria indicative of fire event or CO detection, generating a CO warning message comprising a fire and/or (Continued)

CO alarm object in response to determining that the information received from the one or more CO sensors satisfy one or more threshold criteria indicative of CO detection, and sending the generated CO warning message to a remote server via a communication network.

31 Claims, 23 Drawing Sheets

Related U.S. Application Data

(60) Provisional application No. 63/028,397, filed on May 21, 2020, provisional application No. 63/022,391, filed on May 8, 2020.

(51) Int. Cl.
*G08B 25/10* (2006.01)
*G08B 21/14* (2006.01)

(56) References Cited

U.S. PATENT DOCUMENTS

| | | | |
|---|---|---|---|
| 2014/0270383 A1* | 9/2014 | Pederson | G08G 1/207 382/104 |
| 2016/0210844 A1* | 7/2016 | Kim | G08B 25/10 |
| 2017/0153790 A1* | 6/2017 | Mohanam | H04W 4/90 |
| 2017/0249831 A1* | 8/2017 | Wengrovitz | H04W 12/069 |
| 2018/0089988 A1* | 3/2018 | Schwarzkopf | G06Q 50/08 |
| 2018/0262985 A1 | 9/2018 | Kates | |
| 2019/0287363 A1 | 9/2019 | Balaji et al. | |
| 2019/0318599 A1 | 10/2019 | Ryder | |
| 2020/0242916 A1* | 7/2020 | Krstanovic | G08B 21/0453 |
| 2020/0348446 A1 | 11/2020 | Tremsin | |
| 2021/0349066 A1* | 11/2021 | Chilla | G08B 17/117 |
| 2021/0350691 A1 | 11/2021 | Shah et al. | |
| 2021/0366267 A1* | 11/2021 | Connell, II | H04W 4/90 |
| 2021/0368309 A1* | 11/2021 | Lupper | G08B 25/10 |

OTHER PUBLICATIONS

Huawei Technologies Co, "IoT Device Management", Guide Development, Aug. 28, 2019 (Aug. 28, 2019), XP055829898, 293 Pages, Retrieved from the Internet: URL: https://support.huaweicloud.com/intl/en-us/devg-IoT/IoT-devg.pdf. [Retrieved on Aug. 3, 2021] From p. 78 to p. 125, Point 1.6.1 from p. 207 to p. 209, and p. 239, 4.1.3 Appendix 1 LWM2M from p. 257 (in particular point 4.1.3.5 Resource Formatat pp. 260 and 261).

International Search Report and Written Opinion—PCT/US2021/033496—ISA/EPO—dated Sep. 3, 2021 16 pages.

Mathew A.A., et al., "Augmenting IoT-Based Systems with Intelligence", 2018 IEEE International Conference on Electronics, Computing and Communication Technologies (Conecct), IEEE, Mar. 16, 2018 (Mar. 16, 2018), pp. 1-6, XP033415545, DOI: 10.1109/CONECCT.2018.8482372, [Retrieved on Oct. 4, 2018] Abstract, from p. 4, Point A. Implementation, from right column—LwM2M—to p. 5, left column, line 6, p. 5, left column, point B. Building use case.

Anonymous: "OMA LWM2M Object Editor CO Detector", Jan. 19, 2021 (Jan. 19, 2021), XP055829964, 3 pages, Retrieved from the Internet: URL: https://devtoolkit.openmobilealliance.org/OEditor/LWMOView?url=https://raw.githubusercontent.com/OpenMobileAlliance/lwm2m-registry/prod/502.xml. [Retrieved on Aug. 3, 2021] the whole document (3 pages).

Anonymous: "OMA LWM2M Object Editor Fire Alarm", Jan. 19, 2021 (Jan. 19, 2021), XP055829848, 5 pages, Retrieved from the Internet: URL: https://devtoolkit.openmobilealliance.org/OEditor/LWMOView?url=https://raw.githubusercontent.com/OpenMobileAlliance/lwm2mregistryjprod/503.xml. [Retrieved on Aug. 3, 2021] the whole document (5 pages).

Benzekri W., et al., "Early Forest Fire Detection System using Wireless Sensor Network and Deep Learning", International Journal of Advanced Computer Science and Applications (IJACSA), vol. 11, No. 5, 2020, pp. 496-503.

\* cited by examiner

Fire Alarm Object

This is an alarm that should be raised if the meter detects fire, based on the values reported from Temperature, Humidity, Smoke (CO2 and CO) object values.

Object definition

| Name | Object ID | Object Version: | LWM2M Version |
|---|---|---|---|
| Fire Alarm | xxxx | | Mandatory |
| Object URN | | Instances | Optional |
| urn:oma:lwm2m:ext:xxxx | | Multiple | |

Resource Definitions

| ID | Name | Operations | Instances | Mandatory | Type | Range or Enumeration | Units | Description |
|---|---|---|---|---|---|---|---|---|
| 1 | Temperature Unit | RW | Single | Mandatory | Boolean | | | Temperature Unit set 0 = °C (Celsius) 1 = °F (Fahrenheit) |
| 2 | Ambient Temperature | RW | Single | Optional | Float | (-70) °C to 150 °C or (-94) °F to 302 °F | °C or °F | Temperature received from web for the area |
| 3 | Temperature Value | R | Single | Mandatory | Float | (-70) °C to 150 °C or (-94) °F to 302 °F | °C or °F | Last or Current Measured Value from the Sensor 0 = Sensor not integrated |
| 4 | Minimum Measured Temperature Value | R | Single | Optional | Float | (-70) °C to 150 °C or (-94) °F to 302 °F | °C or °F | The minimum Temperature value measured by the sensor since power ON or reset |
| 5 | Maximum Measured Temperature Value | R | Single | Optional | Float | (-70) °C to 150 °C or (-94) °F to 302 °F | °C or °F | The maximum Temperature value measured by the sensor since power ON or reset |
| 6 | Min Temperature Range Value | R | Single | Optional | Float | (-70) °C or (-94) °F | °C or °F | The minimum value that can be measured by the sensor |
| 7 | Max Temperature Range Value | R | Single | Optional | Float | 150 °C or 302 °F | °C or °F | The maximum value that can be measured by the sensor |
| 8 | Temperature Accuracy | R | Single | Optional | String | 1 °C to 5 °C or 1 °F to 5 °F | °C or °F | Indicate range of the accuracy for the temperature Sensor. |
| 9 | Temperature Threshold | RW | Single | Optional | Float | (-70) °C to 150 °C or (-94) °F to 302 °F | °C or °F | Indicate the maximum threshold for the temperature. |
| 10 | Temperature Sensor State | R | Single | Optional | Boolean | | | Temperature Sensor State 0 = Faulty 1 = Working correctly |
| 11 | Reset | E | Single | Optional | | | | Reset the "Temperature" related parameters to default |
| 12 | Alarm Loudness (Temperature) | R | Single | Optional | Float | | dB | Indicates the loudness of alarm due to temperature |

Fire Alarm Object (Contd.)

500b

| | | | | | | |
|---|---|---|---|---|---|---|
| | | | | | Humidity | |
| 13 | Ambient Humidity | RW | Single | Optional | Integer | % | Humidity value received from web for the area |
| 14 | Humidity Value | R | Single | Mandatory | Integer | 0-100 | % | Last or Current Measured Humidity Value from the Sensor<br>0 = Sensor not integrated |
| 15 | Minimum Measured Humidity Value | R | Single | Optional | Integer | 0-100 | % | The minimum Humidity value measured by the sensor since power ON or reset |
| 16 | Maximum Measured Humidity Value | R | Single | Optional | Integer | 0-100 | % | The maximum Humidity value measured by the sensor since power ON or reset |
| 17 | Humidity Threshold | RW | Single | Optional | Integer | 0-100 | % | Indicate the threshold for the Humidity. |
| 18 | Humidity Sensor State | R | Single | Optional | Boolean | | | Humidity Sensor State<br>0 = Faulty<br>1 = Working correctly |
| 19 | Reset | E | Single | Optional | | | | Reset the "Humidity" related parameters to default. |
| 20 | Alarm Loudness (Humidity) | E | Single | Optional | Float | | dB | Indicates the loudness of alarm due to Humidity |
| | | | | | Smoke | | |
| 21 | CO2 Detected | R | Single | Mandatory | Boolean | | | 0 = CO2 NOT detected<br>1 = CO2 Detected |
| 22 | Ambient CO2 Value | RW | Single | Optional | Integer | 0-100 | % | CO2 value received from web for the area |
| 23 | CO2 Value | R | Single | Mandatory | Float | 0-100 | % | Last or Current Measured CO2 Value from the Sensor<br>0 = Sensor not integrated |
| 24 | Minimum Measured CO2 Value | R | Single | Optional | Float | 0-100 | % | The minimum CO2 value measured by the sensor since power ON or reset |
| 25 | Maximum Measured CO2 Value | R | Single | Optional | Float | 0-100 | % | The maximum CO2 value measured by the sensor since power ON or reset |
| 26 | Upper CO2 Threshold | RW | Single | Optional | Float | 0-100 | % | Indicate the Upper threshold for the CO2 Value. |
| 27 | Smoke Sensor State | R | Single | Optional | Boolean | | | Smoke Sensor State<br>0 = Faulty<br>1 = Working correctly |
| 28 | Reset | E | Single | Optional | | | | Reset the "Smoke" related parameters to default. |
| 29 | Alarm Loudness (Smoke) | R | Single | Optional | Float | | dB | Indicates the loudness of alarm due to Smoke |

FIG. 5B

Fire Alarm Object                                                          500c

Description

This is an alarm that should be raised if the sensor(s) detect fire, based on the values reported from Temperature, Humidity, Smoke (CO2).

Object definition

| Name | Object ID | Object Version | LwMWM Version |
|---|---|---|---|
| Fire Alarm | 503 | 1.0 | 1.0 |
| Object URN | | Instances | Mandatory |
| urn:oma:lwm2m:oma:503 | | Multiple | Optional |

Resource Definitions

| ID | Name | Operations | Instances | Mandatory | Type | Range or Enumeration | Units | Description |
|---|---|---|---|---|---|---|---|---|
| 0 | Temperature Sensor Location Tag | RW | Single | Optional | String | | | Verbose identification of the location of the Temperature sensor location |
| 1 | Temperature Unit | RW | Single | Mandatory | Integer | | | Temperature Units: 0 = Celsius, 1 = Fahrenheit, 2 = Kelvin. All temperature values are represented in this unit. |
| 2 | Ambient Temperature | RW | Single | Optional | Float | | | Temperature for the area. |
| 3 | Temperature Value | R | Single | Mandatory | Float | | | Last or Current Measured Temperature Value from the Sensor. The value 65534 indicates that the Sensor data is not available. |
| 4 | Minimum Measured Temperature Value | R | Single | Optional | Float | | | The minimum Temperature value measured by the sensor since power ON or reset. |
| 5 | Maximum Measured Temperature Value | R | Single | Optional | Float | | | The maximum Temperature value measured by the sensor since power ON or reset. |
| 6 | Min Temperature Range Value | RW | Single | Optional | Float | | | The minimum temperature value that can be measured by the sensor. |
| 7 | Max Temperature Range Value | RW | Single | Optional | Float | | | The maximum temperature value that can be measured by the sensor. |
| 8 | Lower Temperature Accuracy | RW | Single | Optional | Float | | | Indicates the lower end of the accuracy range for the temperature sensor. |
| 9 | Upper Temperature Accuracy | RW | Single | Optional | Float | | | Indicates the upper end of the accuracy range for the temperature sensor. |
| 10 | Temperature Threshold | RW | Single | Optional | Float | | | Indicates the maximum threshold for the temperature. |
| 11 | Temperature Sensor Error | R | Single | Optional | Boolean | | | Temperature Sensor Error: 0 = false (Working correctly), 1 = true (Faulty). |
| 12 | Reset Temperature | E | Single | Optional | | | | Reset the "Temperature" related parameters to default. |
| 13 | Temperature Alarm Loudness | RW | Single | Optional | Float | | dB | Indicates the loudness of temperature alarm. |

FIG. 5C

Fire Alarm Object (Contd.)                                    500d

| 14 | Humidity Sensor Location Tag | RW | Single | Optional | String | | | Verbose identification of the location of the Humidity sensor. |
|---|---|---|---|---|---|---|---|---|
| 15 | Ambient Relative Humidity | RW | Single | Optional | Float | 0.0..100.0 | %RH | Relative humidity for the area. |
| 16 | Humidity Value | R | Single | Mandatory | Float | 0.0..100.0 | /100 | Last or Current Measured Humidity Value from the Sensor. The value 0 indicates that the Sensor data is not available. |
| 17 | Minimum Measured Humidity Value | R | Single | Optional | Float | 0.0..100.0 | /100 | The minimum Humidity value measured by the sensor since power ON or reset. |
| 18 | Maximum Measured Humidity Value | R | Single | Optional | Float | 0.0..100.0 | /100 | The maximum Humidity value measured by the sensor since power ON or reset. |
| 19 | Humidity Accuracy | RW | Single | Optional | Float | 0.0..100.0 | /100 | Indicate the accuracy for the Humidity Sensor. |
| 20 | Humidity Threshold | RW | Single | Optional | Float | 0.0..100.0 | /100 | Indicate the threshold for the Humidity. |
| 21 | Humidity Sensor Error | R | Single | Optional | Boolean | | | Humidity Sensor Error: 0 = false (Working correctly), 1 = true (Faulty) |
| 22 | Reset Humidity | E | Single | Optional | | | | Reset the "Humidity" related parameters to default. |
| 23 | Humidity Alarm Loudness | RW | Single | Optional | Float | | dB | Indicates the loudness of the Humidity alarm. |
| 24 | Smoke Sensor Location Tag | RW | Single | Optional | String | | | Verbose identification of the location of the Smoke sensor. |
| 25 | CO2 Alarm State | R | Single | Mandatory | Boolean | | | 0 = False (CO2 alarm threshold not exceeded), 1 = True (CO2 alarm threshold exceeded). |
| 26 | Ambient CO2 Value | R | Single | Optional | Float | | ppm | CO2 value for the area. |
| 27 | CO2 Value | R | Single | Mandatory | Float | | ppm | Last or Current Measured CO2 Value from the sensor. The value 0 indicates that the Sensor data is not available. |
| 28 | Minimum Measured CO2 Value | R | Single | Optional | Float | | ppm | The minimum CO2 value measured by the sensor since power ON or reset. |
| 29 | Maximum Measured CO2 Value | R | Single | Optional | Float | | ppm | The maximum CO2 value measured by the sensor since power ON or reset. |
| 30 | CO2 Threshold | RW | Single | Optional | Float | | ppm | Indicate the alarm threshold for the CO2. |
| 31 | Smoke Sensor Error | R | Single | Optional | Boolean | | | Smoke Sensor Error: 0 = false (Working correctly), 1 = true (Faulty) |
| 32 | Reset Smoke Detection | E | Single | Optional | | | | Reset the "Smoke" related parameters to default. |
| 33 | Smoke Alarm Loudness | R | Single | Optional | Float | | dB | Indicates the loudness of smoke alarm |
| 6044 | Battery Percentage | R | Single | Optional | Float | 0.00..100.00 | | Current remaining battery level. |
| 5514 | Latitude | R | Single | Optional | String | | | The decimal notation of latitude, e.g. -43.5723 (World Geodetic System 1984). |
| 5515 | Longitude | R | Single | Optional | String | | | The decimal notation of longitude, e.g. 153.21760 (World Geodetic System 1984). |
| 6039 | Altitude | R | Single | Optional | Float | | m | Altitude above sea level in meters. |

FIG. 5D

CO Detector Object

This is an alarm that should be raised if the sensor detects higher CO level

Object definition

| Name | CO Detector | Object Version | | LWM2M Version | |
|---|---|---|---|---|---|
| Object ID | xxxx | Instances | Multiple | Mandatory | |
| Object URN | urn:oma:lwm2m:ext:xxxx | | | Optional | |

Resource Definitions

| ID | Name | Operations | Instances | Mandatory | Type | Range or Enumeration | Units | Description |
|---|---|---|---|---|---|---|---|---|
| 0 | CO Sensor Location Tag | RW | Single | Optional | String | | | To verbose identification of the location of the CO sensor location |
| 1 | CO Detected | R | Single | Mandatory | Boolean | | | 0 = CO NOT detected<br>1 = CO Detected |
| 2 | Ambient CO Value | RW | Single | Optional | Integer | 0-600 | ppm | CO value received from web for the area |
| 3 | CO Value | R | Single | Mandatory | Float | 0-600 | ppm | Last or Current Measured CO Value from the Sensor |
| 4 | Min CO Range Value | R | Single | Optional | Float | 0-600 | ppm | The minimum value that can be measured by the sensor |
| 5 | Max CO Range Value | R | Single | Optional | Float | 0-600 | ppm | The maximum value that can be measured by the sensor |
| 6 | CO Detection Accuracy | R | Single | Optional | Float | 0-600 | ppm | Indicate range of the accuracy for the temerature Sensor. |
| 7 | Minimum Measured CO Value | R | Single | Optional | Float | 0-600 | ppm | The minimum CO value measured by the sensor since power ON or reset |
| 8 | Maximum Measured CO Value | R | Single | Optional | Float | 0-600 | ppm | The maximum CO value measured by the sensor since power ON or reset |
| 9 | Upper CO Threshold | RW | Single | Optional | Float | | ppm | Indicate the Upper threshold for the CO Value. |
| 10 | Reset | E | Single | Optional | | | | Reset the "CO" related parameters to default |
| 11 | Alarm Loudness (CO) | R | Single | Optional | Float | | dB | Indicates the loudness of alarm due to CO |
| 12 | Latitude | R | Single | Optional | Float | | deg | The decimal notation of latitude, e.g., -43.5723 [World Geodetic System 1984]. |
| 13 | Longitude | R | Single | Optional | Float | | deg | The decimal notation of longitude, e.g., 153.21760 [World Geodetic System 1984]. |
| 14 | Altitude | R | Single | Optional | Float | | m | The decimal notation of altitude in meters above sea level. |

CO Detector Object

500f

Description

This is an alarm that should be raised if the sensor detects a higher than threshold CO level.

Object definition

| Name | Object ID | Object Version | LWM2M Version |
|---|---|---|---|
| CO Detector | 502 | 1.0 | 1.0 |
| Object URN | | Instances | Mandatory |
| urn:oma:lwm2m:oma:502 | | Multiple | Optional |

Resource Definitions

| ID | Name | Operations | Instances | Mandatory | Type | Range or Enumeration | Units | Description |
|---|---|---|---|---|---|---|---|---|
| 0 | CO Sensor Location Tag | RW | Single | Optional | String | | | Verbose identification of the location of the CO sensor. |
| 1 | CO Detected | R | Single | Mandatory | Boolean | | | 0 = false (CO NOT detected), 1 = true (CO Detected) |
| 2 | Ambient CO Value | RW | Single | Optional | Float | 0..12800 | ppm | CO value (in ppm) received for the area. |
| 3 | CO Value | R | Single | Mandatory | Float | 0..12800 | ppm | Last or Current Measured CO Value (in ppm) from the Sensor. |
| 4 | Min CO Range Value | R | Single | Optional | Float | 0..12800 | ppm | The minimum value that can be measured by the sensor (in ppm). |
| 5 | Max CO Range Value | R | Single | Optional | Float | 0..12800 | ppm | The maximum value that can be measured by the sensor. |
| 6 | CO Detection Accuracy | R | Single | Optional | Float | 0..12800 | ppm | Indicate range of the accuracy for the temperature Sensor. |
| 7 | Minimum Measured CO Value | R | Single | Optional | Float | 0..12800 | ppm | The minimum CO value (in ppm) measured by the sensor since power ON or reset. |
| 8 | Maximum Measured CO Value | R | Single | Optional | Float | 0..12800 | ppm | The maximum CO value measured (in ppm) by the sensor since power ON or reset |
| 9 | Upper CO Threshold | RW | Single | Optional | Float | 0..12800 | ppm | Indicate the Upper threshold for the CO Value (in ppm). |
| 10 | Reset | E | Single | Optional | | | | Reset the "CO" object related parameters to default |
| 6048 | Alarm loudness | R | Single | Optional | Float | | dB | Indicate the loudness of the alarm. |
| 5514 | Latitude | R | Single | Optional | String | | | The decimal notation of latitude, e.g. -43.5723 (World Geodetic System 1984). |
| 5515 | Longitude | R | Single | Optional | String | | | The decimal notation of longitude, e.g. 153.21760 (World Geodetic System 1984). |
| 6039 | Altitude | R | Single | Optional | Float | | m | Altitude above sea level in meters. |
| 6044 | Battery Percentage | R | Single | Optional | Float | 0.00..100.00 | | Current remaining battery level. |

FIG. 5F

CARBON MONOXIDE WARNING SYSTEM AND DEVICES

RELATED APPLICATIONS

This application is a continuation-in-part of U.S. patent application Ser. No. 17/246,165 entitled "Fire Warning System and Devices" filed Apr. 30, 2021, which claims the benefit of priority to U.S. Provisional Application No. 63/022,391 entitled "Fire Warning System and Devices" filed May 8, 2020, and this application claims the benefit of priority to U.S. Provisional Application No. 63/028,397 entitled "Carbon Monoxide Warning System and Devices" filed May 21, 2020, the entire contents of all three of which are hereby incorporated by reference for all purposes.

BACKGROUND

Fires can rapidly inflict destruction across a wide area, affecting forests and wildlife as well as posing a threat to human life and property. Early and accurate detection of fires is a benefit to all. However, current systems for machine sensing of fires are limited. Conventional sensors rely on optical (i.e., visible light) cameras to detect fires, which require a fire to reach a minimum size or intensity to be detected, by which point the fire may have begun to grow beyond the possibility of rapid control. Conventional sensors also do not provide an accurate co-ordinate location of the detected fire. Further, communication from the sensor to a wireless communication network may be highly dependent on atmospheric conditions, and may be limited to line-of-sight communications.

Carbon monoxide (CO) is a colorless, odorless gas produced as a by-product of incomplete combustion. Automobile exhaust and appliances such as gas fires, boilers, central heating systems, water heaters, cookers, and open fires that use gas, oil, coal and wood are all possible sources of carbon monoxide. Because carbon monoxide binds preferentially to hemoglobin over oxygen, carbon monoxide poses an extremely dangerous health risk to humans and animals. In addition to potentially fatal oxygen deprivation, carbon monoxide poisoning may have longer term effects including memory problems, impaired coordination, and cardiac damage. Therefore, detecting and reporting carbon monoxide is vital to health and safety.

SUMMARY

Various aspects include methods and FDS or CO detection devices suitable for use in a variety of settings. Various aspects may include receiving information from one or more CO sensors configured to detect CO, determining whether the information received from the one or more CO sensors satisfies one or more threshold criteria indicative of fire and/or CO detection, generating a fire and/or CO warning message including a fire and/or CO alarm object in response to determining that the information received from the one or more CO sensors satisfy one or more threshold criteria indicative of fire and/or CO detection, and sending the generated fire and/or CO warning message to a remote server via a communication network.

In some aspects, the fire and/or CO alarm object may include a Lightweight Machine-to-Machine (LwM2M) object. In some aspects, the fire and/or CO alarm object may be configured to indicate one or more resource definition identifiers (IDs). In some aspects, the fire and/or CO alarm object may be configured to indicate a permissible operation for a resource of the fire and/or CO alarm object. In some aspects, the fire and/or CO alarm object may be configured to indicate a permitted number of instances of a resource of the fire and/or CO alarm object. In some aspects, the fire and/or CO alarm object may be configured to indicate whether an operation related to a resource of the fire and/or CO alarm object is mandatory or optional. In some aspects, the fire and/or CO alarm object may be configured to indicate a data type of a resource of the fire and/or CO alarm object. In some aspects, the fire and/or CO alarm object may be configured to indicate a permitted range for or enumeration of information of a resource of the fire and/or CO alarm object. In some aspects, the fire and/or CO alarm object may be configured to indicate permissible units for information represented in a resource of the fire and/or CO alarm object. In some aspects, the fire and/or CO alarm object may be configured to include a description of one or more values associated with a resource of the fire and/or CO alarm object.

In some aspects, sending the generated fire and/or CO warning message to a remote server via a communication network may include activating a transceiver, and sending the generated fire and/or CO warning message to the remote server via the communication network using the activated transceiver. In some aspects, the communication network may include a wireless communication network.

Further aspects include a FDS or CO detection device having a processor configured with processor-executable instructions to perform operations of any of the methods summarized above. Further aspects include a system on chip, system in package or similar processing and communication components for use in a FDS or CO detection device and configured to perform operations of any of the methods summarized above. Various aspects include a FDS or CO detection device having means for performing functions of any of the methods summarized above. Various aspects include a non-transitory processor-readable medium having stored thereon processor-executable instructions configured to cause a processor of a FDS or CO detection device to perform operations of any of the methods summarized above.

BRIEF DESCRIPTION OF THE DRAWINGS

The accompanying drawings, which are incorporated herein and constitute part of this specification, illustrate exemplary embodiments of the claims, and together with the general description given above and the detailed description given below, serve to explain the features of the claims.

FIGS. 5A-5D illustrate aspects of example fire alarm objects according to various embodiments.

FIG. 5E illustrates aspects of a CO alarm object according to various embodiments.

FIG. 5F illustrates aspects of a CO alarm object according to various embodiments.

DETAILED DESCRIPTION

Figure 1A:
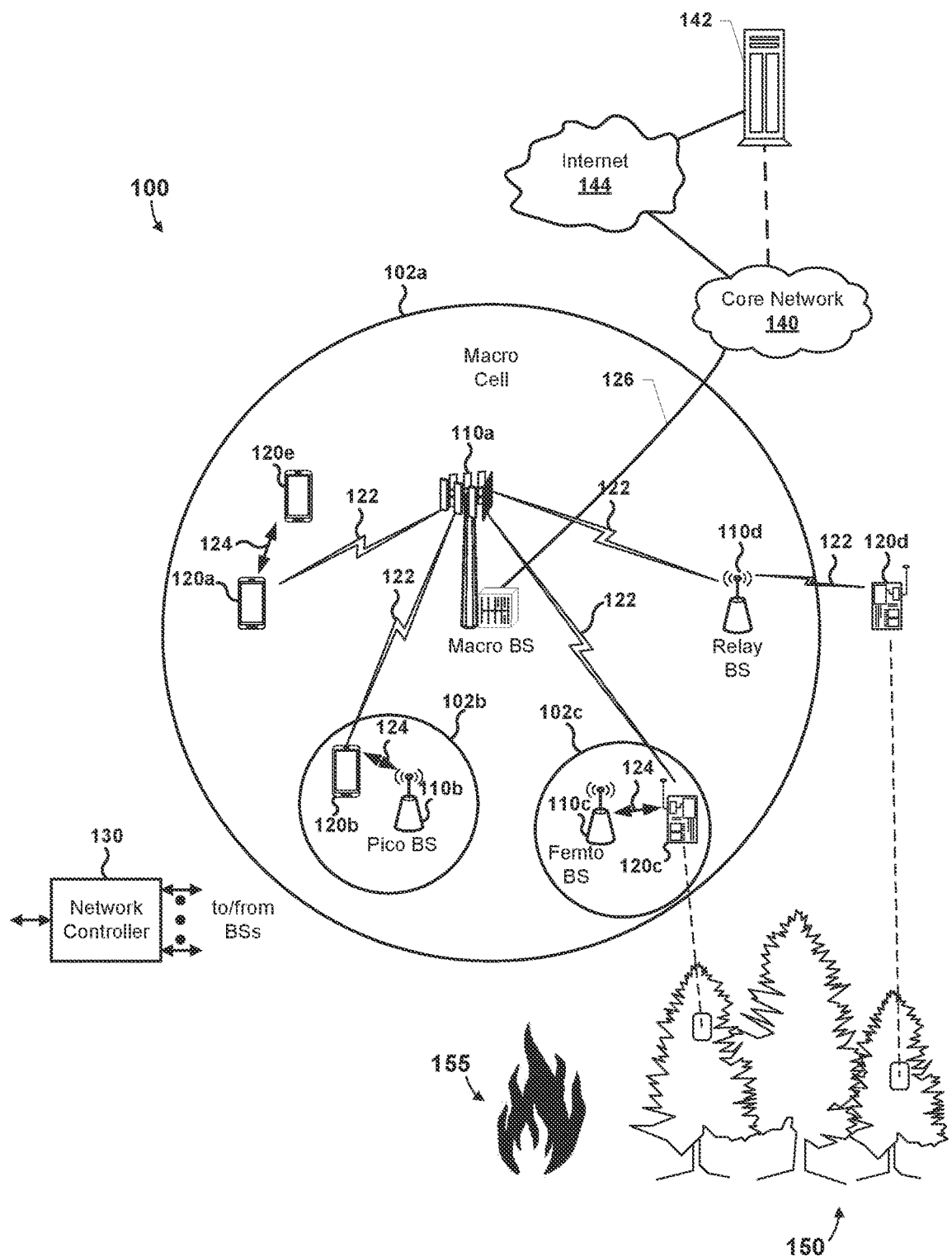
FIGS. 1A and 1B are system block diagrams illustrating example wireless networks suitable for use with various embodiments.

Various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims.

Various embodiments include FDS or CO detection devices, components for use in FDS or CO detection devices and methods of operating FDS or CO detection devices and components to facilitate the detection and tracking of fire events and detection of carbon monoxide, including communicating relevant sensor data and other information regarding potential or actual fire events and/or CO detections to a centralized fire detection and management and/or CO response system and/or portable devices (such as a user device like a mobile communication device, etc.). Various embodiments enable early detection, mapping and response to potential fire conditions and fire events as well as potentially dangerous levels of carbon monoxide to support rapid early responses that may aid in fire containment or suppression and/or response to high CO levels.

The term "fire detection system (FDS) device" is used herein to refer to any of a variety of devices including a processor and transceiver for communicating with other devices or a network. The term "FDS or CO detection chipset" is used herein to refer to a processor and communication chip assembly, system-on-chip, or system-in-package that is configured to be implemented in a FDS or CO detection device and includes a processor and communication circuitry configured to perform operations of various embodiments. For example, a FDS or CO detection device may include at least one FDS or CO detection chipset as well as a power source, sensors, interfaces for connecting to sensors, a wireless antenna, and other components. For ease of description, examples of FDS or CO detection devices are described as communicating via radio frequency (RF) wireless communication links, but FDS or CO detection devices may communicate via wired or wireless communication links with another device (or user), for example, as a participant in a wireless communication network, such as a cellular wireless communication network, a wide area network, any wireless communication network supporting the Internet of Things (IoT), a wireless mesh network of multiple FDS or CO detection devices (or other devices such as smoke detectors), or any other suitable communication system. Such communications may include communications with another wireless device, a base station (including a cellular wireless communication network base station and an IoT base station), an access point (including an IoT access point), or other wireless devices.

FDS or CO detection devices may be capable of transmitting and receiving RF signals according to any of the Institute of Electrical and Electronics Engineers (IEEE) 16.11 standards, or any of the IEEE 802.11 standards, the Bluetooth standard, code division multiple access (CDMA), frequency division multiple access (FDMA), time division multiple access (TDMA), time division-synchronous code division multiple access (TD-SCDMA), Global System for Mobile communications (GSM), GSM/General Packet Radio Service (GPRS), Enhanced Data GSM Environment (EDGE), Terrestrial Trunked Radio (TETRA), Wideband-CDMA (W-CDMA), CDMA2000, Worldwide Interoperability for Microwave Access (WiMAX), Evolution Data Optimized (EV-DO), 1×EV-DO, EV-DO Rev A, EV-DO Rev B, High Speed Packet Access (HSPA), High Speed Downlink Packet Access (HSDPA), High Speed Uplink Packet Access (HSUPA), Evolved High Speed Packet Access (HSPA+), Long Term Evolution (LTE), AMPS, or other signals that are used to communicate within a wireless, cellular, or IoT network, such as an IEEE 802.15.4 protocol (for example, Thread, ZigBee, and Z-Wave), 6LoWPAN, Bluetooth Low Energy (BLE), LTE Machine-Type Communication (LTE MTC), Narrow Band LTE (NB-LTE), Cellular IoT (CIoT), Narrow Band IoT (NB-IoT), BT Smart, Wi-Fi, LTE-U, LTE-Direct, and MuLTEfire, as well as relatively extended-range wide area physical layer interfaces (PHYs) such as Random Phase Multiple Access (RPMA), Ultra Narrow Band (UNB), Low Power Long Range (LoRa), Low Power Long Range Wide Area Network (LoRaWAN), Weightless, or a system utilizing Third Generation (3G), Fourth Generation (4G), Fifth Generation (5G) New Radio (NR), or Sixth Generation (6G) radio access technologies (RATs), or any further implementations thereof. FDS or CO detection devices also may be capable of transmitting and receiving signals using a wired communication link according to any suitable communication protocol, such as Ethernet, Recommended Standard (RS)-232, RS-485, Universal Asynchronous Receiver/Transmitter (UART), Universal Synchronous and Asynchronous Receiver/Transmitter (USART), Universal Serial Bus (USB), Digital Subscriber Line (DSL), Powerline Communication (PLC), or any other suitable wired communication protocol.

The term "system on chip" (SOC) is used herein to refer to a single integrated circuit (IC) chip that contains multiple resources and/or processors integrated on a single substrate. A single SOC may contain circuitry for digital, analog, mixed-signal, and radio-frequency functions. A single SOC may also include any number of general purpose and/or specialized processors (digital signal processors, modem processors, video processors, etc.), memory blocks (e.g., ROM, RAM, Flash, etc.), and resources (e.g., timers, voltage regulators, oscillators, etc.). SOCs may also include software for controlling the integrated resources and processors, as well as for controlling peripheral devices.

The term "system in a package" (SIP) is used herein to refer to a single module or package that contains multiple resources, computational units, cores and/or processors on two or more IC chips, substrates, or SOCs. For example, a SIP may include a single substrate on which multiple IC chips or semiconductor dies are stacked in a vertical configuration. Similarly, the SIP may include one or more multi-chip modules (MCMs) on which multiple ICs or semiconductor dies are packaged into a unifying substrate. A SIP may also include multiple independent SOCs coupled together via high speed communication circuitry and packaged in close proximity, such as on a single motherboard or in a single IoT device. The proximity of the SOCs facilitates high speed communications and the sharing of memory and resources.

Various embodiments are described herein using the terms "server" and "network server" to refer to any computing device capable of functioning as a server, such as a master exchange server, web server, mail server, document server, content server, or any other type of server. A server may be a dedicated computing device or a computing device including a server module (e.g., running an application that may cause the computing device to operate as a server). A server module (e.g., server application) may be a full function server module, or a light or secondary server module (e.g., light or secondary server application) that is configured to provide synchronization services among the dynamic databases on receiver devices. A light server or secondary server may be a slimmed-down version of server-type functionality that can be implemented on a receiver device thereby enabling it to function as an Internet server (e.g., an enterprise e-mail server) only to the extent necessary to provide the functionality described herein.

As used herein, the term "transceiver" refers to a device configured to send and/or receive a signal to and/or from a wired or wireless communication network, and may be a wireless transceiver, a wired transceiver, and/or a communication interface.

In the Lightweight Machine-to-Machine (LwM2M) protocol, such as the LwM2M protocol defined according to the Open Mobile Alliance (OMA) LwM2M version 1.1 specification, the LwM2M object design enables wireless devices to conserve limited battery power and processing capability by sending extremely small messages that are indexed to more complex information. For example, the LwM2M protocol uses a tree with a depth of four, including Objects, which have Object Instances, and Resources. The Resources, which are located in Object Instances, have Resource Instances. In some implementations, each Object, Object Instance, Resource, and Resource Instance may be indicated with a 16-bit identifier (an Object ID, Object Instance ID, Resource ID, and Resource Instance ID, respectively).

Various embodiments include devices and methods useful for detecting a potential or actual fire events and/or carbon monoxide and rapidly communicate detailed information about the potential or actual fire event and/or CO detection, such as a highly accurate location and a level of CO detected to a remote server of a fire and/or CO response service. Various embodiments enable early detection and mapping of potential fire conditions and fire events, and may provide an early warning of such conditions and events of carbon monoxide that enables a rapid response for fire containment or suppression to protect health and safety.

Although some embodiments are described in relation to carbon monoxide detection, the described embodiments, other embodiments, or additional embodiments may apply to fire and/or smoke detection.

In some embodiments, a FDS or CO detection device may receive information from one or more sensors configured to detect an indication of a possible fire and/or CO. The FDS device may determine whether information received from the one or more sensors satisfies one or more threshold criteria indicative of fire and/or CO detection In some embodiments, the FDS or CO detection device may activate a transceiver in response to determining that the information received from the one or more sensors satisfy one or more threshold criteria indicative of fire and/or CO detection. In some embodiments, the FDS or CO detection device may generate a warning message comprising an alarm object in response to determining that the information received from the one or more sensors satisfies one or more threshold criteria indicative of fire or CO detection. The FDS or CO detection device may send the fire and/or CO warning message to a remote server via a communication network (e.g., using the transceiver). In various embodiments, the communication network may include a wired and/or wireless communication network. In some embodiments, the fire and/or CO warning message may include a fire and/or CO alarm object. In some embodiments, the fire and/or CO alarm object may include a structured message that includes one or more defined resources that indicate one or more readings of a sensor of the FDS or CO detection device in a Lightweight Machine-to-Machine (LwM2M) extensible object.

In some embodiments, the FDS or CO detection device may receive information from a first fire and/or CO sensor configured to measure CO concentration and may determine whether the information received from the first fire and/or CO sensor satisfies a FDS or CO detection threshold. In response to determining that the information received from the first fire and/or CO sensor satisfies the FDS or CO detection threshold, the FDS or CO detection device may obtain at least one additional sensor reading from another fire and/or CO sensor. In such embodiments, the FDS or CO detection device may determine whether another fire and/or CO sensor reading from the another fire and/or CO sensor confirms or refutes detection of carbon monoxide (e.g., an initial detection of carbon monoxide).

In some embodiments, the FDS or CO detection device may include a fire and/or CO sensor (a first sensor), and the FDS or CO detection device may obtain at least one additional sensor reading from another FDS or CO detection device. Additionally or alternatively, the FDS or CO detection device may obtain the at least one additional sensor reading from another fire and/or CO sensor deployed via a robotic vehicle.

In some embodiments, the FDS or CO detection device may send location information of the FDS or CO detection device via the communication network. In some embodiments, the FDS or CO detection device may send the fire and/or CO warning message via one or both of a wired communication network or a wireless communication network.

In some embodiments, the FDS or CO detection device may operate the processor in a low-power mode while receiving information from one or more fire and/or CO sensors configured to detect CO and determine whether the information received from the one or more fire and/or CO sensors satisfy one or more threshold criteria indicative of FDS or CO detection. In response to determining that the information received from the one or more fire and/or CO sensors satisfy one or more threshold criteria indicative of fire and/or CO detection, the FDS or CO detection device may operate the processor in a full-power mode.

In some embodiments, the FDS or CO detection device may receive a signal from the communication network indicating that the FDS or CO detection device should enter a full-power mode and report fire and/or CO sensor readings and the FDS or CO detection device may operate the processor in the full-power mode. The FDS or CO detection device may access one or more fire and/or CO sensors coupled to the processor in response to receiving the signal from the communication network, and may transmit fire and/or CO sensor information via the communication network.

In some embodiments, the FDS or CO detection device may receive a signal from another FDS or CO detection device communicating a fire and/or CO warning message, and may operating the processor in the full-power mode and access one or more fire and/or CO sensors coupled to the processor in response to receiving the fire and/or CO warning message from the other FDS or CO detection device, and may transmit sensor information via the communication network. In some embodiments, the FDS or CO detection device may receive information from at least one sensor via a wireless communication link.

In various embodiments, a FDS or CO detection device may receive information from one or more fire and/or CO sensors configured to detect an indication of an accumulation of carbon monoxide (also referred to herein as a "FDS or CO detection event."). The FDS or CO detection device may determine whether the information received from the fire and/or CO sensor(s) satisfy one or more threshold criteria indicative of fire and/or CO detection. In response to determining that the information received from the fire and/or CO sensor(s) satisfy one or more threshold criteria indicative of fire and/or CO detection, the FDS or CO detection device may activate a wireless network transceiver and send a fire and/or CO warning message to a wireless communication network using the wireless network transceiver. In some embodiments, the threshold criteria may include detecting a concentration of carbon monoxide that exceeds a threshold level. For example, some embodiments may use a CO detection threshold of 400 parts per million (ppm) CO in the air, but some embodiments may use a different detection threshold and/or multiple thresholds, as further described below.

In some embodiments, the FDS or CO detection device may send a fire and/or CO warning message that includes a fire and/or CO alarm object to the wireless communication network. In such embodiments, the fire and/or CO alarm object may include a defined resource that indicates CO gas levels, and optionally ambient reading from another type of sensor (e.g., temperature, smoke, etc.) of the FDS or CO detection device or a LwM2M extensible object. In some embodiments, the fire and/or CO alarm object may include location information of the FDS or CO detection device. The location information may include a coordinate location, such as Global Positioning System (GPS) or global navigation satellite system (GNSS) information. To enable accurate location of detected carbon monoxide, the location information may include an altitude or height indicator of the FDS or CO detection device. In some embodiments, the location information may include building-specific information or other highly local information, such as a street address, a building floor (e.g., "3rd floor"), a location within a building (e.g., "bedroom," "basement boiler room," "office #325", etc.) or other such information. In some embodiments, the FDS or CO detection device may determine its location (e.g., GPS, GNSS, etc.) in response to detecting a threshold level of carbon monoxide. In some embodiments, the location information may be geographic coordinates and altitude information, such as discussed in the OMA LwM2M version 1.1 specification. In some embodiments, the FDS or CO detection device may be configured with location information stored in memory (e.g., street address, specific floor, specific building location, etc.), which may be entered into nonvolatile memory by an installer when deployed. Additionally, FDS or CO detection devices implemented in a vehicle, aerial vehicle, boat, aircraft, or otherwise mobile (e.g., configured to be hand carried) may also determine the speed at which the device is traveling along with a timestamp reporting when the reported location and speed information were determined, and include such information in fire and/or CO warning messages.

In various embodiments, FDS or CO detection devices may be configured as integrated units that combine a FDS or CO detection chipset configured to perform operations of various embodiments, a battery power unit, and radios and antennas for supporting wireless communications, one or more fire and/or CO sensors and/or interfaces for connecting to external fire and/or CO sensor(s), all included within a package.

FDS or CO detection devices may be deployed in any area or location with a risk of CO production or exposure. For example, FDS or CO detection devices may be deployed locations or areas subject to fires, such as a forest, or in any industrial, commercial, or residential building, or any other suitable environment, such as a mine, an industrial facility, or any other location or area subject to a risk of fire and/or carbon monoxide generation or accumulation, such as a room in a home, a parking garage, a construction site, a power plant, any factory, manufacturing facility, or fabrication facility, an office, a store, a designated smoking area, a bus stop, a truck loading facility, or any other suitable location or any other suitable area where carbon monoxide may accumulate. In some embodiments, a FDS or CO detection device may be attached to or incorporated into a vehicle, such as a car or any other motor vehicle (e.g., a boat, a motorcycle, etc.). In some embodiments, a FDS or CO detection device may be deployed in, on, or near any machine, appliance, system, or location subject to carbon monoxide generation or a carbon monoxide leak, such as a building heating system, a hot water heater, a heating, ventilation, and cooling (HVAC) system, a fireplace, a stove, a furnace, a gas or charcoal grill, or any other suitable appliance or system; a tool such as a lawnmower, a generator, a snowblower, a leaf blower, a weed trimmer, or any other tool that operates using an internal combustion engine. In some embodiments, a FDS or CO detection device may be deployed in an outdoor area subject to a risk of fire, such as a forest, brush area, or another suitable location.

Once deployed, FDS or CO detection device(s) may monitor conditions in their vicinity and communicate detection events in sensor data via a wireless communication network back to a remote server or service, such as a forestry server, fire department server, emergency response center, or the like. FDS. FDS or CO detection devices may be configured with processor-executable instructions to perform operations of various embodiments with a degree of autonomy to detect the presence or possibility of fire events and/or carbon monoxide detection and take appropriate actions to report such information the central server or service. The FDS or CO detection chipset included within FDS or CO detection devices may include neural network processing capabilities (e.g., a neural network engine configured to execute a trained neural network) for interpreting information from one or more fire and/or CO sensors to infer the presence of fire or carbon monoxide at locations remote from FDS device.

FDS or CO detection devices may be configured to communicate using a variety of wireless communication technologies, which may include capabilities to communicate with a wireless wide area network (e.g., a cellular telephone/data communication network) with access to the Internet, exchange data and control signals with sensors via short range communications (e.g., Bluetooth Low Energy (BLE)), and in some embodiments establish wireless mesh network (WMN) communications with other FDS or CO detection devices, as well as other devices (e.g., smoke detectors, security systems, smart thermostats, smart appliances, etc.) within wireless communication range (e.g., via IEEE 802.11b/g protocols). Further, the FDS or CO detection chipset may be configured to receive software and data updates and revisions via over-the-air (OTA) update processes supported by a wireless wide area network (WWAN), such as a 5G network.

In some embodiments, the FDS or CO detection device may be configured to conserve battery power in order to operate for long periods of time without battery recharging or replacement. In some embodiments, the FDS or CO detection device may be configured to operate the processor in a low-power mode while receiving information from one or more fire and/or CO sensors configured to detect an indication of a possible fire or carbon monoxide and determine whether the information received from the fire and/or CO sensor(s) satisfy one or more threshold criteria indicative of a fire event and/or presence of carbon monoxide, and to operate the processor in a higher power or full-power mode in response to a sensor input exceeding a predefined threshold. In some embodiments, the FDS or CO detection device may receive a signal from the wireless communication network indicating that the FDS or CO detection device should enter a full-power mode and report sensor readings. In such embodiments, in response to receiving the signal from the wireless communication network, the FDS or CO detection device may operate the processor in the full-power mode, access one or more fire and/or CO sensors coupled to the processor, and transmit sensor information to a central FDS or CO detection service via the wireless communication network.

In some embodiments, a FDS or CO detection device may signal another FDS or CO detection device to power up and report sensor information to a central FDS or CO detection service via the wireless communication network. For example, a FDS or CO detection device that detects a potential or actual fire event and/or detection of carbon monoxide may send a signal to nearby FDS or CO detection device(s) to detect and report conditions in their vicinity. Alternatively, a FDS or CO detection device may intercept a report of a fire event and/or carbon monoxide detection transmitted by a nearby FDS or CO detection device to a central service and enter a power up state in response. In this manner, a FDS or CO detection device that detects a potential or actual fire event by one FDS device and/or presence of carbon monoxide may trigger other FDS or CO detection devices to provide information to a central FDS or CO detection service that may enable early and accurate mapping of the potential or actual fire event and/or carbon monoxide accumulation. In some embodiments, a FDS or CO detection device may receive a signal from another FDS or CO detection device communicating a fire and/or CO warning message, and in response to receiving the signal from another FDS or CO detection device communicating a fire and/or CO warning message may operate the processor in the full-power mode and accessing one or more fire and/or CO sensors coupled to the processor, and transmit sensor information to the wireless communication network.

In some embodiments, two or more FDS or CO detection devices may be configured to establish a wireless ad-hoc or mesh network (e.g., a BLE or Wi-Fi mesh network) to expand a coverage area for fire and/or carbon monoxide detection. In some embodiments, a FDS or CO detection device may communicate with other sensors and wireless devices using a wireless or wired (e.g., a National Instruments 9205-type connection) communication link. The FDS or CO detection device may establish a wireless communication link with one or more other FDS or CO detection devices, as well as other wireless enable devices (e.g., smoke detectors, security system sensors, smart thermostats, equipment controllers, etc.) to form a mesh network that provides fire, CO and other sensor information over a wide physical area. In some embodiments, one FDS or CO detection device may be configured to operation as a master node or controller node in the mesh network. In some embodiments, a mesh network of FDS or CO detection devices and other wireless enable devices may use a protocol such as Message Queuing Telemetry Transport (MQTT). In some embodiments, sensor devices, or FDS or CO detection devices operating as mesh network nodes, may be added or removed from the network using standard messages such as "publish," "subscribe," or other messages specified in or compatible with the communication protocol.

Any of a variety of fire and/or CO sensors and other types of sensors (e.g., temperature sensors, smoke sensors, cameras, carbon dioxide sensors, chemical sensors, etc.) and sensor assemblies may be coupled to a FDS or CO detection device, within the FDS or CO detection device package and/or in separate units, modules, or packages. In various embodiments, the FDS or CO detection device may receive information from various sensors via a wired communication link, such as a communication bus (e.g., for a sensor on board the FDS or CO detection device) or a wired communication link (e.g., for a sensor deployed remotely from the FDS or CO detection device). In various embodiments, the FDS or CO detection device may receive information from the CO and other sensors via a wireless communication link (e.g., utilizing BLE, Wi-Fi, or any other suitable wireless communication protocol). Nonlimiting examples of sensors and sensor technologies that may be coupled to an FDS device in various embodiments include heat or thermal sensors, humidity sensors, smoke detectors, carbon dioxide ($CO_2$), carbon monoxide (CO) sensors as well as other chemical sensors, microphones and other sound sensors, wind speed and direction sensors, infrared light or thermal sensors, visible light cameras, and moisture sensors (e.g., soil moisture). In some embodiments, an FDS or CO detection device may be configured to communicate with a set of dedicated sensors (i.e., sensors that provide data solely to the FDS or CO detection device). In some embodiments, FDS or CO detection devices may be configured to communicate with sensors that also communicate and share sensor data with other FDS or CO detection devices (i.e., some sensors may be shared among FDS or CO detection devices).

Temperature sensors may be, for example, either or both direct temperature sensors, such as thermistors, and indirect temperature sensors, such as infrared sensors. In some implementations, direct temperature sensor(s) may be deployed on the exterior of the packaging enclosing the FDS device chipset and/or implemented in separate units (e.g., thermistors on wires that can be deployed away from the FDS device package). In some implementations, direct temperature sensors may be implemented in small packages that can be scattered around an FDS device and communicate temperature information using wireless transmissions (e.g., BLE signals). Indirect temperature sensors may include IR sensors that are coupled to a lens that enables a wide angle (e.g., 180°) field of view. Some embodiments, IR sensors may be configured in the form of IR cameras that are capable of providing thermal imagery in particular directions. In some embodiments, multiple thermal sensors may be employed, such as an omnidirectional IR sensor configured to detect hotspots with the temperature exceeding a particular threshold that serves as a wakeup signal for the FDS device chipset that can then activate a more capable thermal sensor (e.g., an IR camera) to provide more refined or detailed information.

Humidity has a big impact on the potential and intensity of forest and brushfires. Therefore, some embodiments may include a humidity sensor as part of the sensor suite. Any of a variety of humidity sensors may be used in various embodiments.

Smoke sensors may use any of a variety of conventional smoke detector technologies, as well as camera-based sensors configured to detect smoke via visible images, spectral analysis, and/or thermal analysis. Further, multiple smoke detectors may be employed in some embodiments with the detectors calibrated to different levels of smoke intensity to enable the FDS device to have different levels of sensitivity. For example, to avoid false alarms, a smoke sensor that is less sensitive than other smoke sensors in the FDS device may be used as the sensor used to trigger wakeup or activation of the FDS device. Once activated, more sensitive smoke sensors may be used to characterize detected fire. Also, in FDS devices that are remotely activated, more sensitive smoke detectors may be used to confirm reports received from other FDS devices.

Any of a variety of $CO_2$ sensors (or other chemical sensors) may be used in various embodiments. In some embodiments, in order to avoid false alarms, a threshold for waking up the FDS device and reporting potential fire or CO detection events may be set at a high level of CO or $CO_2$. After being activated, FDS devices may report CO or $CO_2$ levels at levels lower than the wakeup threshold so as to provide a central service with information regarding fire conditions and extent.

Any of a variety of CO sensors (or other chemical sensors) may be used in various embodiments. In some embodiments, in order to avoid false alarms, a threshold for waking up the FDS device and reporting potential detection events may be set at a high level of CO. After being activated, FDS or CO detection devices may report CO levels at levels lower than the wakeup threshold so as to provide a central service with fire and/or CO-related information regarding fire conditions and extent.

Wind information (e.g., speed and/or direction) are important parameters for predicting the path and/or speed of advance of forest and brush fires. Wind speed may have a strong impact on the intensity of forest and brushfires and particularly in causing fire fronts to advance. Further, high winds can lead to wildfires in some circumstances, such as by knocking down power lines that can spark fires and blowing embers out of campfires. Wind direction is very important to firefighters for deploying firefighting resources and identifying populated areas and structures that may be threatened by a fire front. Further, once a fire starts, the heat from flames can create local weather conditions that can accelerate fires and cause fires to advance in directions that are not necessarily predictable based on the macro wind conditions. In some implementations, wind direction information may be combined by the FDS chipset processing with detection of smoke or elevated CO or $CO_2$ levels to provide a relative vector toward a fire source.

A variety of different types of wind speed and direction sensor(s) may be deployed within or coupled to an FDS device. Conventional wind speed and direction sensors including a wind vane and a rotating anemometer may be built into or deployed as a separate sensor FDS device. Integrated wind sensors may also be possible, such as one or more condenser microphones on the surface of the FDS device that can measure wind speed approximately based upon the sounds that are made passing over the microphone opening. Wind direction sensors using condenser microphone-type sensors may include an array (e.g., a triangular array) that enables a processor of the FDS device chipset to determine the wind direction based upon the timing difference of wind sounds detected by each of the condenser microphones. Other types of wind speed and direction sensors may be deployed.

In some implementations, wind information sensors (e.g., a sensor configured determine wind speed information and/or a sensor configured to determine wind direction information) may remain in a low-power or sleep mode until activated in response to detection of a potential fire event based on other sensor data. For example, in response to detecting smoke by one or more of the smoke sensors and/or as processed by the device after receiving information from the smoke sensor(s), the wind sensors may be activated (e.g., by the FDS chipset) so that a direction from the FDS device to a source of the smoke may be determined, information that may enable a remote server to estimate a location of a fire based on input from multiple FDS devices. In some embodiments in which wind speed is measured by a rotating anemometer, the anemometer may be used recharge batteries of the sensor module and/or the FDS device. In some embodiments, wind information sensors may be deployed as one or more separable units that communicate via wireless communications (e.g., BLE communication link or the like) with an FDS device so that the sensor can be located at the top of a tall tree or on a platform where true wind conditions may be measured.

Since high winds can cause or contribute to forest and brush fires, in some implementations, wind information sensors (e.g., a sensor configured determine wind speed information and/or a sensor configured to determine wind direction information) may remain in a low-power or sleep mode until activated in response to some external trigger. For example, wind information sensors may be put into a high-power mode or the FDS chipset may begin accessing information from the wind information sensors in response to a high wind warning received from an external weather service. As another example, a wind speed sensor may be configured to send an interrupt or other signal to the FDS chipset upon detection of a very high wind speed, and in response the FDS chipset may begin receiving wind sensor information, including activating wind information sensors or initiating a high-power mode for such sensors. As an example, in implementations in which a wind speed sensor is configured to operate as a battery charger, detection of a voltage or current generated by the wind speed sensor exceeding a threshold value may generate an interrupt that prompts the FDS chipset to begin gathering and potentially reporting wind information.

Some embodiments may include microphones or similar sound sensors that are configured to capture ambient sounds and provide sound information to the FDS device chipset. Sound may provide information useful for detecting and fighting forest and brushfires. For example, the popping and snapping of burning wood may have characteristic audio patterns (e.g., amplitude or frequency of the sounds) that can be detected using simple audio analysis algorithms. As another example, the presence of fire causes animals to respond in a manner that may be recognized, such as using neural network or other machine-learning methods, to determine the presence or absence of fire. For example, the patterns in bird songs may indicate the presence of fire or a sudden absence of bird songs may indicate that fire is near. In some embodiments, a processor of the FDS device chipset (e.g., a neural network processor) may be configured to analyze normal ambient sounds and recognize the difference in ambient sounds as a potential indication of a fire event. In some embodiments, the detection of fire by recognizing the sounds of burning wood may be useful for pinpointing fire fronts for firefighters deciding how to deploy firefighting resources.

Some embodiments may include various types of soil sensors, such as soil temperature and soil humidity/moisture sensors, as soil temperature and humidity can be factors in how a forest or brush fire burns. Thus, some FDS devices may be equipped and deployed with soil sensors (e.g., with a sensor pushed into the ground). In some embodiments, the FDS device may correlate information received from multiple sensors, which may improve the accuracy and informational content of a fire event detection. In some embodiments, the FDS device may receive information from a first sensor configured to measure a local or remote ambient temperature, and may determine whether information received from the first sensor satisfies a threshold consistent with a fire condition. In response to determining that the information received from the first sensor satisfies the threshold consistent with a fire condition, the FDS device may obtain at least one additional ambient reading from another sensor, and may determine whether there is a correlation of the information received from the first sensor and the at least one additional ambient reading consistent with a fire event. In response to determining that there is a correlation of the information received from the sensor and the at least one additional ambient reading consistent with a fire event, the FDS device may determine that the information received from the one or more sensors satisfy one or more threshold criteria indicative of a fire event.

In some embodiments, the FDS device may apply the information received from the one or more sensors to a trained neural network, the output of which may indicate that there is a correlation of the information received from the sensor and the at least one additional ambient reading consistent with a fire event. In various embodiments, the FDS device may include, or may be configured to execute, a runtime environment or for the execution of deep neural networks. The provided runtime environment may enable various users of FDS devices to load onto the FDS devices a customized or separately trained neural network, which may execute in the runtime environment. In various embodiments, the neural network runtime environment may be implemented in hardware, software, or any combination of hardware and software.

In some embodiments, the first sensor may include a local ambient temperature sensor, a remote temperature sensor, a smoke detector, an image sensor, and/or an infrared sensor. In some embodiments, additional sensors may include an ambient humidity sensor, a smoke sensor, a CO sensor, a $CO_2$ sensor, another chemical sensor, a wind sensor, a sound sensor, a soil sensor, an image sensor, and/or an infrared sensor.

In some implementations, the FDS device may receive weather information and/or other environmental information from remote sources, such as a weather forecast service accessible via the Internet via a wireless communication network, and use such information regarding the local environment to evaluate the information received from the one or more sensors. In some embodiments, the FDS device may receive updates to sensor thresholds or threshold criteria from a remote server via an OTA procedure, such as in anticipation of a forecasted weather event that may influence fire conditions. In some embodiments, the FDS device may dynamically select or determine thresholds or threshold criteria indicative of a fire event based at least in part on the weather information and/or other environmental information. In some embodiments, the FDS device may send an environment information request to the wireless communication network in response to determining that the information received from the one or more sensors satisfy one or more threshold criteria indicative of a fire event. The FDS device may receive from the wireless communication network environment information for the area proximate to the FDS device. In some embodiments, the FDS device may determine a correlation of the ambient temperature, the at least one additional ambient reading and the received environment information for the area proximate to the FDS device. In some embodiments, the FDS device may determine that the ambient temperature exceeds a second temperature threshold, an ambient humidity exceeds a humidity threshold, and a smoke reading is positive. In such embodiments, the second temperature threshold and the humidity threshold may be based on environment information for the area proximate to the FDS device.

In some embodiments, the FDS device may receive one or more images from a visible light camera and/or an infrared camera. The FDS device may send one or more of the images to the wireless communication network with or after the fire warning message. In some embodiments, the FDS device may send location information of the FDS device to the wireless communication network.

In some embodiments, FDS devices with varying capabilities and different sensor capabilities (e.g., sensors that are part of the FDS devices and/or sensors that separate but coupled to the FDS devices) may be deployed in an area. For example, certain types of sensors and processing capability may be more appropriate in some locations (e.g., treetops) while a different set of capabilities and sensors may be more appropriate and other locations (e.g., ground-level). Further, some FDS devices may be equipped with low-cost sensors and integrated into low-cost packages for widespread large number deployments while other FDS devices within the overall fire detection system may have more sophisticated or higher resolution sensor capabilities for deployment in particular high-risk or optimal observation locations. In such system deployments, the low-cost widely deployed FDS devices may provide early warning of the potential presence of a fire event without the ability to pinpoint its location while fewer, more complex FDS devices can be deployed in the same area to be activated by the system to provide more precise information for describing area conditions and pinpointing fire locations. In particular embodiments, the same chipset may be deployed in all FDS devices due to the cost efficiency of mass production of standard systems on chips. Such embodiments may be useful in deploying sophisticated processing and communication capabilities throughout a forest area, particularly because the functionality of FDS devices may be augmented or changed using over-the-air update technologies.

In some embodiments, FDS devices may be configured with different reporting thresholds, such that some FDS devices will activate and report a fire event at a lower level of threshold than other FDS devices in a given deployment. For example, FDS devices that are deployed on an edge of a forest or a fire break have less area to monitor or a lower threat condition, and therefore the reporting thresholds may be adjusted accordingly. In some implementations, because resource demands on FDS devices deployed in such lower threat locations will be lower, such FDS devices may be configured to provide services for other FDS devices such as serving as a master node or a redundant wireless communication node for accessing a wireless communication network (e.g., a cellular network) on behalf of FDS devices deployed in areas with a higher threat condition.

Various embodiments may provide valuable information for detecting the presence or potential for a forest or brushfire. Some embodiments, the FDS devices may also be configured with capabilities that will be useful for firefighting, such as providing information useful in determining the direction and speed of advance of fire fronts, local temperature and humidity conditions, and other local factors that are useful to firefighters. Even the failure of an FDS device caused by overheating in a fire may provide information regarding the presence of the fire front. On the other hand, some embodiments may provide an option to selectively turn off FDS devices or place FDS devices in a low-power or sleep mode once a fire/threat is confirmed so as to conserve battery power for continued use after a fire has been contained.

As noted above, in various embodiments, FDS or CO detection devices incorporated into a vehicle, such as a car, a boat, a truck, or another vehicle that may generate carbon monoxide or may be present in a location or area in which carbon monoxide may accumulate. In some embodiments, an FDS or CO detection chipset may be incorporated in or coupled to a chipset or other device of the vehicle. Examples of situations in which carbon monoxide may accumulate include a car in a garage or other enclosed space, a motorboat in a following wind, a sailboat that includes a below-decks generator, and the cabin of a semi or delivery truck. An FDS or CO detection device may be included in a vehicle to detect engine exhaust or tailpipe emissions, in a seating area, cabin, cockpit, sleeping area, or other area of a vehicle configured to accommodate a driver and/or passengers, and/or an area around the vehicle.

In some embodiments, in response to detecting a carbon monoxide concentration higher than a detection threshold, the FDS or CO detection device may send a fire and/or CO warning message to one or more other devices. For example, the FDS or CO detection device may power up a wireless transceiver and send a fire and/or CO warning message to a server and/or to a user device (such as a mobile device or other wireless device). The FDS or CO detection device may send the fire and/or CO warning message to the user device to notify the user that immediate action may be required to mitigate the detected carbon monoxide. In some embodiments, the FDS or CO detection device may send the fire and/or CO warning message to another device of the vehicle, such as a vehicle processor (e.g., via wired or wireless communication link with the vehicle and/or a communication network). In response to the fire and/or CO warning message, the vehicle processor may take an action such as presenting a warning (which may be visual, audible, tactile, etc.) to a driver or passenger, maneuvering the vehicle (e.g., moving a car to another area, turning a boat relative to the wind), opening a window, sun roof, or hatch, activating a vent, or another suitable action.

In some embodiments, the FDS or CO detection device may send the fire and/or CO warning message to a network server or similar device, such as a server of a CO response service, a smart building system (e.g., an Internet of Things (IoT) hub device or another device that may be part of a home network or building network), or another suitable network server. In some embodiments, in response to receiving the fire and/or CO warning message, the network server may take an action to mitigate the detected carbon monoxide. For example, the network server may shut off an appliance, such as shutting off a gas stove in response to detecting carbon monoxide in a kitchen, or shutting down a furnace in response to detecting carbon monoxide in the area. In other embodiments, the network server may open a window or a garage door, or activate a vent fan or an exhaust system, to ventilate the area in which carbon monoxide has been detected. In some embodiments, the network server may present an alarm and/or or sending a notification to a mobile device and/or other IoT devices (such as a smart speaker device, an IoT-enabled pillow (e.g., which may vibrate to wake a sleeping person), a connected television or other display, cause a smart lighting system to flash, vibrate a smart watch or other wearable device, ring telephones as an audible warning, trigger an industrial alarm or warning system, trigger or otherwise cause activation or control of a device for confirming the alarm (e.g., robotic vehicle, etc.).

In some embodiments, the network server may send a fire and/or CO warning message to one or more other devices, such as a user device (e.g., a smartphone or mobile computer), other FDS or CO detection devices or fire and/or CO sensor(s), or other types of sensor devices. In some embodiments, the network server may send the fire and/or CO warning message to a vehicle processor (e.g., via wired or wireless communication link with the vehicle and/or a communication network). In some embodiments, the network server may instruct the vehicle processor to take an action such as present a warning to a driver or passenger, maneuver the vehicle, open a window, sun roof, or hatch, activate a vent, activate an HVAC system, or another suitable action.

In some embodiments, in response to receiving the fire and/or CO warning message, the network server may activate one or more other types of sensors to obtain additional information. Non-limiting examples of other types sensors that may be activated include cameras, smoke detectors, temperature sensors (e.g., a thermistor or an infrared temperature sensor), other chemical sensors, microphones or other sound sensors, or and the like. One or more additional types of sensors may be activated in addition or as an alternative to presenting an alarm immediately upon detecting carbon monoxide over a threshold concentration. Such information may enable the network server to determine a source of the detected carbon monoxide, such as a fire, a gas leak or a chemical leak, a car left running in a garage, building entry area, or loading dock, etc. In some embodiments, the one or more other sensors may provide additional information about the detected carbon monoxide, such as more detailed location information, boundaries or edges of an affected area, concentration density, and other such information.

In some embodiments, in response to receiving the fire and/or CO warning message, the FDS or CO detection device and/or the network server may activate one or more robotic vehicles to maneuver to the location of the detected carbon monoxide. One or more robotic vehicles may be activated in addition or, or as an alternative to, presenting an alarm immediately upon detecting carbon monoxide over a threshold concentration. A robotic vehicle may be deployed in any of a variety of environments, include a home, an industrial facility (e.g., a factory, a mine, a power plant, etc.), an area of forest or brush, or another suitable area. For example, obtaining additional information about the detected carbon monoxide in the industrial facility may be too hazardous for human workers, who may be evacuated from the facility, but the additional information could be obtained by a robotic vehicle without risk to human life or safety. In some embodiments, the robotic vehicle may be an autonomous or semi-autonomous ground robotic vehicle, airborne robotic vehicle (e.g., a drone), water surface or submersible robotic vehicle, etc.

In some embodiments, the FDS or CO detection device, or another local computing device, may active the robotic vehicle(s) before contacting the server. Such embodiments may enable more and dispersed CO concentration measurements to be made to support a more conclusive detection of carbon monoxide or permit the confirmation of an initial FDS or CO detection before sending a fire and/or CO warning message to the network server. Alternatively, the robotic vehicle may be activated and a notification may be sent to the network server at approximately the same time. In such embodiments, the server may be configured to control or direct the robotic vehicle to obtain additional information (e.g., more and dispersed CO level measurements) that the server can use to confirm or refute an initial detection of carbon monoxide. Such additional CO measurements provided by the robotic vehicle(s) may be used by the server to determine whether to sound an alarm and/or notify first responders (if the initial FDS or CO detection is confirmed), or to cease an alarm and/or call back first responders (if the initial FDS or CO detection is refuted).

In some embodiments, the robotic vehicle may be configured with one or more fire and/or CO sensors as well as other sensors (e.g., cameras, smoke detectors, thermal sensors, etc.). A robotic vehicle may be used to find a more accurate source of the detected carbon monoxide (e.g., particular rooms within a building) to help users make decisions as quickly, for example, which way to exit a burning building; to leave a door to a burning room closed to slow down the spread of fire or smoke; which rooms to avoid while escaping; to disable electronics/circuitry in the area to avoid sparks; and other suitable actions. In some embodiments, the robotic vehicle may be configured to obtain other sensor information to provide additional information about the detected carbon monoxide, such as more detailed location information, boundaries or edges of an affected area, concentration density, and other such information. In some embodiments, the robotic vehicle may be configured to obtain information from other types of sensor to look for other indicia of carbon monoxide generation, such as a fire, a fault in industrial equipment or a home appliance, or another suitable indication. In some embodiments, the robotic vehicle may be configured to obtain sensor information about the detected carbon monoxide, which may confirm or refute the FDS or CO detection by the FDS or CO detection device. In such embodiments, the network server may sound an alarm, continue an alarm, escalate an alarm (e.g., increase an alarm volume, send messages via email, text, etc., notify emergency services, etc.), or discontinue an alarm, based on the additional information obtained by the robotic vehicle's sensors (and/or stationary sensors).

In some embodiments, if the initial detection of carbon monoxide is confirmed, the robotic vehicle may perform further actions. In some embodiments, the robotic vehicle may sound an alarm (i.e., an alarm that is part of the robotic vehicle or an alarm remote from the robotic vehicle). In some embodiments, the robotic vehicle may be configured to investigate possible FDS or CO detections autonomously, without a communication link to a communication network. In such embodiments, the robotic vehicle may independently confirm the initial detection of carbon monoxide, and may activate a modem or a wireless transceiver to send a notification to, e.g., a network device or server. In some embodiments, the robotic vehicle may travel to a different location to provide a notification of the confirmed FDS or CO detection. For example, the robotic vehicle may maneuver to a bedroom where occupants are sleeping, to provide a notification such as an alarm, a voice message, etc. directly to the occupants. In some embodiments, the robotic vehicle may send a message (e.g., via a wireless communication link) to an entity (that may or may not be nearby), such as a homeowner, manager, interested third party, emergency services, etc.

In some embodiments, other sensor(s) may be activated and/or robotic vehicle(s) may be deployed to one or more areas near or proximate to a FDS or CO detection location. In some embodiments, the other sensors may be smaller, cheaper sensors deployed throughout a home, office building, industrial facility, etc., that report sensor readings to a network device (e.g., server). In some embodiments, when other sensor(s) and/or robotic vehicle(s) are activated to investigate a FDS or CO detection, the network server, other sensor(s) and/or robotic vehicle(s) may be configured to use two or more different detection thresholds. For example, while a detection threshold of 400 ppm may be used to detect carbon monoxide at the location of its generation or leakage, a lower threshold (e.g., 200 ppm) may be employed for stationary or robotic vehicle-deployed sensors near the initial detection area (e.g., an adjacent area or room, a floor above or below the initial detection area). Also, in such a mode the FDS or CO detection device may increase the frequency at which sensors are monitored (i.e. increase the sensor sampling rates) and/or sensor data is reported to a central service. For example, if another FDS or CO detection device has transmitted a fire and/or CO warning message, operating surrounding FDS or CO detection devices using lower thresholds for reporting events may be beneficial to providing early and complete warning of carbon monoxide accumulation without increasing the number or likelihood of false alarms.

In some embodiments, a robotic vehicle may be configured to provide information about the detected carbon monoxide even if the robotic vehicle is unable to maneuver to a desired location. For example, a closed or locked door, debris, etc. may prevent a robotic vehicle from traveling to or through a particular area.

In various embodiments, the robotic vehicle (and/or the FDS or CO detection device) may be configured to indicate a probability indicator or a probability assessment of the one or more sensor readings (e.g., "50% chance of a fire," "2% chance of fire," "80% change of gas leak," etc.). In some embodiments, the robotic vehicle (and/or the FDS or CO detection device) may determine the probability indicator or a probability assessment based on one or more of the location of the detected carbon monoxide, the distance of the robotic vehicle from the location of the detected carbon monoxide, and/or the one or more other sensor readings obtained by the robotic vehicle. In some embodiments, the robotic vehicle may provide the various sensor readings to a network device (e.g., server) or the FDS or CO detection device (which may provide the sensor readings or corresponding data to the network device), and the network device or the FDS or CO detection device may determine a reliability of the sensor readings and/or a reliability of the original FDS or CO detection based on the various sensor readings obtained by the robotic vehicle (and/or various sensor readings obtained by other sensor(s)).

In some embodiments, the network server may be operated by any number of organizations and may perform a variety of actions in response to receiving the fire and/or CO warning message. For example, the network server of a CO response service may send a notification to a user device, such as by a text message (e.g., short message service (SMS)), a phone call, or another alert message. In some embodiments, the network server may send a warning or notification to a public safety answering point (PSAP, e.g., 911) or to emergency services (e.g., fire, police, etc.). In some embodiments, the network server may send such a warning or notification to a third party after confirmation of the detected carbon monoxide (e.g., using additional sensor information, sending in a robotic vehicle with various sensors, etc.). In some embodiments, the network server may send a fire and/or CO warning or notification to an area proximate to the detected carbon monoxide (i.e., devices in or otherwise associated with that area), such as one or more entire floors of a building or an entire building, a neighborhood or other residential area, and the like. In some embodiments, such a warning of notification may recommend a course of action, such as evacuation, shelter in place, etc. based at least in part on the detected carbon monoxide and/or information from one or more other sensors (including robotic vehicle-deployed sensors). In some embodiments, the network server may determine an area to receive the fire and/or CO warning or notification based on the information received from the FDS or CO detection device and/or one or more other sensors.

In some embodiments, the FDS or CO detection device may send the fire and/or CO warning message to a server of the manufacturer of the vehicle. Such information may be useful to the manufacturer to detect problems such as design flaws or operation flaw (such as unintended interactions of the various complex systems of a vehicle). In some embodiments, fire and/or CO warnings received from multiple vehicles may help the manufacturer address a problem proactively, such as by issuing a recall or publishing a solution to a problem with the vehicle.

In some embodiments, a fire and/or CO warning may be sent to interested parties, such as an insurance company, a vehicle fleet operator, a ride provision or ride sharing company (e.g., Uber, Lyft), etc., to provide information relevant to risks posed by a particular vehicle or vehicle type. Such warnings to third parties may be transmitted to network devices (e.g., servers via the Internet) as well as smartphones and other devices to enable such third parties to take an action based on the warnings.

In various embodiments, FDS or CO detection devices may receive updates to the software and operational data via OTA procedures via a WWAN. OTA update procedures may enable FDS or CO detection devices to be stored for a long period of time before your deployment, receiving updates the software and operational data once deployed via OTA. Similarly, OTA update procedures may enable FDS or CO detection devices to be individually configured to operate in the particular location (e.g., environment or vegetation conditions) in which each FDS or CO detection device is deployed. OTA update procedures may also enable reporting thresholds to be adjusted by a remote server, such as to respond to changing whether or seasonal conditions. OTA update procedures may be useful in configuring deployed FDS or CO detection devices to operate in new ways to support new fire detection and firefighting techniques or strategies. In some cases, new capabilities may be deployed in FDS or CO detection devices via OTA update procedures. Changes in communication networks, protocols, and/or authentication/security measures may also (or alternatively) be deployed via OTA update procedures.

FDS devices may be deployed with a variety of sensors that may be selected or optimized for the geographic location where the FDS devices will be deployed considering the types of vegetation and fuels in the area of deployment. Different vegetation (which may change based on dryness/humidity or based on time of year) have different flash/fire points, burn at different rates, and thus may lead to higher or lower temperatures. Therefore, different types of sensors may be more useful in a forest location given the nature of forest fires and the local conditions caused by trees compared to brush land which is characterized by open areas of low-lying flammable materials. Thus, different configurations sensor suites may be deployed on FDS devices depending upon the type of fire that is anticipated, such as a brush fire, bushfire (e.g., in Australia), desert fire, forest fire, grass fire, hill fire, peat fire, vegetation fire, or veld fire (e.g., in South Africa).

As noted above, various embodiments may include a battery power unit that provides power to the sensors as well as the FDS or CO detection chipset to enable the devices to operate as separately deployed units. To permit extended operations using battery power, the FDS or CO detection device may be configured to remain in a low-power mode or state until a sensor detection of an external event (e.g., a command received via a WWAN from a central service or a wireless signal received from another FDS or CO detection device) prompts the FDS or CO detection chipset to transition to a high-power mode or state. The battery power unit may include multiple batteries, different types of batteries, charge state monitoring circuitry, charging circuitry, and other components. In some embodiments, the FDS or CO detection device may be configured to enter or exit a low-power mode based on other events in its environment. For example, the FDS or CO detection device may be configured to exit the low-power and transition to the high-power mode or state when a vehicle is detected in a garage, or when an engine, tool, or appliance is activated. For example, the FDS or CO detection device may be configured to enter the low-power mode when no vehicle is detected for a period of time, or when an engine, tool, or appliance is deactivated.

In some embodiments, the unit or package may include capabilities to charge/recharge the battery power unit of the FDS device. For example, embodiments that include a rotating wind speed sensor (i.e., an anemometer) that measures wind speed based on the amount of current or voltage induced by the rotating element may also be used to charge or recharge the battery power unit. As another example, solar cells may be positioned on an exterior surface of the FDS device (or may be separate units connected by a conductor to the FDS device) and configured to charge/recharge the battery power unit(s) during daylight hours. Including renewable charging capabilities may enable the FDS device to execute more functions on a normal operating basis. Wind and/or solar-powered FDS devices have the added ability to perform certain functionality at all times, such as using more active sensors like infrared or visible light cameras to detect signs of fire, then possible with battery only powered FDS devices. Such embodiments may include the capability to reorient a wind sensor/generator or solar cells so as to achieve greater power (e.g., face the wind prevailing winds, or face the sun) depending upon the location of deployment and season. Other forms of renewable energy generators may be coupled to FDS devices, such as a water wheel positioned in a stream.

In some embodiments, the FDS device (and/or some of the sensors) may be included in a package that has the capability of surviving exposure to a forced or brushfire. For example, embodiment packaging may include thermal insulation, which may be in a form that can be articulated such as to form a protective shell around the FDS device.

In some embodiments, FDS devices (and/or some of the sensors) may be capable of moving and self-deployment. For example, some FDS devices may be implemented as or coupled to an unmanned aerial vehicle (UAV) so that the FDS devices can be remotely deployed to treetop and mountain locations or other difficult to access locations. Such embodiments may also be capable of flying to escape destruction by fire front after reporting detection of fire. Similarly, some FDS devices may be deployed within ground-based mobile autonomous vehicles configured to move through forest and brush conditions. Such ground mobile FDS devices may be particularly useful in deploying in dense forest and brush conditions where individuals could not easily travel. Air mobile and the ground mobile FDS devices may also be configured (or controllable) to reposition to achieve better sensor readings and/or achieve more power generation from a wind generator and/or solar cells to enable battery recharging (e.g., increasing sun exposure to solar cells).

In some embodiments, some mobile FDS devices may be configured to move towards detected or potential fire events in order to position sensors closer to the fire front in order to obtain more precise or complete information. Moving closer to a potential fire event may enable FDS devices to obtain better (and/or additional) information for confirming sensor readings and building confidence that a fire has started, as well as information to more precisely identify the location of the fire and/or a direction of movement of the fire front. An FDS device configured as the UAV may fly to a new location and/or take sensor readings while airborne so as to obtain information closer to a potential fire location. As another example, a ground mobile FDS device may move to a new location where sensor readings may be obtained from a different perspective or from a better vantage point of the suspected location of a potential fire event. FDS devices may continue moving to new locations to take and report more sensor readings. In some implementations, an FDS device may leave an area near a fire once enough sensor information has been gathered and reported, such as following and acknowledgment by a remote server.

Deploying FDS devices on UAVs (or otherwise having mobile devices/sensors) has the added advantage of enabling a wide area to be surveyed by a smaller number of FDS devices. For example, UAVs may be redeployed to areas of particular fire threats, and then moved to other areas as the risk of fire or fire conditions change. As another example, UAVs may be moved from forests that have experienced rain to locations that remain in drought conditions where the threat of wildfires remains high. Further, mobile FDS devices have the advantage of being able to be deployed by firefighters to areas where they need more information to manage their firefighting efforts.

In some embodiments, part or all of an FDS device may be configured to turn, bend, articulate or otherwise reorient or change position so as to better the position of the FDS device or the sensor for acquiring information. For example, a visible or IR light sensor may be positioned on a rotatable stalk that can reorient a lens to provide 180° view of surroundings. As another example, a wind speed sensor configured to also charge the battery power unit(s) of the FDS device may be configured with an actuator to position the rotating portion of the sensor in the wind. As another example, a solar cell on the FDS device may be configured with an actuator to enable the cell to be oriented to better receive solar illumination. In such embodiments, the FDS device chipset may include accelerometers capable of detecting a gravity vector, and be configured with processor-executable instructions to determine a change in orientation or angle that is appropriate for a particular portion of the FDS device or a sensor and control an actuator to accomplish the appropriate change in orientation, pointing angle, etc. In some embodiments, FDS device chipset processors may further be configured to receive instructions from a central source, such as a remote server, to reposition or redirect sensors in a particular direction, in such embodiments, a central service may coordinate the redirection or redeployment of sensors in a particular direction, such as facing a direction of the suspected fire event so as to better provide useful information to firefighters. In such embodiments, a large number of FDS devices may be controlled and configured to focus sensor capabilities and mass on a site of fire so as to provide firefighters with relevant information from positions surrounding a fire front.

In some embodiments, FDS device chipsets may be configured to make diurnal or seasonal adjustments in operating mode of the FDS device or various sensors based on time of day or day of year. For example, FDS devices may be configured to go into a deep sleep or low-power mode during seasons in which fire risk is very low (e.g., rainy season, winter, etc.). In some embodiments, FDS device chipsets may change operating modes in response to weather, since some weather events, such as rain, may influence fire probability. For example, FDS device chipsets may be configured to enter a deep sleep or very low-power mode (e.g., lower than sleep or low-power mode) following a substantial rain event for a period of time to conserve battery power while the risk of fires is particularly low. Further, in some embodiments, FDS devices may receive seasonal updates to operating modes or sensors via OTA update processes.

In some embodiments, the FDS or CO detection device chipset may be configured to respond to signals received via a WWAN from a central service, such as a remote server providing FDS or CO detection system services, and transition out of a low-power mode to a high-power mode and begin providing sensor information. Such capabilities may enable a network device (e.g., a remote server) to activate and use the information provided by a number of FDS or CO detection devices to confirm and/or pinpoint the location of fire or carbon monoxide based upon a detection report received from a single FDS or CO detection device. The sensor information provided by FDS or CO detection devices to a network device in such circumstances may be raw sensor data (e.g., temperature readings, CO concentration readings, wind direction, etc.), processed sensor data (e.g., information regarding the rate of change in temperature, processed imagery, average wind direction, etc.), or a combination of raw and process sensor information, which may be provided as directed by the network device. Such capabilities may enable a central service (e.g., a CO response service or fire department) to use multiple FDS or CO detection devices to confirm and/or locate a fire event or presence of carbon monoxide and thus distinguish real from false alarms, which could be caused by an FDS or CO detection device malfunction or exposure to an unusual but benign condition. Further, activating and using sensor data from multiple FDS or CO detection devices may enable a central service to determine the location, movement direction, and magnitude of a fire threat, and/or carbon monoxide accumulation as well as continue to provide information useful in fighting the fire after the initial response or mitigating detected carbon monoxide.

In some embodiments, FDS devices may be configured to operate in an enhanced or more sensitive mode, such as in response to receiving a command to enter such a mode from a central service via a WWAN or in response to receiving reports of fire events from other nearby FDS devices. In such an enhanced or more sensitive mode, the FDS device chipset may use lower thresholds for reporting event based on the sensor data. Further, in such a mode the FDS device may activate and begin monitoring further sensors to obtain more information could be relevant to detecting a fire event. Also, in such a mode the FDS or CO detection device may be configured to track readings of one or more CO device may increase the frequency at which sensors are monitored (i.e. increase the sensor sampling rates) and/or sensor data is reported to a central service. For example, if another FDS device has transmitted a fire event warning message, the chances of the fire event are enhanced, and therefore operating surrounding FDS devices using lower thresholds for reporting events may be beneficial to providing early and complete warning of fire events without increasing the number or likelihood of false alarms. Thus, in some embodiments, FDS devices may wake up and begin monitoring sensors with lower thresholds for reporting sensor data, monitoring more sensors, and/or monitoring sensors more frequently in response to other FDS devices transmitting detection reports. In some embodiments, in the event of a fire, the deployed system of FDS devices may wake up autonomously and begin providing data with enhanced sampling rates and sensitivity across the affected area. Further, in some embodiments, in response to one FDS device detecting a potential fire condition, some or all of the FDS devices in the vicinity may activate and form a mesh communication network to share sensor data that can be processed in detection algorithms (e.g., using one or more trained neural networks executing in one or more FDS devices) to enable more accurate and precise detection of fire events by the deployed devices.

In some embodiments, some FDS devices may be configured with stronger radios or may be positioned to achieve longer-range wireless communications to reach a cellular or other wireless communication networks than other FDS devices. For example, an FDS device that is deployed at the top of the tree or mountaintop may be capable of communicating with a remote wireless network while FDS devices deployed in a valley or on the ground floor of the forest may not be capable of communicating with that network. Therefore, in some embodiments, some FDS devices may service as communication nodes for relaying wireless communication signals from/to FDS devices that are not capable of communicating with a wireless network. Further, in some embodiments, even if certain FDS devices are capable of communicating with a wireless network, certain FDS devices may be configured to communicate only with a nearby FDS device (which may function as a relay to the wireless network) to conserve battery power. For example, communications between FDS devices may be accomplished using known wireless communication protocols, such as wireless mesh network communication protocols (e.g., IEEE 802.11b/g, mobile ad hoc networks, Zigbee, LTE Direct or Bluetooth (e.g., BLE, Bluetooth mesh networking, etc.), to send data packets to an FDS device that is operating as a communication relay. In some embodiments, FDS devices may be configured to collaborate during deployment to identify those FDS devices that are able to reach a wireless communication network and those FDS devices that cannot, and organize the different FDS devices into slave and master communication nodes accordingly. In some embodiments, the FDS device chipsets may be configured so that such organization may be accomplished autonomously. For example, in some embodiments, FDS devices may set up or organize a wireless mesh network among the devices upon initial deployment, so that such communication capabilities can be used for ensuring conductivity of all FDS devices with the WWAN when a fire event is detected or the FDS devices or otherwise activated as described herein.

In some embodiments, a given FDS device may be configured to track readings of one or more sensors over time and process the sensor readings of the function of time to determine rates of change, such as how quickly sensor readings are changing. For example, a very steep increase in temperature readings may mean that fire is creeping closer and/or growing in strength. As another example, a sudden increase in CO readings may mean that carbon monoxide is rapidly accumulating. Similarly, a decrease in CO readings over time may indicate, for example, that a mitigation attempt (e.g., venting the area) is working, and how well (e.g., a rate at which the concentration of carbon monoxide is decreasing). Thus, a server may use CO readings over time to determine whether a mitigation attempt is succeeding, or that further measures may be required (e.g., because the mitigation effort is not working, or because the mitigation effort is not working quickly enough, etc.). Thus, FDS or CO detection device chipsets may be configured to report not only instantaneous sensor readings but also rates of change in various sensor readings over varying time durations. Further, FDS devices may be configured to process information from combinations of different types of sensors to provide correlated or integrated sensor information to a remote server. For example, an FDS device that determines that there is a likelihood of a fire event based upon imaging of smoke may activate a thermal imaging camera and correlate the visual and thermal images of the smoke before transmitting such information to the central server. As another example, an FDS device detecting threshold level of CO in the air may obtain wind information (e.g., wind speed and wind direction information), and include the wind information in reports of the CO levels to the remote server.

A remote server, such as a server of both forestry service or fire department, may be configured to store and analyze reports from the network of FDS devices to provide information useful for determining the cause or start of a fire. For example, since sensor readings by each FDS device are tracked over time, fire investigators can assess how the fire progressed and use that information to backtrack to or near its point of origin.

Various embodiments provide data that may be useful in training and operating a fire detection neural network system. With the widespread network of FDS devices collecting all types of environmental conditions 24 hours a day, seven days a week, 365 days a year, a central service will be provided with an extensive data set that can be used to train the neural network system on normal environmental conditions, thereby providing a neural network that can quickly recognize abnormal conditions that may be associated with a fire event. For example, the collected data may be useful as a training set by a central server to learn what is or is not indicative of a fire, and reports that are likely false alarms versus real threats. This data set may also be used to train other FDS devices in the network that share similar environment characteristics, or servers in other networks deployed in locations that have some similar characteristics. As another benefit, even when some FDS devices are lost or damaged in a fire, meaningful information can be learned (e.g., how long it takes for FDS device to fail, characteristics of a certain species of tree/vegetation in relation to handling fire, how other things affect burning, such as size/age of tree, vegetation nearby, etc.). Thus, future FDS devices can learn characteristics of an oncoming fire sooner than they would otherwise through if-then rules or manual programming.

In various embodiments, FDS or CO detection devices may be configured for easy or rapid deployment using a variety of deployment methods. In some embodiments, FDS or CO detection devices may be lightweight and self-contained, which may enable many devices to be deployed by individuals walking through a forest or brush area, or emergency services personnel, e.g., responding to a fire or a fire and/or CO warning message. In some embodiments, FDS or CO detection devices (and/or sensors associated therewith) may be configured to be dropped, thrown, or otherwise placed by individuals or machines, such as to measure CO levels in a room, cave, mine or building before entering. In some embodiments, FDS devices may be configured for airdrop deployment to enable efficient and rapid deployment over a large area.

In some embodiments, FDS devices may be configured to be dropped from aircraft by integrating the components into lightweight and shock resistant packages that can survive a fall from altitude. In some embodiments, the FDS devices may be configured with a parachute for airdrop deployment. Airdrop deployment may be particularly suitable for low cost self-contained FDS devices that can be scattered over a wide area quickly and for low deployment cost. In some implementations, FDS devices configured for airdrop deployment may include a parachute and/or other structures configured to be captured by the branches of trees, thereby enabling treetop deployment without having to have technicians climb trees. Such embodiments may include a subset of potential sensors, including only those that can be integrated into a low cost, air-droppable configuration, such as thermal sensors, smoke detectors, $CO_2$ sensors, and microphones.

In some embodiments, FDSFDS or CO detection devices may be configured to be deployed during a fire event or response to a CO level warning to provide first responders (e.g., firefighters) with detailed and localized sensor information that may benefit firefighting or CO mitigation efforts. Such FDS or CO detection devices may be expendable and configured to withstand adverse temperature and/or chemical conditions to permit operating for as long as possible at or near a fire front. Some FDS devices may be configured with memory that is capable of withstanding high temperatures so that sensor data may be recorded and recovered after a fire has been controlled even if the FDS device or portions thereof is destroyed or damaged by the fire. Obtaining information within an ongoing fire may be useful for firefighting purposes as well as research into the dynamics of wildfires that may be useful for developing future firefighting techniques. For example, FDS devices configured for airdrop deployment dropped from aircraft around and/or into an ongoing fire to provide local environmental information that is useful by firefighters to anticipate the direction and speed of fire front. As another example, FDS devices may be configured in a package that can be thrown into or near a fire by firefighters in or near a hazardous environment, e.g., to obtain information from in, or closer to, the hazardous environment than is unsafe for an individual to approach or enter. As another example, FDS devices may be configured as projectiles that can be launched, individually or in groups, into or near a fire by a launching device, such as a mortar or catapult. As another example, FDS devices may be configured as low-cost UAVs that can fly into a fire and land or fall to earth if the air vehicle is disabled by the heat.

In some embodiments, FDS or CO detection devices may be configured to enter a configuration or installation mode upon initial deployment during which installers can enter information into memory for inclusion in fire and/or CO warning messages. For example, such information may include the device location (e.g., a street address or in device not equipped with a GNSS receiver), a specific location ("2nd floor," "master bedroom," etc.), instructions for accessing the area in which the FDS or CO detection device is deployed (e.g., "closest access is rear stairwell"), specific notes about the location (e.g., "warning: gas supply lines located nearby"), or any other suitable information. In some embodiments, FDS or CO detection devices may include a user interface for receiving such information. In some embodiments, FDS or CO detection devices may be configured to communicate with a mobile device (e.g., a smartphone, laptop computer, or specialized equipment) via wired or wireless (e.g., Bluetooth or Wi-Fi) communication links to receive such configuration and location information during an installation mode or procedure.

In some embodiments, each FDS or CO detection device may enter a high-power mode upon initial deployment to determine its location using global navigation satellite system (GNSS) receivers (e.g., a Global Positioning System (GPS receiver or the like and communicate its location and elevation information to a central server before entering a low power or sleep state as described herein. During such initial operations, the FDS or CO detection device may record and/or report readings from various sensors, such as to calibrate the sensors or obtain baseline sensor information. As noted above, initial operations may also include forming a wireless mesh network with other FDS or CO detection devices within a wireless communication range. Initial operations may also include receiving OTA updates of latest software versions and operating data. Other initial operations are also possible.

In some embodiments, some or all of the FDS devices may be configured as a central node that may be deployed by technicians in a location that permits charging/recharging of the battery power unit(s) by a wind generator and/or solar cells, while various sensor modules may be deployed nearby in locations that provide better sensing perspectives for each sensor. In such embodiments, the sensor modules may communicate data via wireless communications, such as BLE links, enabling the sensor modules to be deployed some distance from the central node FDS device. For example, smoke sensors and wind speed and direction sensors may be deployed in trees or on elevated platforms so as to sample the air at or near treetop level. As another example, thermal sensors may be deployed in a perimeter surrounding the central node FDS device at ground level and treetop level to provide a more complete measure of temperatures as well as providing a temperature profile of the area. As a further example, an omnidirectional visible light and/or IR camera module may be positioned on a tree top or tower that provides a wide vista, communicating image or thermal information to the central node FDS device via wireless communication links. Such embodiments may have advantages in enabling the use of very low-cost sensors that can be deployed in locations that optimize sensor capabilities, while enabling a more capable central node FDS device to be positioned where a wind generator can be exposed to the wind and/or solar cells can receive solar energy and/or be serviced occasionally. Also, such embodiments enable sensors to be added or replaced without the need to change or physically update the central node FDS device, which can be upgraded simply through over-the-air updates as described herein.

Thus, various embodiments improve the operations of FDS or CO detection devices and systems by providing rapid detection of potential fire conditions and fire events, to detect a fire while it is incipient or at a very early stage, and/or providing notifications of monoxide detections, as well as to provide information useful for fire and/or carbon monoxide hazard mitigation and suppression. Various embodiments improve the operations of FDS or CO detection sensors and systems by providing a pinpoint coordinate location or locations of potential fire conditions and fire events and/or carbon monoxide. Further, the FDS or CO detection sensors and systems may utilize a wireless backhaul and lightweight machine communications, such as LwM2M, to enable the widespread inexpensive deployment of numerous FDS or CO detection devices.

Figure 1B:
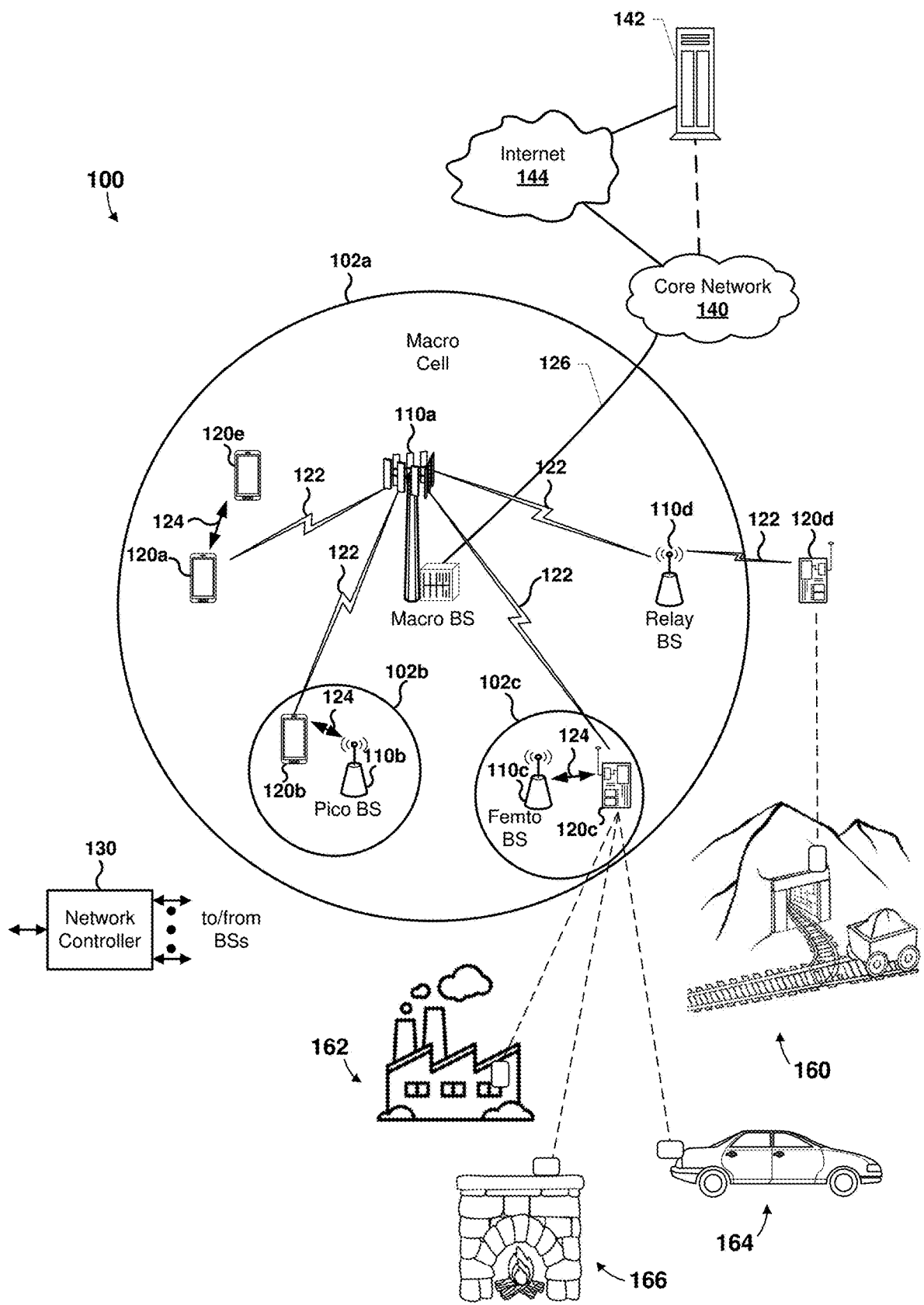

FIG. 1 illustrates an example wireless network 100 suitable for use with various embodiments. The wireless network 100 includes a number of base stations 110a-110d and other network entities. Some base stations (e.g., 110a) may be connected to a core network 140, such as by wired communication link 126, and the core network may provide access (e.g., via Internet protocol communications) to a remote server 142 that provides emergency services through direct communication links 144 and/or via an intermediate network, such as the Internet 144. The base stations 110a-110d may provide access to the wireless network 100 to a variety of wireless devices 120a-120e (for example, mobile communication device 120a, 120b, and 120e, and FDS or CO detection devices 120c and 120d) via wireless communication links 122. Each base station 110a-110d may provide communication coverage for a particular geographic area. In the 3rd Generation Partnership Project (3GPP), the term "cell" may refer to a coverage area of a Node B and/or a Node B subsystem serving this coverage area, depending on the context in which the term is used. In new radio (NR) or Fifth Generation (5G) network systems, the term "cell" and eNB, Node B, 5G NB, access point (AP), NR base station, NR base station, or transmission and reception point (TRP) may be interchangeable. In some examples, a cell may not necessarily be stationary, and the geographic area of the cell may move according to the location of a mobile base station. In some embodiments, the base stations 110a-110d may be interconnected to one another and/or to one or more other base stations or network nodes (not shown) in the wireless network 100 through various types of backhaul interfaces such as a direct physical connection, a virtual network, or the like using any suitable transport network.

In general, any number of wireless networks may be deployed in a given geographic area. Each wireless network may support one or more RATs and may operate on one or more frequencies. A frequency may also be referred to as a carrier, a frequency channel, a frequency band, etc. Each frequency may support a single radio access technology (RAT) in a given geographic area in order to avoid interference between wireless networks of different RATs. The wireless network 100 supporting FDS or CO detection device communications may use or support a number of different RATs in wireless communication links 122 or 124, including for example, LTE/Cat. M, NB-IoT, Global System for Mobile Communications (GSM), and Voice over Long Term Evolution (VoLTE) RATs as well as other RATs (e.g., 5G). The wireless network 100 may use a different access point name (APN) for each different RAT.

A base station 110a-110d may provide communication coverage for a variety of cell types, such as a macro cell 102a, a pico cell 102b, a femto cell 102c, and/or other types of cells via wireless communication links 124. A macro cell (e.g., 102a) may cover a relatively large geographic area (e.g., several kilometers in radius) and may allow unrestricted access by wireless devices with a service subscription. A pico cell (e.g., 102b) may cover a relatively small geographic area and may allow unrestricted access by wireless devices with service subscription. A femto cell (e.g., 102c) may cover a relatively small geographic area (e.g., a home) and may allow restricted access by wireless devices having association with the femto cell (e.g., wireless devices in a Closed Subscriber Group (CSG), wireless devices for users in a home, etc.). A base station for a macro cell may be referred to as a macro base station (e.g., 110a). A base station for a pico cell may be referred to as a pico base station (e.g., 110b). A base station for a femto cell 102c may be referred to as a femto base station or a home base station (e.g., 110c). In the example shown in FIG. 1, the base stations 110a, 110b and 110c may be macro base stations for the macro cells 102a, 102b and 102c, respectively. A base station may support one or multiple cells. Further, base stations may support communication links 124 on multiple networks using multiple RATs, such as Cat.-M1, NB-IoT, GSM, and VoLTE.

The wireless network 100 may also include relay stations (e.g., 110d). A relay station is a station that receives a transmission of data and/or other information from an upstream station (e.g., a base station or an IoT device) and sends a transmission of the data and/or other information to a downstream station (e.g., an IoT device or a base station). A relay station may also be a wireless device that relays transmissions for other wireless devices including IoT devices. In the example shown in FIG. 1, the relay station 110d may communicate with the base station 110a and the wireless device 120d in order to facilitate communication between the base station 110a and the wireless device 120d. A relay station may also be referred to as a relay base station, a relay, etc. Further, relay stations may support communications on multiple networks using multiple RATs, such as Cat.-M1, NB-IoT, GSM, and VoLTE.

The wireless network 100 may be a heterogeneous network that includes base stations of different types, e.g., macro base station, pico base station, femto base station, relays, etc. These different types of base stations may have different transmit power levels, different coverage areas, and different impact on interference in the wireless network 100. For example, macro base station may have a high transmit power level (e.g., 20 watts) whereas pico base station, femto base station, and relays may have a lower transmit power level (e.g., 1 watt).

The wireless network 100 may support synchronous or asynchronous operation. For synchronous operation, the base stations 110a-110d may have similar frame timing, and transmissions from different base stations may be approximately aligned in time. For asynchronous operation, the base stations 110a-110d may have different frame timing, and transmissions from different base stations may not be aligned in time. The techniques described herein may be used for both synchronous and asynchronous operations.

A network controller 130 may be coupled to a set of base stations (e.g., 110a-110d) and provide coordination and control for these base stations. The network controller 130 may communicate with the base stations 110a-110d via a wired or wireless backhaul communication link. The base stations 110a-110d may also communicate with one another, e.g., directly or indirectly via a wireless or wired backhaul communication link.

In various embodiments, FDS or CO detection devices (e.g., 120c and 120d) may be configured to detect potential or actual fire events (e.g., fire 155) and/or high levels of CO and report information to a remote server 142 providing fire detection system services via the wireless network 100. Similarly, the remote server 142 may be configured to receive fire event reports and sensor data from several FDS or CO detection devices (e.g., 120c and 120d) as well as provide command signals (e.g., to wake up, activate certain sensors, report data, move, and/or shutdown or go into a low-power mode or other mode). In some embodiments a server providing fire detection system services may be deployed as or included within the functionality of a network element (e.g., a server coupled to a macro base station 110a).

FDS devices may be dispersed throughout the wireless network 100. In some embodiments, the FDS devices may be deployed in a deployment area, such as a forest 160, or any other area, including any natural area or environment, any rural, suburban, or urban environment, any industrial, commercial, or residential building, or any other suitable environment. Some FDSFDS or CO detection devices may be dispersed throughout the wireless network 100. In some embodiments, the FDS or CO detection devices may be deployed in any industrial, commercial, or residential building, or any other suitable environment, such as a mine 160, an industrial facility 162, or any other location or area subject to a risk of carbon monoxide generation or accumulation, such as a room in a home, a parking garage, a construction site, a power plant, any factory, manufacturing facility, or fabrication facility, an office, a store, a designated smoking area, a bus stop, a truck loading facility, or any other suitable location or any other suitable area where carbon monoxide may accumulate.

In some embodiments, a FDS or CO detection device may be deployed in an outdoor area subject to a risk of fire, such as a forest, brush area, or another suitable location. In some embodiments, a FDS or CO detection device may be attached to or incorporated into a vehicle such as a car 164 or any other motor vehicle (e.g., a boat, a motorcycle, etc.). In some embodiments, a FDS or CO detection device may be deployed in, on, or near any machine, appliance, system, or location subject to carbon monoxide generation, or a carbon monoxide leak. A fireplace 166 is illustrated for conciseness, but other examples include a building heating system, a hot water heater, an HVAC (heating, ventilation, and cooling) system, a stove, a furnace, a gas or charcoal grill, or any other suitable appliance or system; a tool such as a lawnmower, a generator, a snowblower, a leaf blower, a wire trimmer, or any other tool that operates using an engine. Some FDS or CO detection devices may include evolved or machine-type communication (MTC) devices or evolved MTC (eMTC) IoT devices. MTC and eMTC IoT devices include, for example, robots, drones, remote devices, sensors, meters, monitors, location tags, etc., that may communicate with a base station, another device (e.g., remote device), or some other entity.

Certain wireless networks (e.g., LTE) utilize orthogonal frequency division multiplexing (OFDM) on the downlink and single-carrier frequency division multiplexing (SC-FDM) on the uplink. OFDM and SC-FDM partition the system bandwidth into multiple (K) orthogonal subcarriers, which are also commonly referred to as tones, bins, etc. Each subcarrier may be modulated with data. In general, modulation symbols are sent in the frequency domain with OFDM and in the time domain with SC-FDM. The spacing between adjacent subcarriers may be fixed, and the total number of subcarriers (K) may be dependent on the system bandwidth. For example, the spacing of the subcarriers may be 15 kHz and the minimum resource allocation (called a "resource block") may be 12 subcarriers (or 180 kHz). Consequently, the nominal full frame transfer (FFT) size may be equal to 128, 256, 512, 1024 or 2048 for system bandwidth of 1.25, 2.5, 5, 10 or 20 megahertz (MHz), respectively. The system bandwidth may also be partitioned into subbands. For example, a subband may cover 1.08 MHz (i.e., 6 resource blocks), and there may be 1, 2, 4, 8 or 16 subbands for system bandwidth of 1.25, 2.5, 5, 10 or 20 MHz, respectively.

A NR base station (e.g., eNB, 5G Node B, Node B, transmission and reception point (TRP), access point (AP)) may correspond to one or multiple base stations. NR cells may be configured as access cell (ACells) or data only cells (DCells). For example, the radio access network (RAN) (e.g., a central unit or distributed unit) may configure the cells. DCells may be cells used for carrier aggregation or dual connectivity, but not used for initial access, cell selection/reselection, or handover. NR base stations may transmit downlink signals to IoT devices indicating the cell type. Based on the cell type indication, the IoT device may communicate with the NR base station. For example, the IoT device may determine NR base stations to consider for cell selection, access, handover (HO), and/or measurement based on the indicated cell type.

Figure 2A:
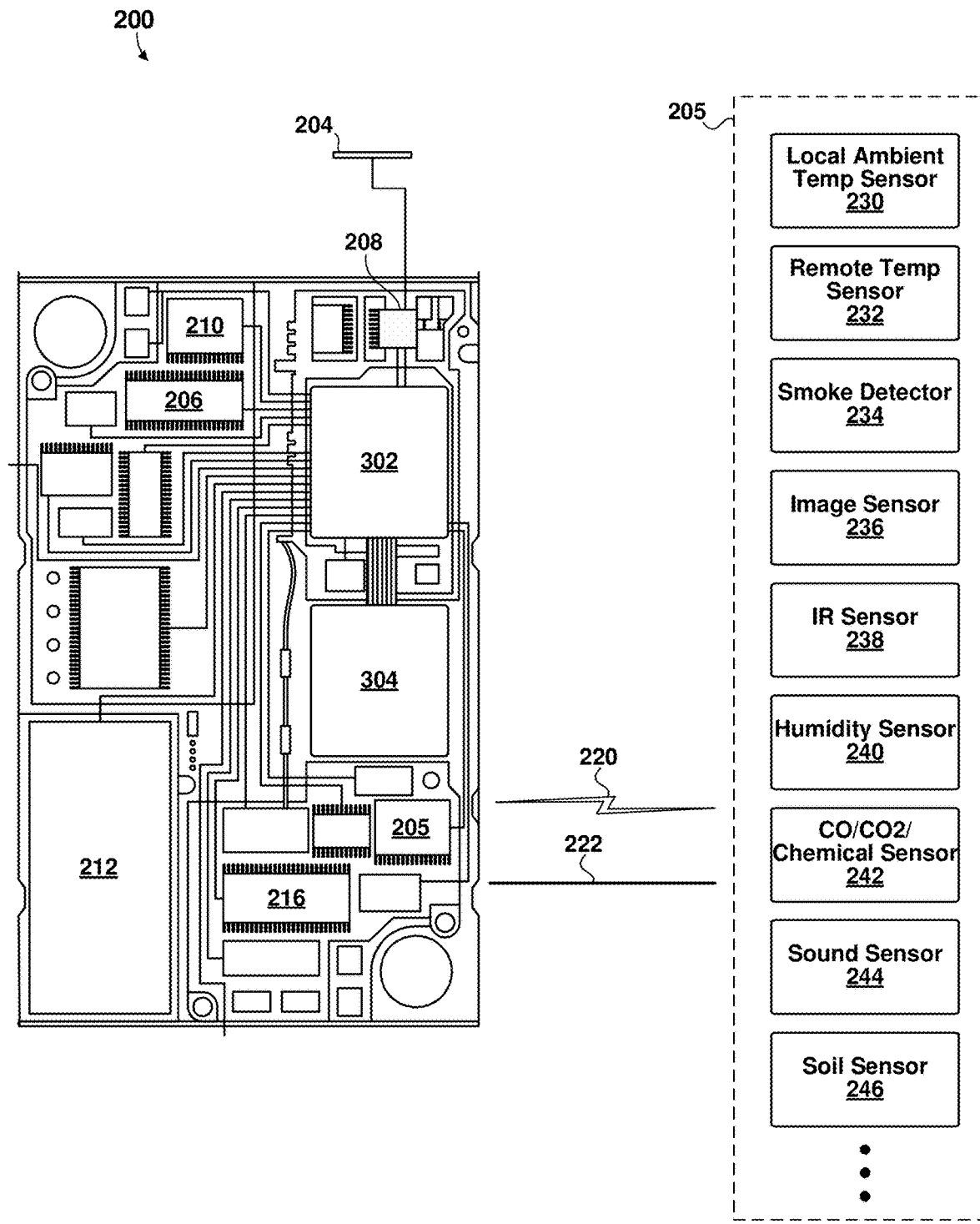
FIGS. 2A and 2B are component block diagrams of a FDS or CO detection device suitable for use with various embodiments.

FIG. 2A is a component block diagram of an FDS or CO detection device 200 (e.g., 120c, 120d) suitable for use with various embodiments. With reference to FIGS. 1 and 2, various embodiments may be implemented on a variety of FDS or CO detection devices, which may include at least the elements illustrated in FIG. 2. The FDS or CO detection device 200 may include a first SOC 302 (e.g., a SOC-CPU) coupled to a second SOC 304 (e.g., a 5G capable SOC), as further described below. The first and second SOCs 302, 304 may be coupled to internal memory 206. The FDS or CO detection device 200 may include or be coupled to an antenna 204 for sending and receiving wireless signals from a cellular telephone transceiver 208 or within the second SOC 304. The antenna 204 and transceiver 208 and/or second SOC 304 may support communications using various RATs, including Cat.-M1, NB-IoT, CIoT, GSM, and/or VoLTE. In some embodiments, the FDS or CO detection device 200 may also include a sound encoding/decoding (CODEC) circuit 210, which digitizes sound received from a microphone into data packets suitable for wireless transmission and decodes received sound data packets to generate analog signals that are provided to a speaker to generate sound in support of voice or VoLTE calls. In some embodiments, one or more of the processors in the first and second SOCs 302, 304, one or more wireless transceivers 208 and CODEC 210 may include a digital signal processor (DSP) circuit (not shown separately). The FDS or CO detection device 200 may include an internal power source, such as a battery power unit 212 or units configured to power the SOCs and transceiver(s) 208. Such FDS or CO detection devices may include power management components 216 to manage charging of the battery power unit 212. In some embodiments, the power management components 216 may be included or configured as part of the battery power unit(s) 212.

The SOC 302 and/or 304 may include, be coupled to include, and/or may communicate with, one or more fire and/or CO sensors. In some embodiments, one or more of the fire and/or CO sensors may be included in the FDS or CO detection device 200 and may communicate with the SOC 302 and/or 304 via a communication bus 205. In some embodiments, one or more of the sensors may be external to the FDS or CO detection device 200 (e.g., external to a housing of the FDS or CO detection device 200, such on the on the exterior of the housing or separate from the housing) and may communicate with the SOC 302 and/or 304 via a wired communication link 222. In some embodiments, one or more of the sensors may be external to the FDS or CO detection device 200 (e.g., external to a housing of the FDS or CO detection device 200, such on the on the exterior of the housing or separate from the housing) and may communicate with the SOC 302 and/or 304 via a wireless communication link 220. In some embodiments, the FDS or CO detection device 200 may include a communication port 205 that may support the wired communication link 222. The communication port 205 may support communications with the one or more remote fire and/or CO sensor(s) and/or other types of sensors using, for example, Ethernet, a National Instruments 9205-type connection, or another suitable physical connection. Any number of such sensors and/or other sensors of any type may be included in different implementations of the FDS or CO detection device 200.

The sensors may include (but is not limited to) a variety of sensors including a local ambient temperature sensor 230 (i.e., a sensor for detecting a temperature outside of the FDS device), a remote temperature sensor 232, a smoke detector 234, an image sensor 236, an infrared sensor 238, an ambient humidity sensor 240, a chemical sensor 242 such as a carbon monoxide (CO) sensor, a carbon dioxide (CO2) sensor, and/or another chemical sensor, a sound sensor 244 (such as a microphone), a soil sensor 246, and other sensors or sensing devices, including any combination of the foregoing. It should be clear that any number of these (and/or other) sensors may be included in different implementations of the FDS device 200.

Figure 2B:
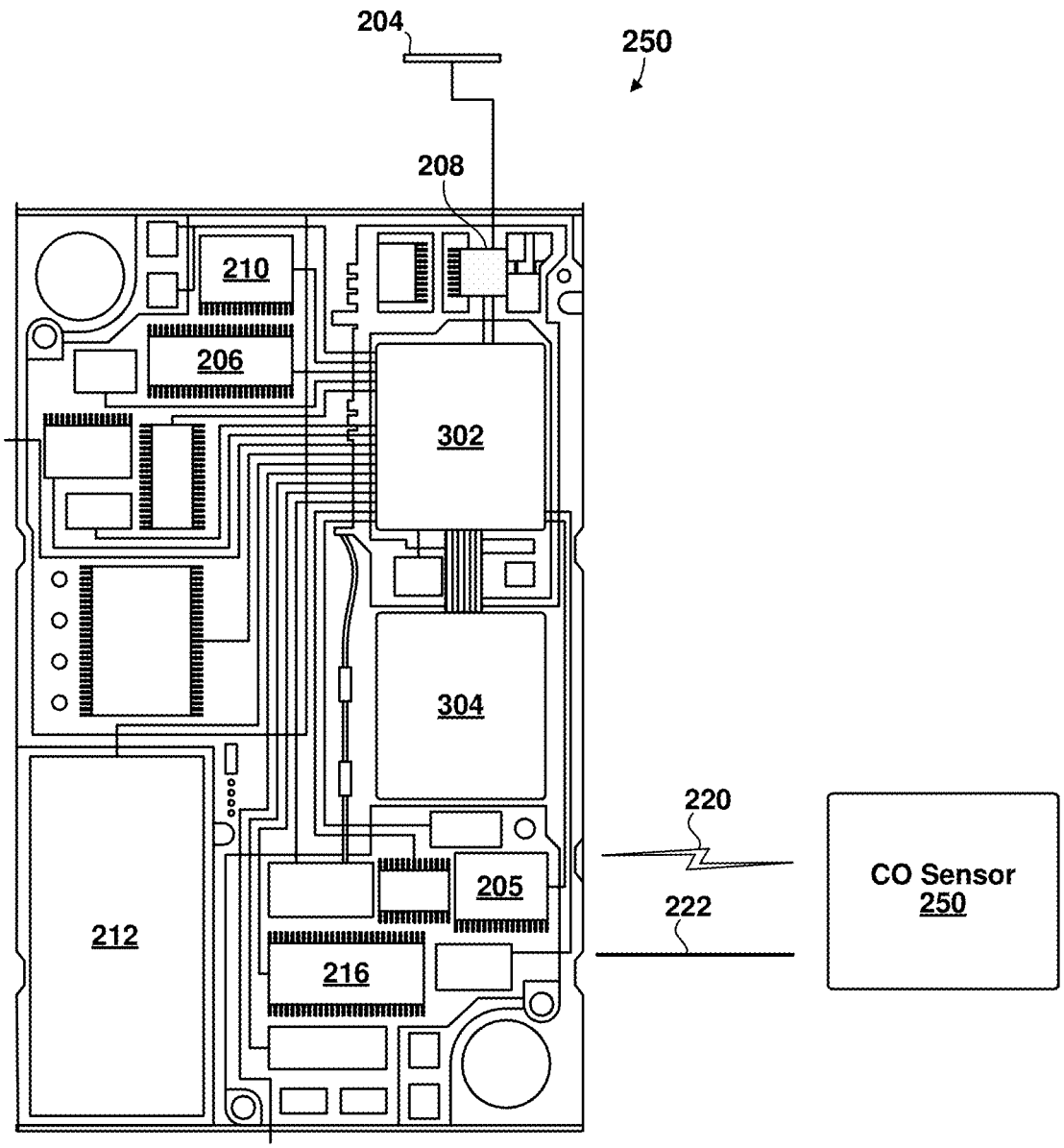

FIG. 2B is a component block diagram of a CO detection device 250 (e.g., 120c, 120d) suitable for use with various embodiments. With reference to FIGS. 1 and 2, various embodiments may be implemented on a variety of CO detection devices, which may include at least the elements illustrated in FIG. 2. The CO detection device 250 may include a first SOC 302 (e.g., a SOC-CPU) coupled to a second SOC 304 (e.g., a 5G capable SOC), as further described below. The first and second SOCs 302, 304 may be coupled to internal memory 206. The CO detection device 250 may include or be coupled to an antenna 204 for sending and receiving wireless signals from a cellular telephone transceiver 208 or within the second SOC 304. The antenna 204 and transceiver 208 and/or second SOC 304 may support communications using various RATs, including Cat.-M1, NB-IoT, CIoT, GSM, and/or VoLTE. In some embodiments, the CO detection device 250 may also include a sound encoding/decoding (CODEC) circuit 210, which digitizes sound received from a microphone into data packets suitable for wireless transmission and decodes received sound data packets to generate analog signals that are provided to a speaker to generate sound in support of voice or VoLTE calls. In some embodiments, one or more of the processors in the first and second SOCs 302, 304, one or more wireless transceivers 208 and CODEC 210 may include a digital signal processor (DSP) circuit (not shown separately). The CO detection device 250 may include an internal power source, such as a battery power unit 212 or units configured to power the SOCs and transceiver(s) 208. Such CO detection devices 250 may include power management components 216 to manage charging of the battery power unit 212. In some embodiments, the power management components 216 may be included or configured as part of the battery power unit(s) 212.

The SOC 302 and/or 304 may include, be coupled to include, and/or may communicate with, one or more CO sensors 252. In some embodiments, one or more of the CO sensors 252 may be included in the CO detection device 250 and may communicate with the SOC 302 and/or 304 (FIG. 3) via a communication bus (not shown). In some embodiments, one or more of the sensors 252 may be external to the CO detection device 250 (e.g., external to a housing of the CO detection device 250, such on the on the exterior of the housing or separate from the housing) and may communicate with the SOC 302 and/or 304 via a wired communication link 222. In some embodiments, one or more of the CO sensors 252 may be external to the CO detection device 250 (e.g., external to a housing of the CO detection device 250, such on the on the exterior of the housing or separate from the housing) and may communicate with the SOC 302 and/or 304 via a wireless communication link 220. In some embodiments, the CO detection device 250 may include a communication port 205 that may support the wired communication link 222. The communication port 205 may support communications with the one or more remote CO sensor(s) and/or other types of sensors using, for example, Ethernet, a National Instruments 9205-type connection, or another suitable physical connection. Any number of such CO sensors 252 and/or other sensors of any type may be included in different implementations of the CO detection device 252.

Figure 3:
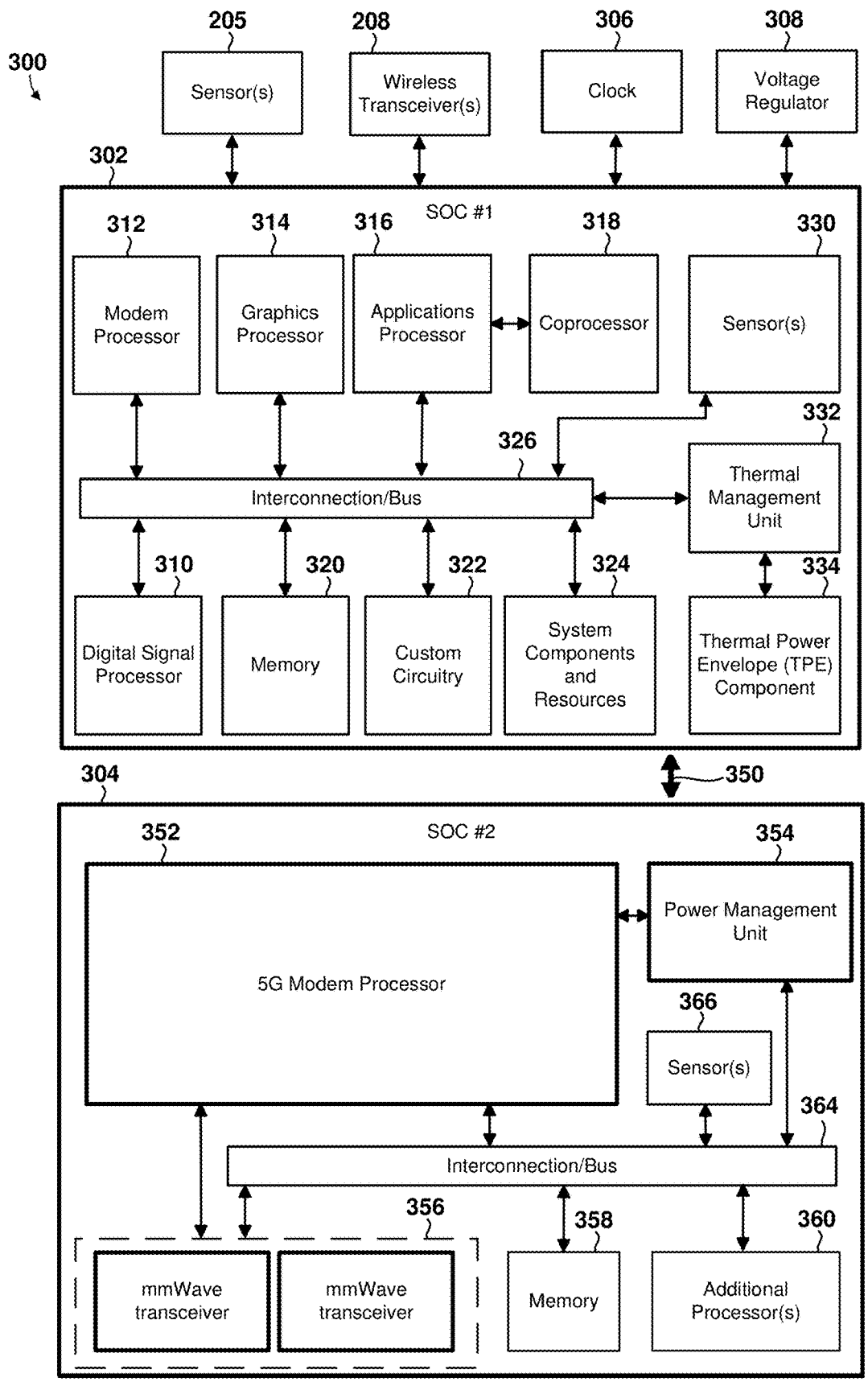
FIG. 3 is a component block diagram illustrating components of example a FDS or CO detection device suitable for implementing various embodiments.

FIG. 3 is a component block diagram illustrating components of an example SIP 300 suitable for implementing various embodiments. With reference to FIGS. 1-3, various embodiments may be implemented on FDS or CO detection devices (e.g., 120c, 120d, 200) equipped with any of a number of single processor and multiprocessor computer systems, including a system-on-chip (SOC) or system in a package (SIP) that may include at least the components illustrated in FIG. 3. In some embodiments, the SIP 300 may provide all of the processing, data storage and communication capabilities required to support the mission or functionality of a given FDS or CO detection device. The same SIP 300 may be used in a variety of different types of FDS or CO detection devices with device-specific functionality provided via programming of one or more processors within the SIP 300. Further, the SIP 300 is an example of components that may be implemented in a SIP used in FDS or CO detection devices and more or fewer components may be included in a SIP used in FDS or CO detection devices without departing from the scope of the claims. For example, an FDS or CO detection device equipped with the SIP 300 may include a 5G modem processor that is configured to send and receive information via the wireless network 100.

The example SIP 300 includes two SOCs 302, 304 coupled to a clock 306, a voltage regulator 308, various sensors and one or more wireless transceivers 208. The SOC 302 may include one or more sensors 330 (e.g., temperature, voltage, current, etc.), and may communicate with one or more CO sensors 252. In some embodiments, the first SOC 302 may operate as a central processing unit (CPU) of the FDS or CO detection device that carries out the instructions of software application programs by performing the arithmetic, logical, control and input/output (I/O) operations specified by the instructions. In some embodiments, the second SOC 304 may operate as a specialized processing unit. For example, the second SOC 304 may operate as a specialized 5G processing unit responsible for managing high volume, high speed (e.g., 5 Gbps, etc.), and/or very high frequency short wave length (e.g., 28 GHz mmWave spectrum, etc.) communications.

The first SOC 302 may include a digital signal processor (DSP) 310, a modem processor 312, a graphics processor 314, an application processor 316, one or more coprocessors 318 (e.g., vector co-processor) connected to one or more of the processors, memory 320, custom circuitry 322, system components and resources 324, an interconnection/bus module 326, a thermal management unit 332, and a thermal power envelope (TPE) component 334. The second SOC 304 may include a 5G modem processor 352, a power management unit 354 (which may include one or more temperature sensors), an interconnection/bus module 364, a plurality of mmWave transceivers 356, memory 358, various additional processors 360, such as an applications processor, packet processor, etc., and one or more internal sensors 366 (e.g., accelerometers for sensing the gravity gradient, internal temperature sensors, etc.).

Each processor 310, 312, 314, 316, 318, 352, 360 may include one or more cores, and each processor/core may perform operations independent of the other processors/cores. For example, the first SOC 302 may include a processor that executes a first type of operating system (e.g., FreeBSD, LINUX, OS X, etc.) and a processor that executes a second type of operating system (e.g., Microsoft Windows 10). In addition, any or all of the processors 310, 312, 314, 316, 318, 352, 360 may be included as part of a processor cluster architecture (e.g., a synchronous processor cluster architecture, an asynchronous or heterogeneous processor cluster architecture, etc.).

The first and second SOC 302, 304 may include various system components, resources and custom circuitry for managing sensor data, analog-to-digital conversions, wireless data transmissions, and for performing other specialized operations, such as decoding data packets and processing encoded audio and video signals for rendering in a web browser. For example, the system components and resources 324 of the first SOC 302 may include power amplifiers, voltage regulators, oscillators, phase-locked loops, peripheral bridges, data controllers, memory controllers, system controllers, access ports, timers, and other similar components used to support the processors and software clients running on an IoT device. The system components and resources 324 and/or custom circuitry 322 may also include circuitry to interface with peripheral devices, such as cameras, electronic displays, wireless communication devices, external memory chips, etc.

The first and second SOC 302, 304 may communicate via an interconnection/bus module 350. The various processors 310, 312, 314, 316, 318, may be interconnected to one or more memory elements 320, system components and resources 324, and custom circuitry 322, and thermal management unit 332 via an interconnection/bus module 326. Similarly, the processors 352, 360 may be interconnected to the power management unit 354, the mmWave transceivers 356, memory 358, and various additional processors 360 via the interconnection/bus module 364. The interconnection/bus module 326, 350, 364 may include an array of reconfigurable logic gates and/or implement a bus architecture (e.g., CoreConnect, AMBA, etc.). Communications may be provided by advanced interconnects, such as high-performance networks-on chip (NoCs).

The first and/or second SOCs 302, 304 may further include an input/output module (not illustrated) for communicating with resources external to the SOC, such as a clock 306, the voltage regulator 308, sensors and wireless transceiver(s) 208. The resources external to the SOC (e.g., clock 306, voltage regulator 308, sensor(s), and wireless transceiver(s) 208) may be shared by two or more of the internal SOC processors/cores.

Figure 4:
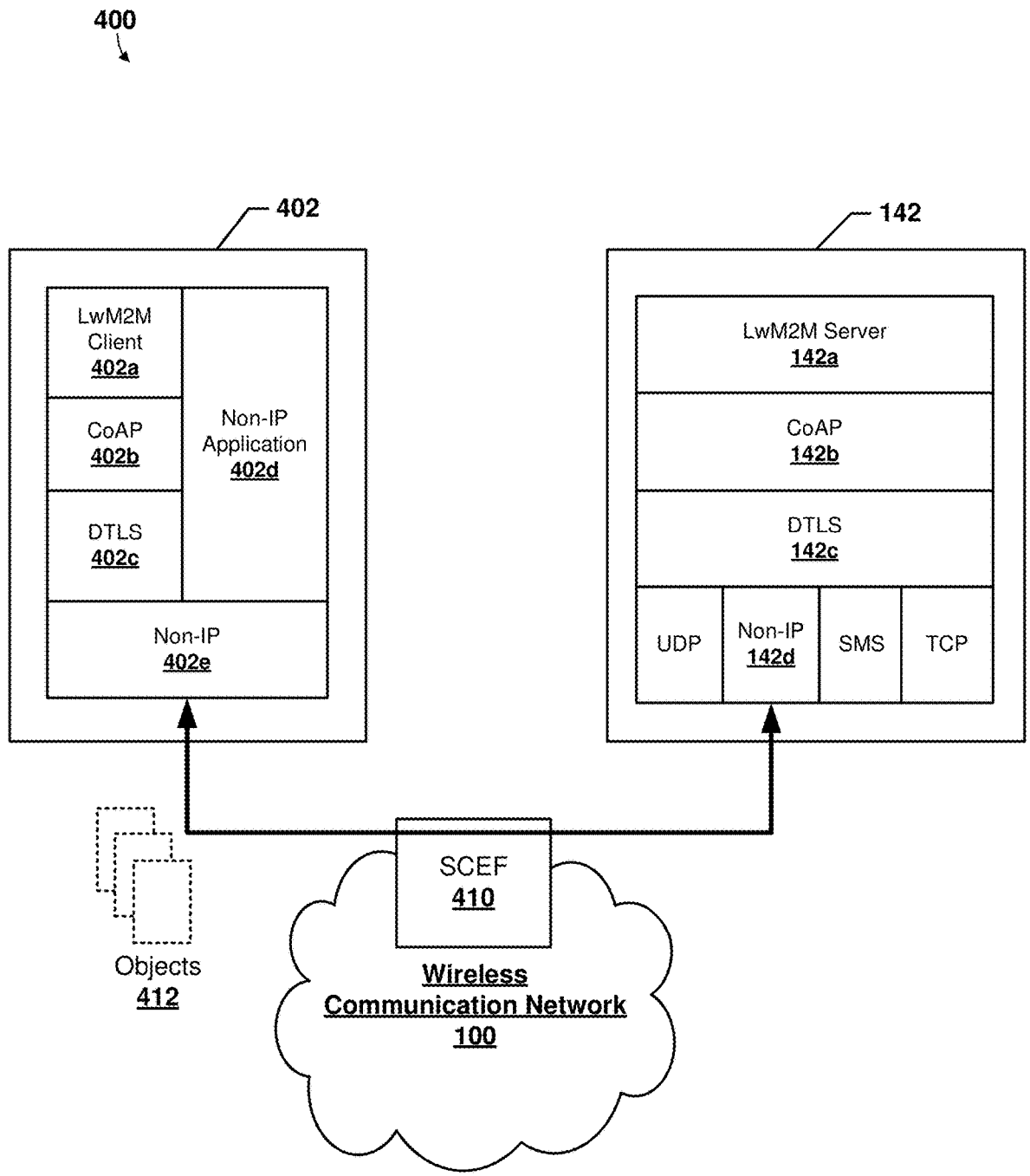
FIG. 4 is a block diagram illustrating an example Non-IP Data Delivery (NIDD) data call architecture suitable for use with various embodiments.

FIG. 4 illustrates an example Non-IP Data Delivery (NIDD) data call architecture 400 suitable for use with various embodiments. With reference to FIGS. 1-4, the architecture 400 shows an example of a NIDD data call between an FDS or CO detection device 402 (e.g., FDS or CO detection devices 120c, 120d, 200, 300) and a server 142. The architecture 400 is discussed with reference to LwM2M, but LwM2M is merely an example of an application of a NIDD data call used to illustrate aspects of the architecture 400. Other protocols, such as other OMA protocols or the like may be used to establish a NIDD data call and the architecture 400 may apply to non-LwM2M NIDD data calls. The FDSFDS or CO detection device 402 and the server 142 may be configured to communicate using NIDD. As an example, the FDSFDS or CO detection device 402 may be a LwM2M client device. As an example, the server 142 may include a LwM2M server 142a, such as a bootstrap server as defined by LwM2M or an LwM2M server that is not a bootstrap server. In some embodiments, the server 142 may be an application server.

A Service Capability Exposure Function (SCEF) 410 enables NIDD communication between the FDSFDS or CO detection device 402 and the server 142. The SCEF 410 enables devices such as the FDSFDS or CO detection device 402 and the application server 142 to access certain communication services and capabilities, including NIDD. The SCEF 410 may support a raw data download (RDD) service. While illustrated as in communication with one server 142, the SCEF 410 may route traffic to multiple servers each identified by their own respective destination port when using the RDS (Reliable Data Service) protocol. In this manner, a single NIDD data call through the SCEF 410 may include multiplexed traffic intended for multiple different destinations.

In some embodiments, the FDSFDS or CO detection device 402 may be configured with an LwM2M client 402a that uses the LwM2M device management protocol. The LwM2M device management protocol defines an extensible resource and data model. The LwM2M client 402a may employ a service-layer transfer protocol such as Constrained Application Protocol (CoAP) 402b to enable, among other things reliable and low overhead transfer of data. The FDSFDS or CO detection device 402 may employ a communication security protocol such as Datagram Transport Layer Security (DTLS) 402c. DTLS in particular may provide security for datagram-based applications. One such application may be a Non-IP Application 402d. The Non-IP Application 402d may utilize a non-IP protocol 402e to structure non-IP communications.

In some embodiments, the server 142 may be configured with the LwM2M server 142a, a transfer protocol such as CoAP 142b, and a security protocol such as DTLS 142c. The application server 142 may be configured to utilize a variety of communication protocols, such as non-IP protocol 142d, as well as other communication protocol such as UDP, SMS, TCP, and the like.

As an example, the FDSFDS or CO detection device 402 may be configured as a unitary device powered by battery power unit 212, and may be configured for an operational life of months or years. Typical protocols for establishing Internet protocol (IP) data bearers are generally power hungry. In contrast, NIDD may enable the FDSFDS or CO detection device 402 to communicate small amounts of data by a control plane, rather than a user plane, without the use of an IP stack. NIDD may have particular application in Cat.-M1, NB-IoT and CIoT communications to enable constrained devices to communicate via a cellular network and send or receive small amounts of data per communication (e.g., in some cases, on the order of hundreds of bytes, tens of bytes, or smaller). NIDD may enable the FDSFDS or CO detection device 402 to embed a small amount of data in a container or object 412 without use of an IP stack, and to send the container or object 412 to the server 142 via the SCEF 410. Similarly, the FDSFDS or CO detection device 402 may receive containers or objects 412 that define services and capabilities of the network 100 the FDSFDS or CO detection device 402 may be connected to enable the FDSFDS or CO detection device 402 to reach the SCEF 410 and server 142. For example, such containers or objects 412 that define services and capabilities may include various OMA objects, such as an APN connection profile object (Object ID 11), a LwM2M server object (Object ID 1), a LwM2M security object (Object ID 0), etc.

In some embodiments, the FDSFDS or CO detection device 402 may support RDS in a NIDD data call. The FDSFDS or CO detection device 402 may multiplex uplink traffic for different servers 142 by sending the uplink traffic with a pair of source and destination port numbers and an Evolved Packet System (EPS) bearer ID. The SCEF 410 may receive uplink traffic from the FDSFDS or CO detection device 402 and may route the uplink traffic to the appropriate server, such as server 142 or any other server, based on the destination port number indicated for the uplink traffic.

FIGS. 5A and 5B illustrate aspects of an example fire alarm object 500a, 500b according to various embodiments. Although the fire alarm object 500a, 500b is discussed in view of the LwM2M standard, any suitable object or arrangement of information may be used in various embodiments.

With reference to FIGS. 1-5B, as noted above, NIDD may enable the FDS device (e.g., 120c, 120d, 200, 300, 402) to embed a small amount of data in a container or object without use of an IP stack, and to send the container or object to a server (e.g., 142). By using object(s) with defined resources, an FDS device may construct a message using index references to resource definitions with a very small amount of data that conveys complex and varied information to a receiving device (e.g., a server). For example, the fire alarm object 500a, 500b may include resources that may be indexed, for example, by a Resource Definition ID (such as Resource Definition IDs 1-29).

Each resource definition may include a name, and an indicator of an operation on or for the resource (e.g., a permissible operation), such as Read (R), Read-Write (RW), or Execute (E), or other operations (as may be, for example, defined in the LwM2M standard). Each resource definition may also include a permitted number of instances (e.g., "single") of the resource, whether an operation is Mandatory or Optional, and a data type where applicable. A data type may include, for example, Boolean, Float, String, or Integer for certain data types, or none for executable commands (e.g., Resource Definition ID 11 "Reset"). Each resource definition may also include a permitted range or enumeration of the relevant information for that resource (e.g., −70°–150° C. or −94°–302° F.; 0-100; etc.) and permissible units (e.g., ° C., ° F., decibels (dB), percentage, etc.). Each resource definition may also include a description of the meaning of a value or values associated with each resource definition. For example, a value associated with Resource Definition ID 3 will be interpreted to indicate a "Last or Current Measured Value from the Sensor", or if the value is zero, that a temperature sensor is not integrated into the FDS device. As another example, a value associated with Resource Definition ID 2 will be interpreted to indicate a temperature provided by a wireless communication network for the area around the FDS device ("Temperature received from web for the area").

FIGS. 5C and 5D illustrate aspects of an example fire alarm object 500c, 500d according to various embodiments. Although the fire alarm object 500c, 500d is discussed in view of the LwM2M standard, any suitable object or arrangement of information may be used in various embodiments.

With reference to FIGS. 1-5D, as noted above, NIDD may enable the FDS device (e.g., 120c, 120d, 200, 300, 402) to embed a small amount of data in a container or object without use of an IP stack, and to send the container or object to a server (e.g., 142). By using object(s) with defined resources, an FDS device may construct a message using index references to resource definitions with a very small amount of data that conveys complex and varied information to a receiving device (e.g., a server). For example, the fire alarm object 500c, 500d may include resources that may be indexed, for example, by a Resource Definition ID (such as Resource Definition IDs 0-33, 6044, 5514, 5515, and 6039).

Each resource definition may include a name, and an indicator of an operation on or for (e.g., a permissible operation), such as Read (R), Read-Write (RW), or Execute (E), or other operations (e.g., as may be defined in the LwM2M standard). Each resource definition may also include a permitted number of instances (e.g., "single") of the resource, whether an operation is Mandatory or Optional, and a data type where applicable. A data type may include, for example, Boolean, Float, String, or Integer for certain data types, or none for executable commands (e.g., Resource Definition ID 12 "Reset Temperature"). Each resource definition may also include a permitted range or enumeration of the relevant information for that resource (e.g., 0.0-100.0 in the case of Resource IDs 15, 16, 17, 18, 19, 20, and 6044) as well as permissible units (e.g., decibels (dB), parts per million (ppm), meters (m), and/or other suitable units).

Each resource definition may also include a description of the meaning of a value or values associated with each resource definition. For example, an integer value associated with Resource Definition ID 1 will be interpreted to indicate temperature units, such as "0=Celsius, 1=Fahrenheit, 2=Kelvin." As another example, a value associated with Resource Definition ID 2 will be interpreted to indicate a "Temperature of the area," e.g., around the FDS device. As another example, a value associated with Resource Definition ID 2 will be interpreted to indicate a "Last or Current Measured Value from the Sensor," and further that a value of 65534 indicates that sensor data is not available (e.g., because the FDS device is not configured with a temperature sensor).

FIG. 5E illustrates aspects of an example fire and/or CO alarm object 500e (illustrated in FIG. 5E as a CO Detector Object) according to various embodiments. Although the fire and/or CO alarm object 500e is discussed in view of the LwM2M standard, any suitable object or arrangement of information may be used in various embodiments.

With reference to FIGS. 1-5E, as noted above, NIDD may enable the FDS or CO detection device (e.g., 120c, 120d, 200, 300, 402) to embed a small amount of data in a container or object without use of an IP stack, and to send the container or object to a server (e.g., 142). By using object(s) with defined resources, a FDS or CO detection device may construct a message using index references to resource definitions with a very small amount of data that conveys complex and varied information to a receiving device (e.g., a server). For example, the fire and/or CO alarm object 500a may include resources that may be indexed, for example, by a Resource Definition ID (such as Resource Definition IDs 1-14).

Each resource definition may include a name, and an indicator of permitted operation(s) on or for the resource (e.g., a permissible operation), such as Read (R), Read-Write (RW), or Execute (E), or other operations (as may be, for example, defined in a standard such as the LwM2M standard). Each resource definition may also include a permitted number of instances (e.g., "single") of the resource, whether an operation is Mandatory or Optional, and a data type where applicable. A data type may include, for example, Boolean, Float, String, or Integer for certain data types, or none for executable commands (e.g., Resource Definition ID 10 "Reset"). Each resource definition may also include a permitted range or enumeration of the relevant information for that resource (e.g., 0-600) and permissible units (e.g., parts per million (ppm), decibel (dB), degrees (deg), meters (m), or any other suitable unit). Each resource definition may also include a description of the meaning of a value or values associated with each resource definition. For example, a value associated with Resource Definition ID 1 (CO Detected) will be interpreted to indicate "CO not detected" is the value is 0, and "CO detected" if the value is 1. As another example, a value associated with Resource Definition ID 3 (CO Value) will be interpreted to indicate a last or current measured CO value from a sensor (e.g., in parts per million).

FIG. 5F illustrates aspects of an example fire and/or CO alarm object 500f (illustrated in FIG. 5F as a CO Detector Object) according to various embodiments. Although the fire and/or CO alarm object 500f is discussed in view of the LwM2M standard, any suitable object or arrangement of information may be used in various embodiments.

With reference to FIGS. 1-5F, as noted above, NIDD may enable the FDS or CO detection device (e.g., 120c, 120d, 200, 300, 402) to embed a small amount of data in a container or object without use of an IP stack, and to send the container or object to a server (e.g., 142). By using object(s) with defined resources, a FDS or CO detection device may construct a message using index references to resource definitions with a very small amount of data that conveys complex and varied information to a receiving device (e.g., a server). For example, the fire and/or CO alarm object 500f may include resources that may be indexed, for example, by a Resource Definition ID (such as Resource Definition IDs 0-10, 6048, 5514, 5515, 6039, and 6044).

Each resource definition may include a name, and an indicator of permitted operation(s) on or for the resource, such as Read (R), Read-Write (RW), or Execute (E), or other operations (as may be, for example, defined in a standard such as the LwM2M standard). Each resource definition may also include a permitted number of instances (e.g., "single") of the resource, whether an operation is Mandatory or Optional, and a data type where applicable. A data type may include, for example, Boolean, Float, String, or Integer for certain data types, or none for executable commands (e.g., Resource Definition ID 10 "Reset"). Each resource definition may also include a permitted range or enumeration of the relevant information for that resource (e.g., 0-600) and permissible units (e.g., parts per million (ppm), decibel (dB), degrees (deg), meters (m), or any other suitable unit). Each resource definition may also include a description of the meaning of a value or values associated with each resource definition. For example, a value associated with Resource Definition ID 1 (CO Detected) will be interpreted to indicate "CO not detected" is the value is 0, and "CO detected" if the value is 1. As another example, a value associated with Resource Definition ID 3 (CO Value) will be interpreted to indicate a last or current measured CO value from a sensor (e.g., in parts per million). As another example, a value from 0.00 to 100.00 associated with Resource Definition 6044 (Battery Percentage) will be interpreted to indicate a percentage of current remaining in the batter of the FDS or CO detection device.

Figure 6:
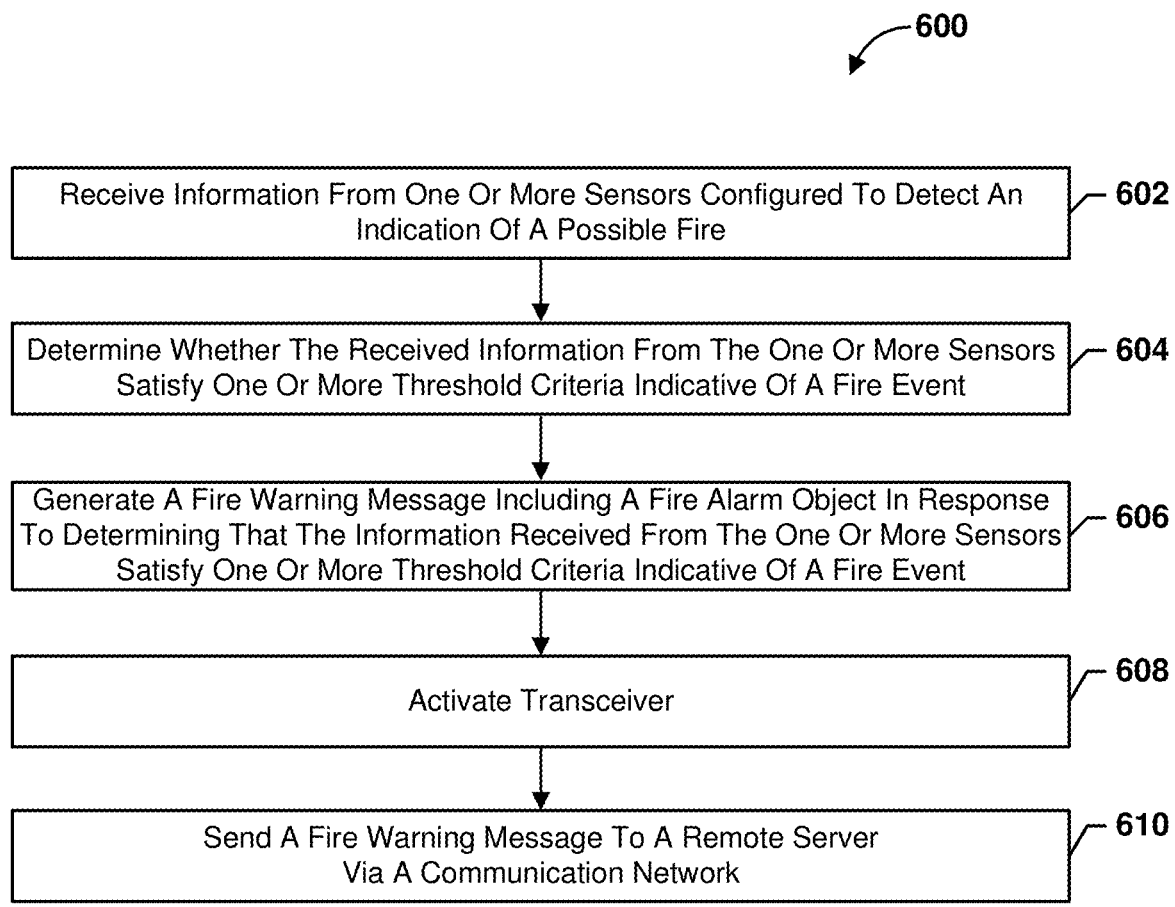
FIG. 6 is a process flow diagram illustrating a method that may be performed by a processor of an FDS device for communicating a potential fire detection to a wireless communication network device according to some embodiments.

FIG. 6 is a process flow diagram illustrating a method 600 that may be performed by a processor of an FDS or CO detection for communicating a potential fire or CO detection to a wireless communication network device according to some embodiments. With reference to FIGS. 1-6, means for performing the operations of the method 600 may be hardware components of an FDSFDS or CO detection device (e.g., 120c, 120d, 200, 300, 402) the operation of which may be controlled by one or more processors (e.g., the processors 312, 314, 316, 318, 352, 366).

In block 602, the processor may receive information from one or more sensors configured to detect an indication of a possible fire. For example, the processor may receive information from one or more of the FDS or CO detection sensors 230-246. In some embodiments, the processor may receive the information from the one or more sensors via a wireless communication link. In some embodiments, the processor may receive the information from the one or more sensors via a wired communication link. In some embodiments, means for performing functions of the operations in block 602 may include the processor (e.g., 312, 314, 316, 318, 352, 366) coupled to one or more sensors (e.g., 230-246).

In block 604, the processor may determine whether information received from the one or more sensors satisfy one or more threshold criteria indicative of a fire event or CO detection. In some embodiments, means for performing functions of the operations in block 604 may include the processor (e.g., 312, 314, 316, 318, 352, 366).

In block 606, the processor may generate a fire warning message comprising a fire alarm object in response to determining that the information received from the one or more sensors satisfy one or more threshold criteria indicative of a fire event or CO detection. In some embodiments, means for performing functions of the operations in block 604 may include the processor (e.g., 312, 314, 316, 318, 352, 366).

In block 608, the processor may activate a transceiver. In some embodiments, the FDSFDS or CO detection device may be configured as a device with a small battery or an otherwise limited power supply. In some embodiments, to save power, the FDS device may operate a transceiver in a lower power or standby state, and may power up or activate the transceiver to communicate messages such as the fire warning message. In some embodiments, the communication network may include a wired communication network. In some embodiments, the communication network may include a wireless communication network. In some implementations, means for performing functions of the operations in block 606 may include the processor (e.g., 312, 314, 316, 318, 352, 366) coupled to a wireless transceiver (e.g., 208).

In block 610, the processor may send a fire warning message to a remote server via a communication network (e.g., using the transceiver). In some embodiments, the fire warning message may include a fire alarm object that includes a defined resource configured to indicate one or more of the detected ambient temperature and the at least one additional ambient reading from another sensor of the FDSFDS or CO detection device or a Lightweight Machine-to-Machine (LwM2M) extensible object. In some embodiments, the fire warning message may include an identifier (ID) of the reporting FDSFDS or CO detection device, which a remote server may use to look up the location (e.g., provided during an initial phase following deployment), sensor capabilities and other information regarding the reporting FDSFDS or CO detection device stored in memory of the server. In some embodiments, the processor may send location information of the FDSFDS or CO detection device to the wireless communication network as part of the fire warning message. The location information may include a coordinate location of the FDSFDS or CO detection device, or other such information that indicates a geographic location of the FDs device. In some implementations, means for performing functions of the operations in block 606 may include the processor (e.g., 312, 314, 316, 318, 352, 366) coupled to the wireless transceiver (e.g., 208).

Figure 7:
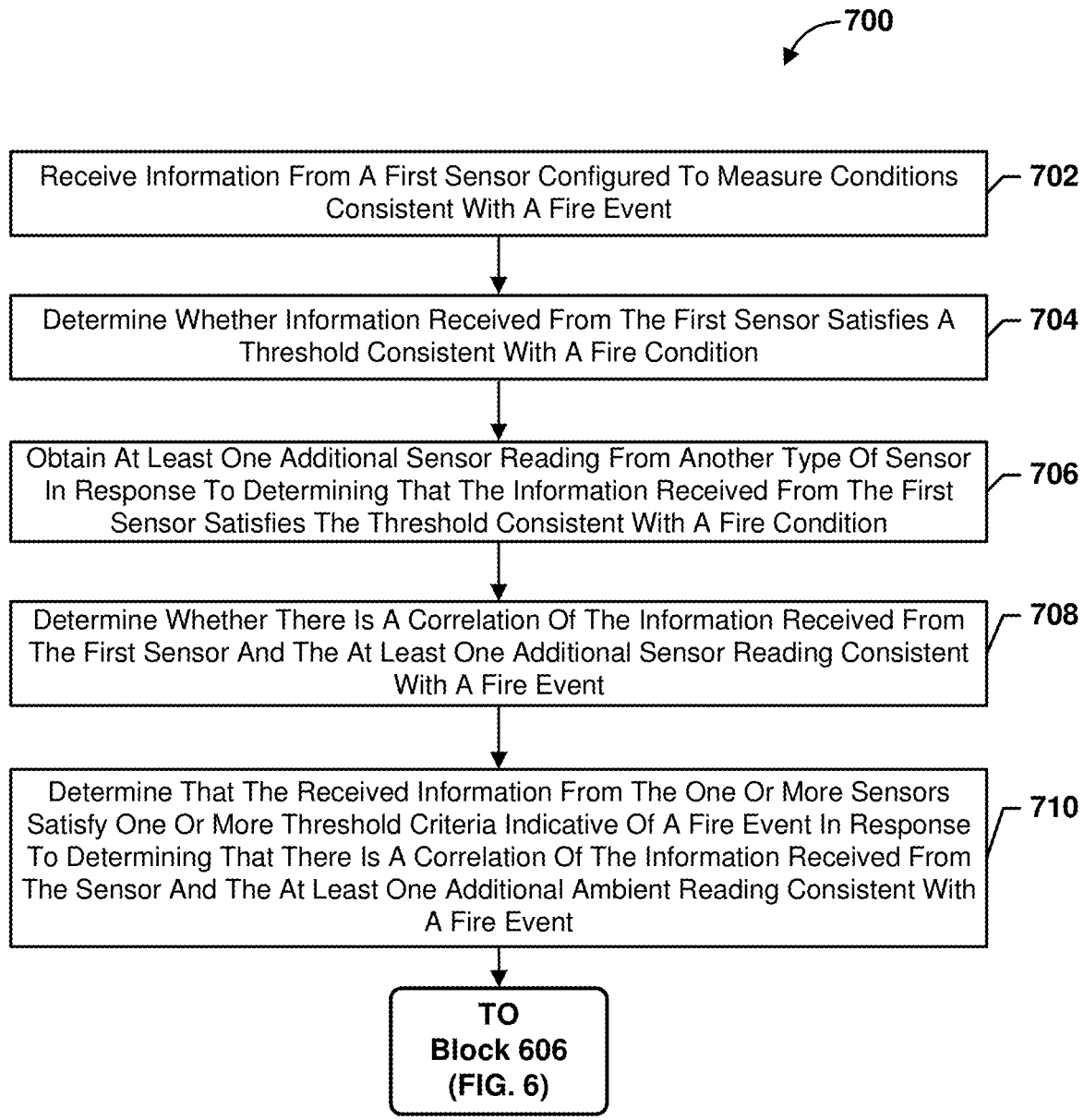
FIGS. 7-11 are process flow diagrams illustrating operations that may be performed by a processor of an FDS detection device as part of the method for communicating a potential fire detection to a wireless communication network device according to some embodiments.

FIG. 7 is a process flow diagram illustrating operations 700 that may be performed by a processor of an FDSFDS or CO detection device as part of the method 600 for communicating a potential fire or CO detection to a wireless communication network according to some embodiments. The operations 700 enable an FDSFDS or CO detection device to detect or infer a fire or CO detection event that should be reported based on the combination of readings from two or more sensors. Using two or more sensors or making the initial fire or CO detection determination may be useful in avoiding false alarms as well as enabling detection of fire or CO detection events in which detected conditions on any one sensor do not exceed the fire or CO detection threshold but readings from multiple sensors are consistent with a fire or CO detection event. With reference to FIGS. 1-7, means for performing the operations 700 may be hardware components of an FDSFDS or CO detection device (e.g., 120c, 120d, 200, 300, 402) the operation of which may be controlled by one or more processors (e.g., the processors 312, 314, 316, 318, 352, 366).

In block 702, the processor may receive information from a first sensor configured to sense or measure a local or remote condition that is indicative of a fire event. For example, the processor may receive information from any one of the local ambient temperature sensors 230, the remote temperature sensor 232, the smoke detector 234, the image sensor 236, or the infrared sensor 238. In some embodiments, the processor may receive information from multiple sensors and combine or correlate the received information. In some embodiments, means for performing functions of the operations in block 702 may include the processor (e.g., 312, 314, 316, 318, 352, 366) coupled to the sensors 230-238.

In block 704, the processor may determine whether information received from the first sensor (or a combination of sensors) satisfies a threshold consistent with a fire condition. Some embodiments, this threshold may be a standalone detection threshold, such as a temperature, smoke detection, or gas (e.g., CO or CO2) that is predetermined as a clear indication of a fire event. In some embodiments, this threshold may be less than the standalone detection threshold, such as a temperature, smoke detection, or gas (e.g., CO or CO2) that is predetermined as a sensor reading that justifies activating and analyzing one or more other types of sensor readings to make a determination of whether a fire event is likely. In some embodiments, means for performing functions of the operations in block 702 may include the processor (e.g., 312, 314, 316, 318, 352, 366).

In block 706, the processor may obtain at least one additional ambient reading from another sensor in response to determining that the information received from the first sensor satisfies the threshold determined in block 704. For example, in response to determining that the first sensor reading (or combination of sensor reading) exceeds the threshold less than the standalone detection threshold, the processor may activate (if necessary) and obtain information from one or more other sensors 230-246 to be correlated with or analyzed in combination with the sensor information obtained from the first sensor in block 702. In some embodiments, means for performing functions of the operations in block 702 may include the processor (e.g., 312, 314, 316, 318, 352, 366) coupled to the sensors 230-246.

In block 708, the processor may determine whether there is a correlation of the information received from the first sensor and the at least one other sensor that is consistent with a fire event or CO detection. The operations in block 708 enable the processor to confirm that a first sensor reading exceeding the standalone FDS or CO detection threshold is not a false alarm by determining that a second type of sensor has a reading that is consistent with a fire event even if the second sensor reading is less than that sensor's standalone detection threshold. The operations in block 700 may also enable the processor to infer that a fire event is likely when the first sensor reading is close to but shy of the standalone FDS or CO detection threshold (e.g., exceeds a lower threshold) by evaluating the first sensor reading in the context of a second different sensor reading. For example, the processor may determine that a fire condition is likely in response to determining that the ambient temperature exceeds a second temperature threshold, an ambient humidity exceeds a humidity threshold, and a smoke reading is positive. In such embodiments, the second temperature threshold and the humidity threshold may be based on environment information for the area proximate to the FDS device (i.e., that the processor may receive from the wireless communication network). In some embodiments, means for performing functions of the operations in block 708 may include the processor (e.g., 312, 314, 316, 318, 352, 366).

In block 710, the processor may determine that a reportable fire event condition exists in response to determining that there is a correlation of the information received from the first sensor and the at least one additional sensor reading consistent with a fire event. In some embodiments, means for performing functions of the operations in block 710 may include the processor (e.g., 312, 314, 316, 318, 352, 366).

The processor may perform the operations of block 606 of the method 600 (FIG. 6) to generate a fire warning message including a fire alarm object as described.

Figure 8:
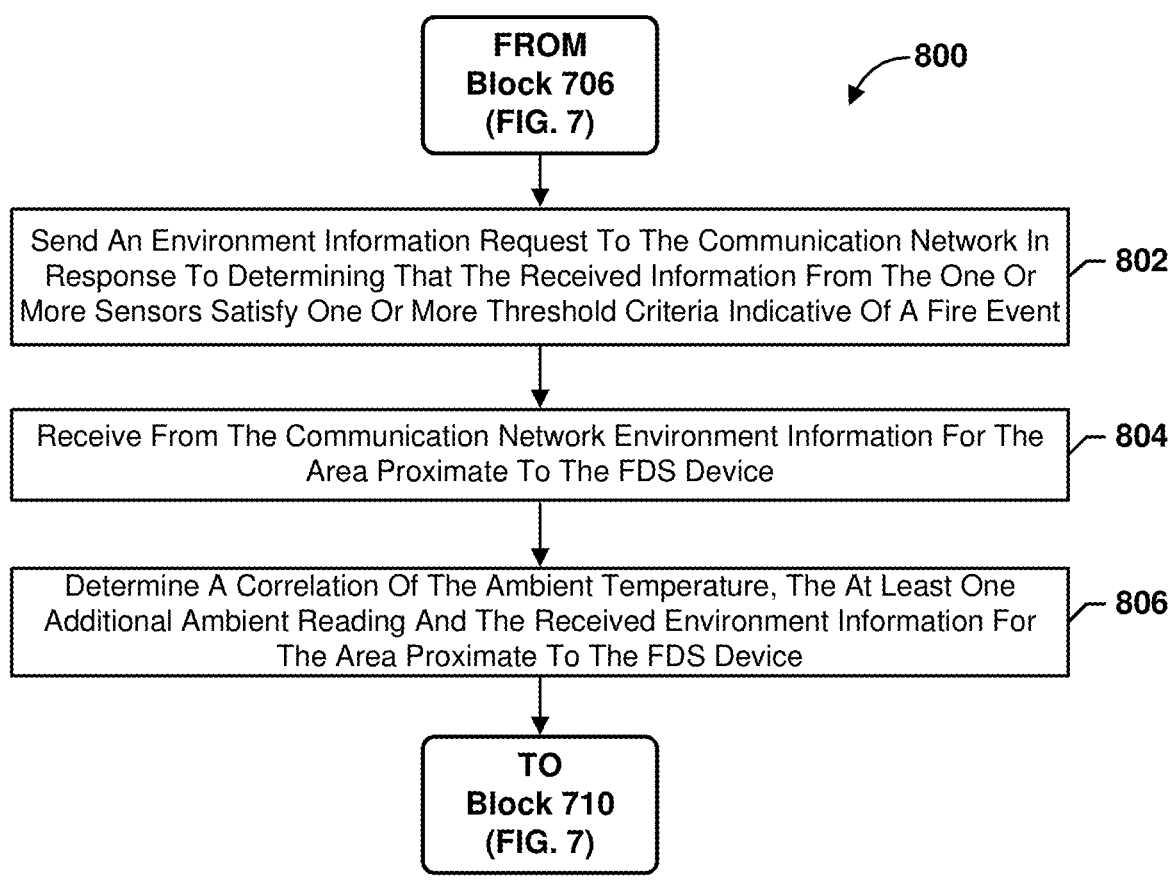

FIG. 8 is a process flow diagram illustrating operations 800 that may be performed by a processor of an FDS device as part of the method 700 for communicating a potential fire detection to a wireless communication network according to some embodiments. With reference to FIGS. 1-8, means for performing the operations 800 may be hardware components of an FDSFDS or CO detection device (e.g., 120c, 120d, 200, 300, 402) the operation of which may be controlled by one or more processors (e.g., the processors 312, 314, 316, 318, 352, 366).

In block 802, the processor may send an environment information request to the wireless communication network in response to determining that the information received from the one or more sensors satisfy one or more threshold criteria indicative of a fire event. In some embodiments, means for performing functions of the operations in block 802 may include the processor (e.g., 312, 314, 316, 318, 352, 366) coupled to the wireless transceiver (e.g., 208).

In block 804, the processor may receive from the wireless communication network environment information for the area proximate to the FDS device. In some embodiments, means for performing functions of the operations in block 804 may include the processor (e.g., FDS or CO detection 312, 314, 316, 318, 352, 366) coupled to the wireless transceiver (e.g., 208).

In block 806, the processor may determine a correlation of the ambient temperature, the at least one additional ambient reading and the received environment information for the area proximate to the FDSFDS or CO detection device. In some embodiments, means for performing functions of the operations in block 806 may include the processor (e.g., 312, 314, 316, 318, 352, 366).

The processor may then determine that a reportable fire event condition exists in block 710 of the operations 700 (FIG. 7) as described.

Figure 9:
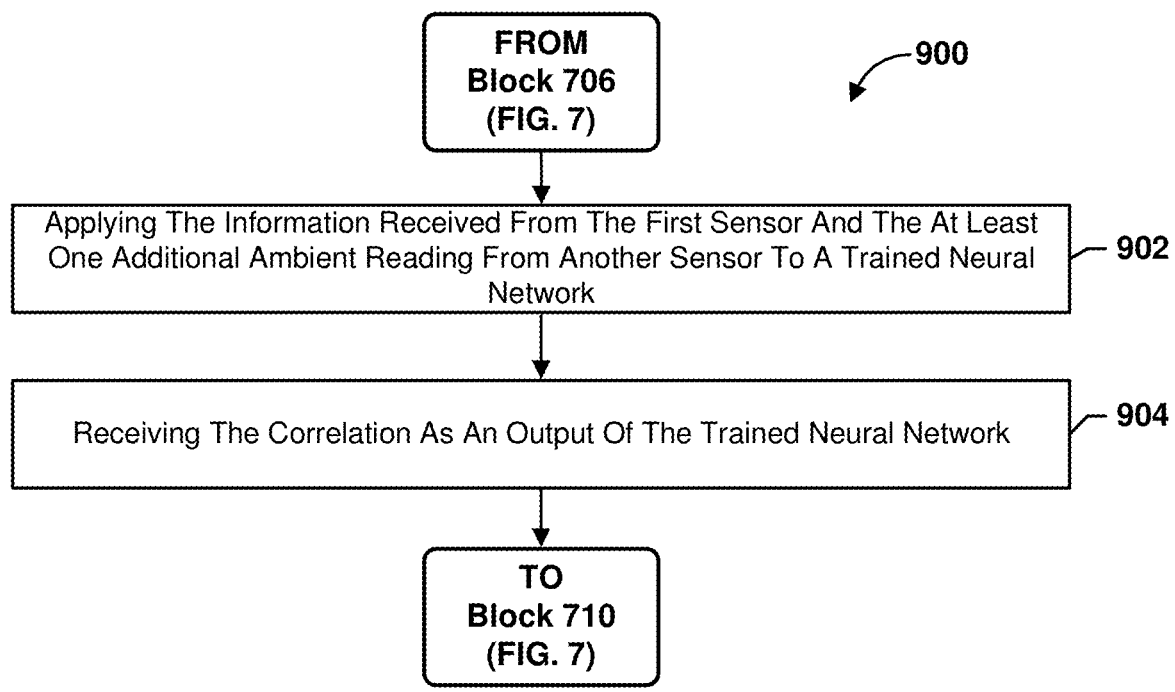

FIG. 9 is a process flow diagram illustrating operations 900 that may be performed by a processor of an FDSFDS or CO detection device as part of the method 700 for communicating a potential fire detection to a wireless communication network according to some embodiments. With reference to FIGS. 1-9, means for performing the operations 900 may be hardware components of an FDSFDS or CO detection device (e.g., 120c, 120d, 200, 300, 402) the operation of which may be controlled by one or more processors (e.g., the processors 312, 314, 316, 318, 352, 366).

Following performance of the operations of block 706 (FIG. 7), the processor may apply the information received from the first sensor and the at least one additional ambient reading from another sensor to a trained neural network in block 902. In some embodiments, means for performing functions of the operations in block 902 may include the processor (e.g., 312, 314, 316, 318, 352, 366).

In block 904, the processor may receive the correlation as an output of the trained neural network. In some embodiments, means for performing functions of the operations in block 904 may include the processor (e.g., 312, 314, 316, 318, 352, 366).

The processor may then determine that a reportable fire event condition exists in block 710 of the operations 700 (FIG. 7) as described.

Figure 10:
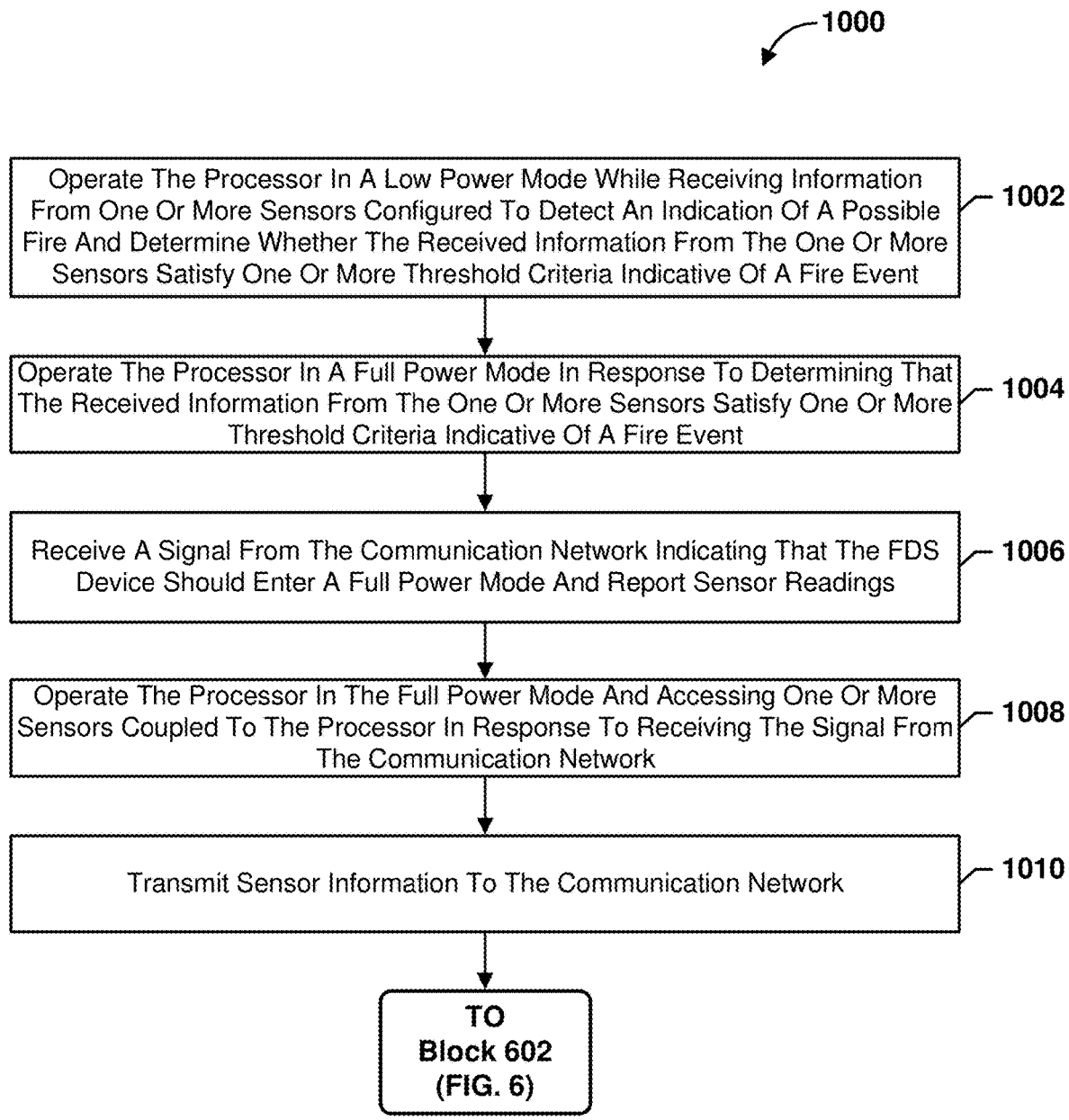

FIG. 10 is a process flow diagram illustrating operations 1000 that may be performed by a processor of an FDS device as part of the method 600 for communicating a potential fire to a wireless communication network according to some embodiments. With reference to FIGS. 1-10, means for performing the operations 1000 may be hardware components of an FDS device (e.g., 120c, 120d, 200, 300, 402) the operation of which may be controlled by one or more processors (e.g., the processors 312, 314, 316, 318, 352, 366).

In some embodiments, the FDS device may be configured to conserve battery power in order to operate for long periods of time without (or with minimal) battery recharging or replacement. For example, in block 1002, the processor may operate the processor in a low-power mode (first power mode) while receiving information from one or more sensors configured to detect an indication of a possible fire and determine whether information received from the one or more sensors satisfy one or more threshold criteria indicative of a fire event. In some embodiments, means for performing functions of the operations in block 1002 may include the processor (e.g., 312, 314, 316, 318, 352, 366) coupled to the wireless transceiver (e.g., 208).

In block 1004, the processor may operate the processor in a full-power mode (second power mode) (or otherwise in a power mode using more power than the low-power mode) in response to determining that the information received from the one or more sensors satisfies one or more threshold criteria indicative of a fire event. So long as the processor does not determine that the received information from one or more sensors satisfies one or more threshold criteria indicative of a fire event, the processor may continue to operate in the low power mode. In some embodiments, means for performing functions of the operations in block 1004 may include the processor (e.g., 312, 314, 316, 318, 352, 366).

In block 1006, if not already in the full-power mode is a result of the operations in block 1004, the processor may receive a signal from the wireless communication network indicating that the FDS device should enter a full-power mode and report sensor readings. In some embodiments, means for performing functions of the operations in block 1006 may include the processor (e.g., 312, 314, 316, 318, 352, 366) coupled to the wireless transceiver (e.g., 208).

In block 1008, the processor may operate in the full-power mode in response to either determining that the received information from one or more sensors satisfies one or more threshold criteria indicative of a fire event or receiving a signal from the wireless communication network indicating that the FDS device should enter the full power mode and report sensor readings, and may access one or more sensors coupled to the processor in response to receiving the signal from the wireless communication network. In some embodiments, means for performing functions of the operations in block 1008 may include the processor (e.g., 312, 314, 316, 318, 352, 366) coupled to the wireless transceiver (e.g., 208) and one or more sensors (e.g., 230-246.)

In block 1010, the processor may transmit the sensor information while in in the full-power mode to the wireless communication network. In some embodiments, means for performing functions of the operations in block 1008 may include the processor (e.g., 312, 314, 316, 318, 352, 366) coupled to the wireless transceiver (e.g., 208).

The processor may continue to receive information from one or more sensors configured to detect an indication of a possible fire in block 602 of the method 600 (FIG. 6) as described.

Figure 11:
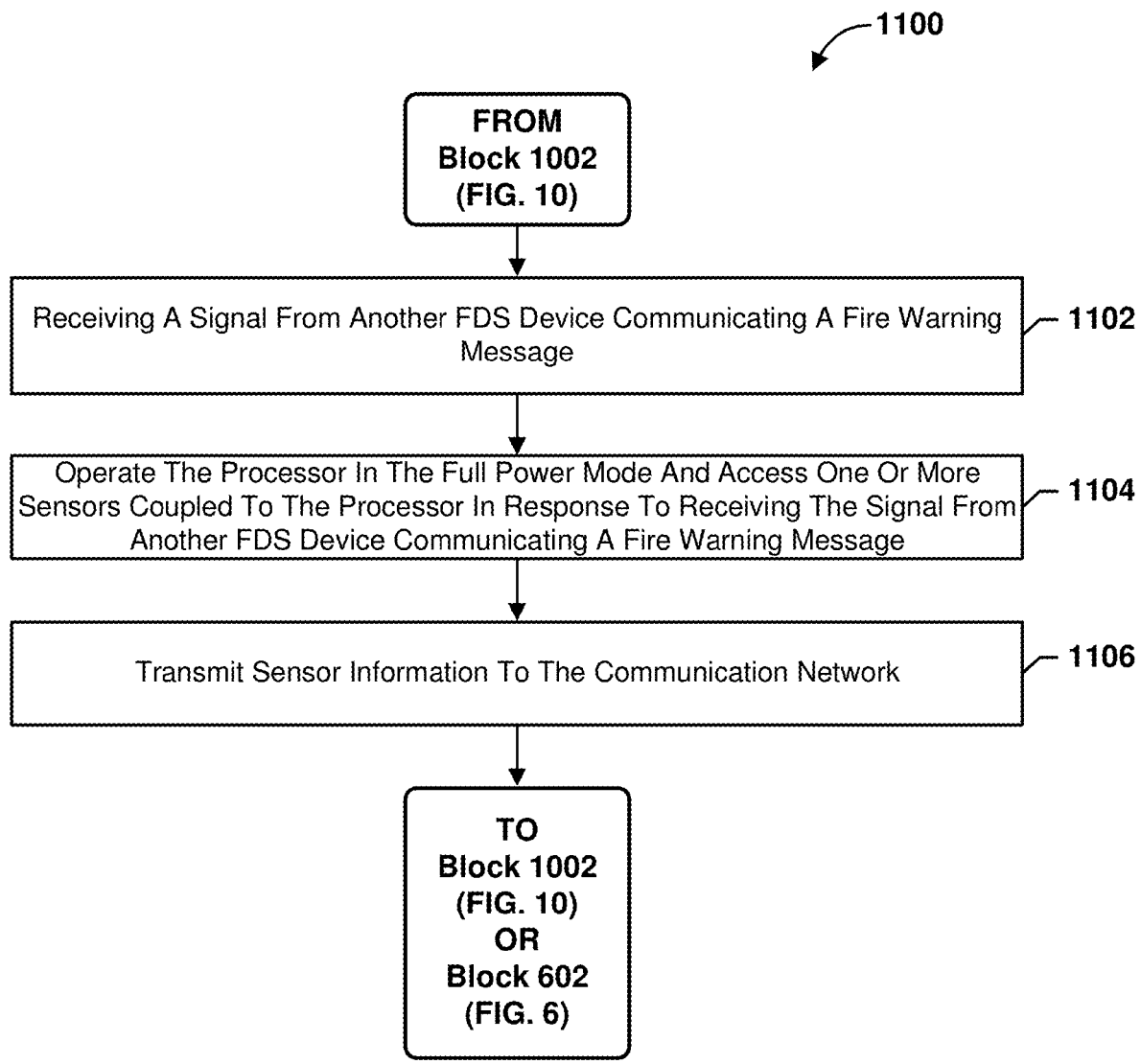

FIG. 11 is a process flow diagram illustrating operations 1100 that may be performed by a processor of an FDS device as part of the methods 600, 1000 for communicating a potential fire to a wireless communication network according to some embodiments. With reference to FIGS. 1-11, means for performing the operations 1100 may be implemented in hardware components and/or software components of an FDS device (e.g., 120c, 120d, 200, 300, 402) the operation of which may be controlled by one or more processors (e.g., the processors 312, 314, 316, 318, 352, 366).

In some embodiments, an FDS device may signal another FDS device to power up and report sensor information to the wireless communication network. For example, an FDS device that detects a potential or actual fire event may send a signal to nearby FDS device(s) to detect and report conditions in their vicinity. In this manner, an FDS device that detects a potential or actual fire event by one FDS device may also request or instruct other FDS devices to provide information that may enable early and accurate mapping of the potential or actual fire event.

In some embodiments, following the performance of the operations of block 1002 (FIG. 10), the processor may receive a signal from another FDS device communicating a fire warning message in block 1102. In some implementations, means for performing functions of the operations in block 1102 may include the processor (e.g., 312, 314, 316, 318, 352, 366) coupled to the wireless transceiver (e.g., 208).

In block 1104, the processor may operate the processor in the full-power mode and access one or more sensors coupled to the processor in response to receiving the signal from another FDS device communicating a fire warning message. In some implementations, means for performing functions of the operations in block 1104 may include the processor (e.g., 312, 314, 316, 318, 352, 366) coupled to the wireless transceiver (e.g., 208) and one or more sensors (e.g., 230-246.)

In block 1106, the processor may transmit sensor information to the wireless communication network. In some implementations, means for performing functions of the operations in block 1106 may include the processor (e.g., 312, 314, 316, 318, 352, 366) coupled to the wireless transceiver (e.g., 208).

In some embodiments, the processor may operate the processor in a low-power mode (first power mode) in block 1002 of the method 1000 (FIG. 10) as described. In some embodiments, the processor may continue to receive information from one or more sensors configured to detect an indication of a possible fire in block 602 of the method 600 (FIG. 6) as described.

Figure 12:
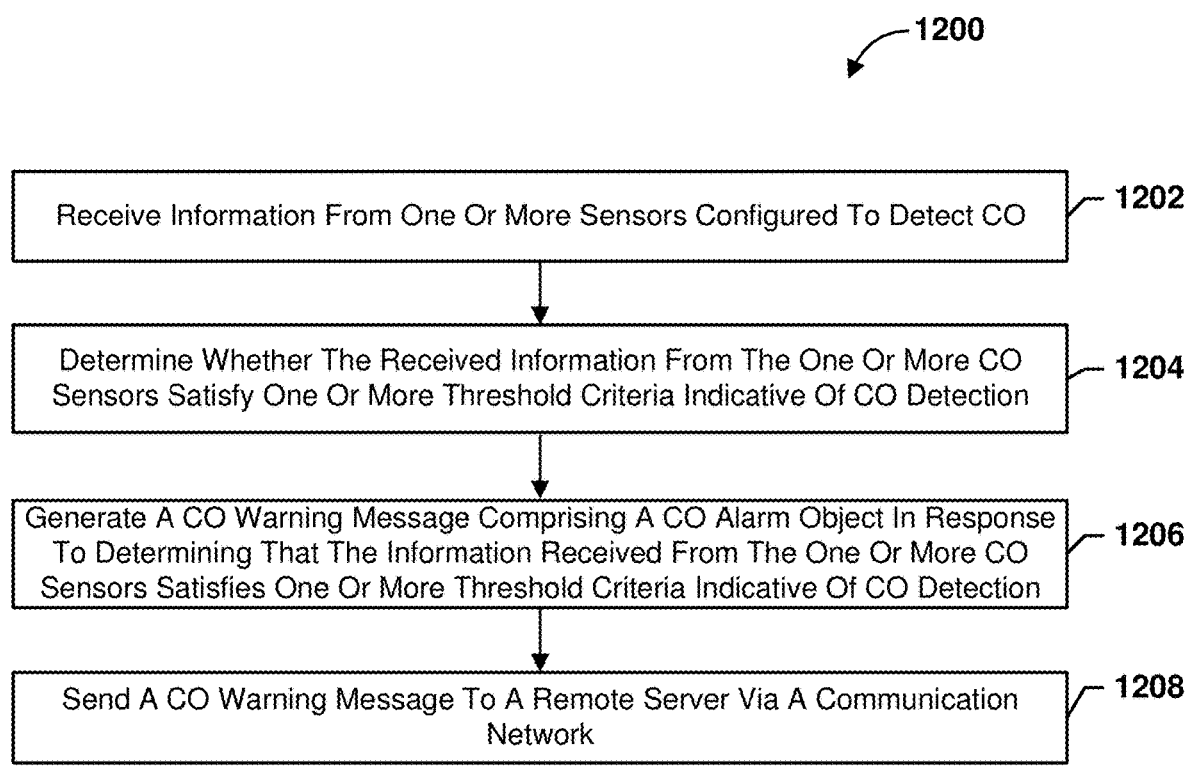
FIG. 12 is a process flow diagram illustrating a method that may be performed by a processor of a CO detection device for communicating a CO detection to a wireless communication network device according to some embodiments.

FIG. 12 is a process flow diagram illustrating a method 1200 that may be performed by a processor of a CO detection device for communicating a CO detection to a wireless communication network device according to some embodiments. With reference to FIGS. 1-11, means for performing the operations of the method 1200 may be hardware components of a CO detection device (e.g., 120c, 120d, 200, 300, 402) the operation of which may be controlled by one or more processors (e.g., the processors 312, 314, 316, 318, 352, 366).

In block 1202, the processor may receive information from CO sensor(s) (e.g., 252). In some embodiments, the CO sensor(s) may be included in the CO detection device and coupled to the processor by a bus (e.g., PCIe bus, USB, etc.). In some embodiments, the processor may receive the information from the CO sensor(s) via a wireless communication link. In some embodiments, the processor may receive the information from the CO sensor(s) via a wired communication link. In some embodiments, means for performing functions of the operations in block 1202 may include the processor (e.g., 312, 314, 316, 318, 352, 366) coupled to CO sensor(s) (e.g., 252).

In block 1204, the processor may determine whether the information received from the CO sensor(s) satisfies one or more threshold criteria indicative of CO detection. For example, the processor may determine whether a measured CO concentration in the air exceeds a threshold for reporting CO detection. In some embodiments, means for performing functions of the operations in block 1204 may include the processor (e.g., 312, 314, 316, 318, 352, 366).

In block 1206, the processor may generate a fire and/or CO warning message including a fire and/or CO alarm object in response to determining that the information received from the CO sensor(s) satisfies one or more threshold criteria indicative of CO detection. In various embodiments, the network transceiver may be a wired network transceiver, a wireless transceiver, or a transceiver capable of communicating via wired and/or wireless communications networks. For example, the CO detection device may exit a low power mode to activate a wireless transceiver in response to detecting CO (e.g., a level or concentration of CO that satisfies a threshold criteria). In some embodiments, the CO detection device may activate a wired transceiver or modem coupled to a wired communications network in response to detecting CO. In some embodiments, means for performing functions of the operations in block 1206 may include the processor (e.g., 312, 314, 316, 318, 352, 366) coupled to a wireless transceiver (e.g., 208).

In block 1208, the processor may send a fire and/or CO warning message (e.g., to a remote server) to a remote server via a communication network (e.g., using the transceiver). In some embodiments, the processor may activate a transceiver, and may send the generated fire and/or CO warning message to the remote sever via the communication network using the activated transceiver. In some embodiments, the fire and/or CO warning message may include a fire and/or CO alarm object that includes a defined resource that indicates one or more readings of a sensor of the CO detection device in a Lightweight Machine-to-Machine (LwM2M) extensible object. In some embodiments, the fire and/or CO warning message may include an identifier (ID) of the reporting CO detection device, which a remote server may use to look up the location (e.g., provided during an initial phase following deployment), sensor capabilities and other information regarding the reporting CO detection device stored in memory of the server.

In some embodiments, the processor may send location information of the CO detection device to the communication network as part of the fire and/or CO warning message sent in block 1208. The location information may include a coordinate location of the CO detection device, or other such information (e.g., a street address) that indicates a geographic location of the CO detection device. In some embodiments, the location information may include a location tag, such as stored in memory at the time of installation indicating a specific location within a building (e.g., floor, room number, etc.) in addition to the building's address and/or geographic coordinates. In some embodiments, the location information included with a fire and/or CO warning message may include geographic and altitude coordinates obtained from a GNSS receiver (e.g., a GPS or similar receiver) within or coupled to the CO detection device. Additionally, CO detection devices implemented in a vehicle, UAV, boat, aircraft, or otherwise mobile (e.g., configured to be hand carried) may also include an indication of the speed at which the device is traveling along with a timestamp reporting when the reported location and speed information were determined. In some embodiments, the location information included in the fire and/or CO warning messages may reuse geographic coordinate and altitude information determined as defined in the OMA LwM2M version 1.1 specification.

In some embodiments, the network transceiver may send the fire and/or CO warning message in block 1208 via a wired communication network. In some embodiments, the network transceiver may send the fire and/or CO warning message via a wireless communication network. In some embodiments, the network transceiver may send the fire and/or CO warning message via both a wired communication network and a wireless communication network, such as sending the fire and/or CO warning message to a remote server via a wired communication network (e.g., the Internet) and sending the fire and/or CO warning to wireless communication devices (e.g., a smartphone), such as via a WWAN. In some embodiments, the network transceiver may send the fire and/or CO warning message via a wireless mesh network relayed by other wireless devices, which may enable intercept by other CO detection devices. In some embodiments, means for performing functions of the operations in block 1208 may include the processor (e.g., 312, 314, 316, 318, 352, 366) coupled to memory and to the wireless transceiver (e.g., 208). In some implementation, means for performing functions of the operations in block 1208 may also include a GPS or GNSS receiver coupled to the processor.

Figure 13:
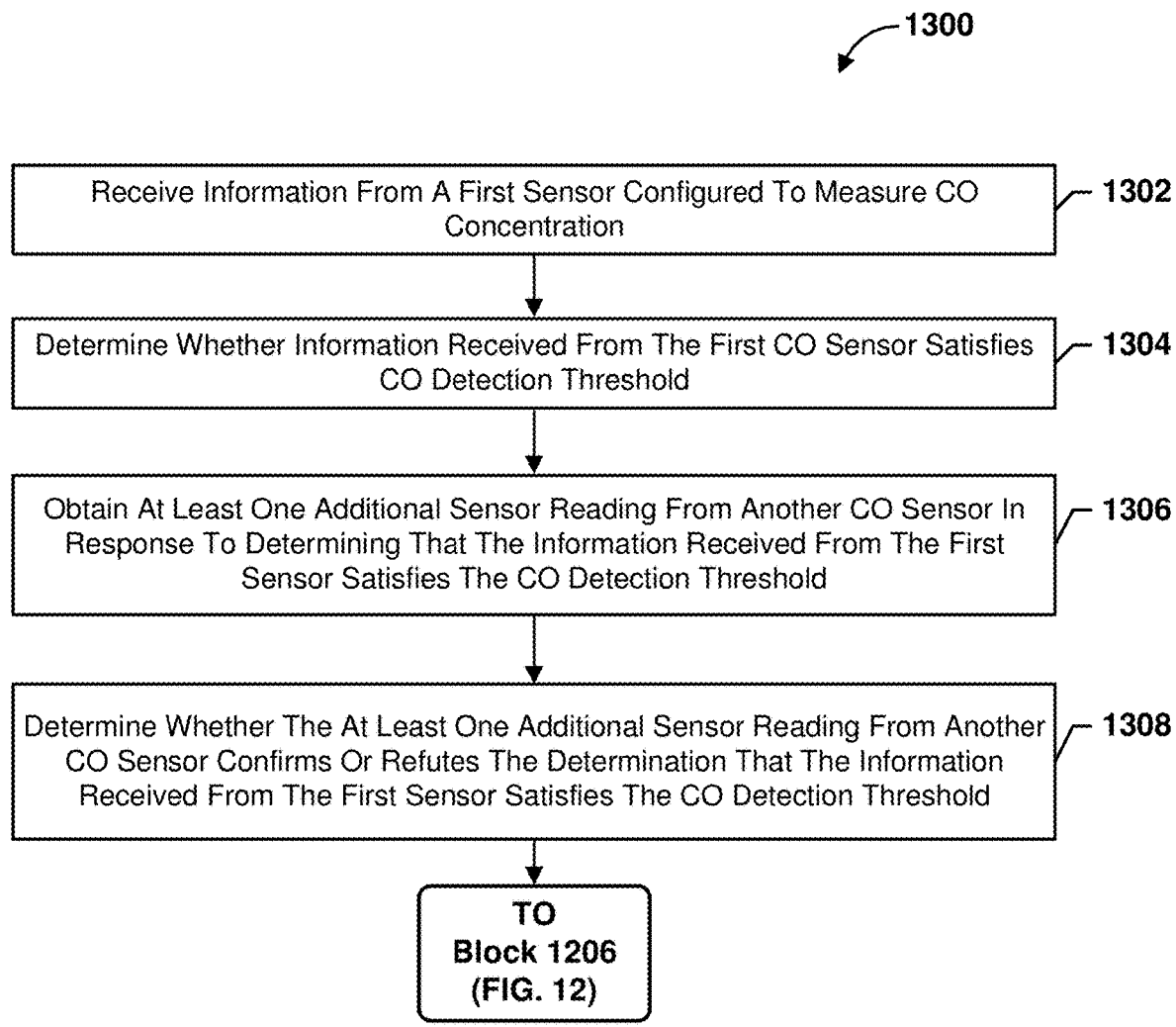
FIGS. 13-15 are process flow diagrams illustrating operations that may be performed by a processor of a CO detection device as part of the method for communicating a CO detection to a wireless communication network device according to some embodiments.

FIG. 13 is a process flow diagram illustrating operations 1300 that may be performed by a processor of a CO detection device as part of the method 1200 for communicating a CO detection to a wireless communication network according to some embodiments. The operations 1300 enable a CO detection device to detect or infer a CO detection event that should be reported based on the combination of readings from two or more sensors. Using two or more CO sensors or making the initial CO detection determination may be useful in avoiding false alarms as well as enabling detection of CO detection events in which detected conditions on any one sensor do not exceed the CO detection threshold but readings from multiple sensors are consistent with a CO detection event. With reference to FIGS. 1-12, means for performing the operations 1300 may be hardware components of a CO detection device (e.g., 120c, 120d, 200, 300, 402) the operation of which may be controlled by one or more processors (e.g., the processors 312, 314, 316, 318, 352, 366).

In block 1302, the processor may receive information from a first CO sensor configured to sense or measure CO concentration. For example, the processor may receive information from any of the CO sensors 252. In some embodiments, the processor may receive information from multiple CO sensors and combine or correlate the received information. In some embodiments, means for performing functions of the operations in block 1302 may include the processor (e.g., 312, 314, 316, 318, 352, 366) coupled to the CO sensor(s) 252.

In block 1304, the processor may determine whether information received from the first CO sensor (or a combination of sensors) satisfies a measure CO concentration. In some embodiments, means for performing functions of the operations in block 1304 may include the processor (e.g., 312, 314, 316, 318, 352, 366).

In block 1306, the processor may obtain at least one additional reading from another CO sensor in response to determining that the information received from the first CO sensor satisfies the threshold in block 1304. For example, in response to determining that the first CO sensor reading (or combination of sensor reading) exceeds the threshold less than the standalone detection threshold, the processor may activate (if necessary) and obtain information from one or more other CO sensors 252 to be correlated with or analyzed in combination with the sensor information obtained from the first CO sensor in block 1302. In some embodiments, other types of sensors may also be accessed as part of the operations in block 1306, such as smoke detectors, carbon dioxide sensors, chemical sensors, cameras, microphones, etc. In some embodiments, means for performing functions of the operations in block 1306 may include the processor (e.g., 312, 314, 316, 318, 352, 366) coupled to the CO sensor(s) 252.

In block 1308, the processor may determine whether the at least one additional sensor reading from another CO sensor confirms or refutes the determination that the information received from the first CO sensor satisfies the CO detection threshold. The operations in block 1308 enable the processor to confirm that a first CO sensor reading exceeding the CO detection threshold is not a false alarm by determining that a second CO sensor has a reading that is consistent with a CO detection event. In some embodiments, the processor may obtain at least one additional CO sensor reading from another CO detection device (e.g., via a wireless data link, such as a mesh network). In some embodiments, the processor may obtain at least one additional sensor reading from another type of sensor deployed via a robotic vehicle. In some embodiments, means for performing functions of the operations in block 1308 may include the processor (e.g., 312, 314, 316, 318, 352, 366).

The processor may perform the operations of block 1206 of the method 1200 (FIG. 12) to activate a network transceiver in response to determining that the information received from the CO sensor(s) satisfy one or more threshold criteria indicative of CO detection as described.

Figure 14:
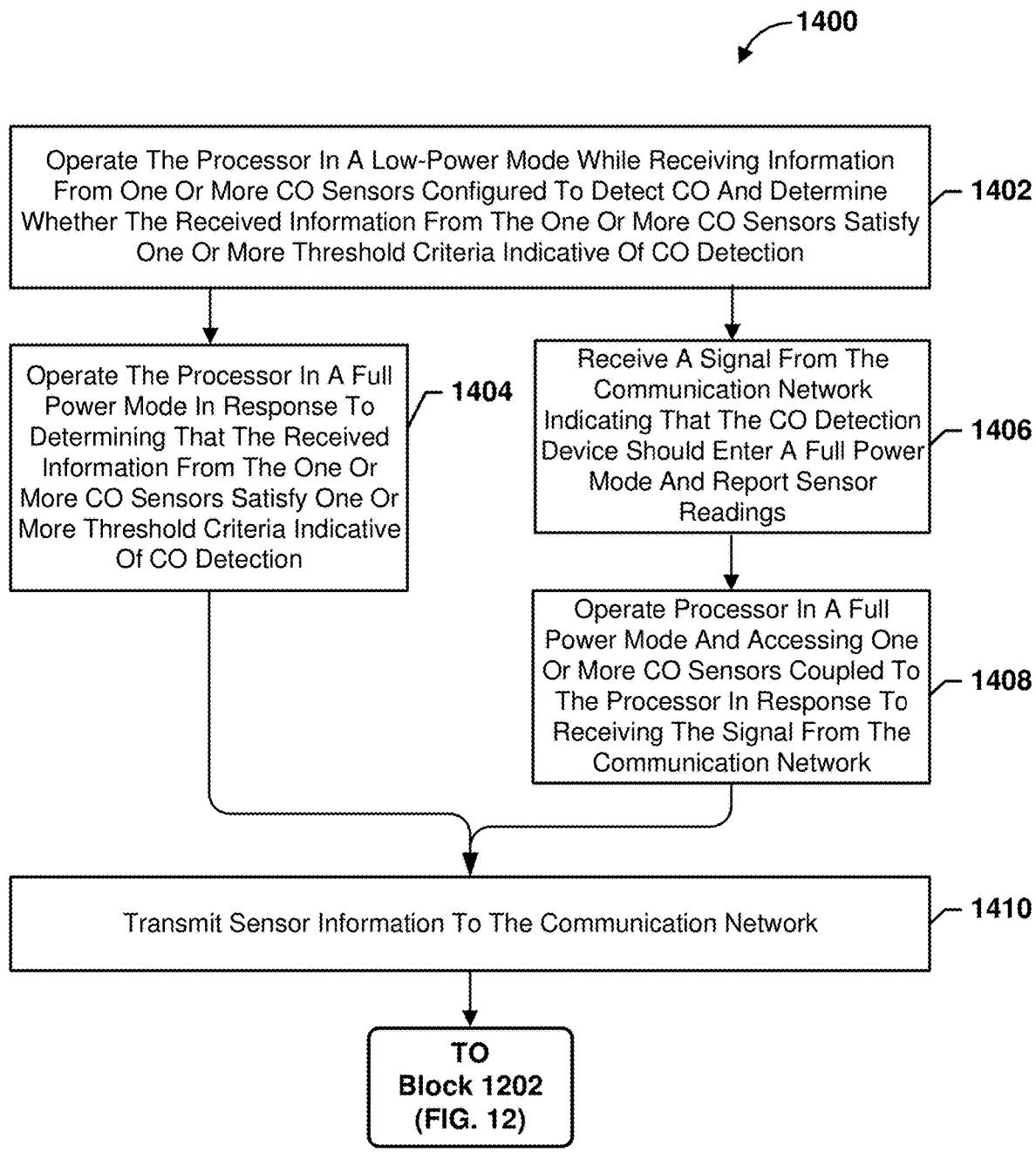

FIG. 14 is a process flow diagram illustrating operations 1400 that may be performed by a processor of a CO detection device as part of the method 1200 for communicating a CO detection to a wireless communication network according to some embodiments. With reference to FIGS. 1-8, means for performing the operations 1400 may be hardware components of a CO detection device (e.g., 120c, 120d, 200, 300, 402) the operation of which may be controlled by one or more processors (e.g., the processors 312, 314, 316, 318, 352, 366).

In some embodiments, the CO detection device may be configured to conserve battery power in order to operate for long periods of time without (or with minimal) battery recharging or replacement. For example, in block 1402, the processor may operate in a low-power mode (first power mode) while receiving information from CO sensor(s) configured to detect an indication of a possible CO detection event and determine whether the information received from the CO sensor(s) satisfy one or more threshold criteria indicative of CO detection. In some embodiments, means for performing functions of the operations in block 1402 may include the processor (e.g., 312, 314, 316, 318, 352, 366) coupled to the wireless transceiver (e.g., 208).

In block 1404, the processor may operate the processor in a full-power mode (second power mode) (or otherwise in a power mode using more power than the low-power mode) in response to determining that the information received from the CO sensor(s) satisfy one or more threshold criteria indicative of a CO detection. So long as the processor does not determine that the information received from CO sensor(s) satisfies one or more threshold criteria indicative of CO detection, the processor may continue to operate in the low power mode. In some embodiments, means for performing functions of the operations in block 1404 may include the processor (e.g., 312, 314, 316, 318, 352, 366).

In block 1406, if not already in the full-power mode is a result of the operations in block 1406, the processor may receive a signal from the wireless communication network indicating that the CO detection device should enter a full-power mode and report sensor readings. In some embodiments, means for performing functions of the operations in block 1006 may include the processor (e.g., 312, 314, 316, 318, 352, 366) coupled to the wireless transceiver (e.g., 208).

In block 1408, the processor may operate in the full-power mode in response to either determining that the information received from CO sensor(s) satisfies one or more threshold criteria indicative of a fire event or receiving a signal from the wireless communication network indicating that the CO detection device should enter the full power mode and report sensor readings, and may access CO sensor(s) coupled to the processor in response to receiving the signal from the wireless communication network. In some embodiments, means for performing functions of the operations in block 1408 may include the processor (e.g., 312, 314, 316, 318, 352, 366) coupled to the wireless transceiver (e.g., 208) and one or more CO sensor(s) (e.g., 252).

In block 1410, the processor may transmit the sensor information to the communication network. In some embodiments, the processor may transmit the sensor information while in in the full-power mode to the communication network. In some embodiments, the network transceiver may send the sensor information via a wired communication network. In some embodiments, the network transceiver may send the sensor information via a wireless communication network. In some embodiments, the network transceiver may send the sensor information via both a wired communication network and a wireless communication network, such as sending the sensor information to a remote server via a wired communication network (e.g., the Internet) and sending the sensor information to wireless communication devices (e.g., a smartphone), such as via a WWAN. In some embodiments, the network transceiver may send the sensor information via a wireless mesh network relayed by other wireless devices, which may enable intercept by other CO detection devices. In some embodiments, means for performing functions of the operations in block 810 may include the processor (e.g., 312, 314, 316, 318, 352, 366) coupled to the wireless transceiver (e.g., 208).

The processor may proceed to perform the operations of block 1202 of the method 1200 (FIG. 12) to receive information from CO sensor(s) as described.

Figure 15:
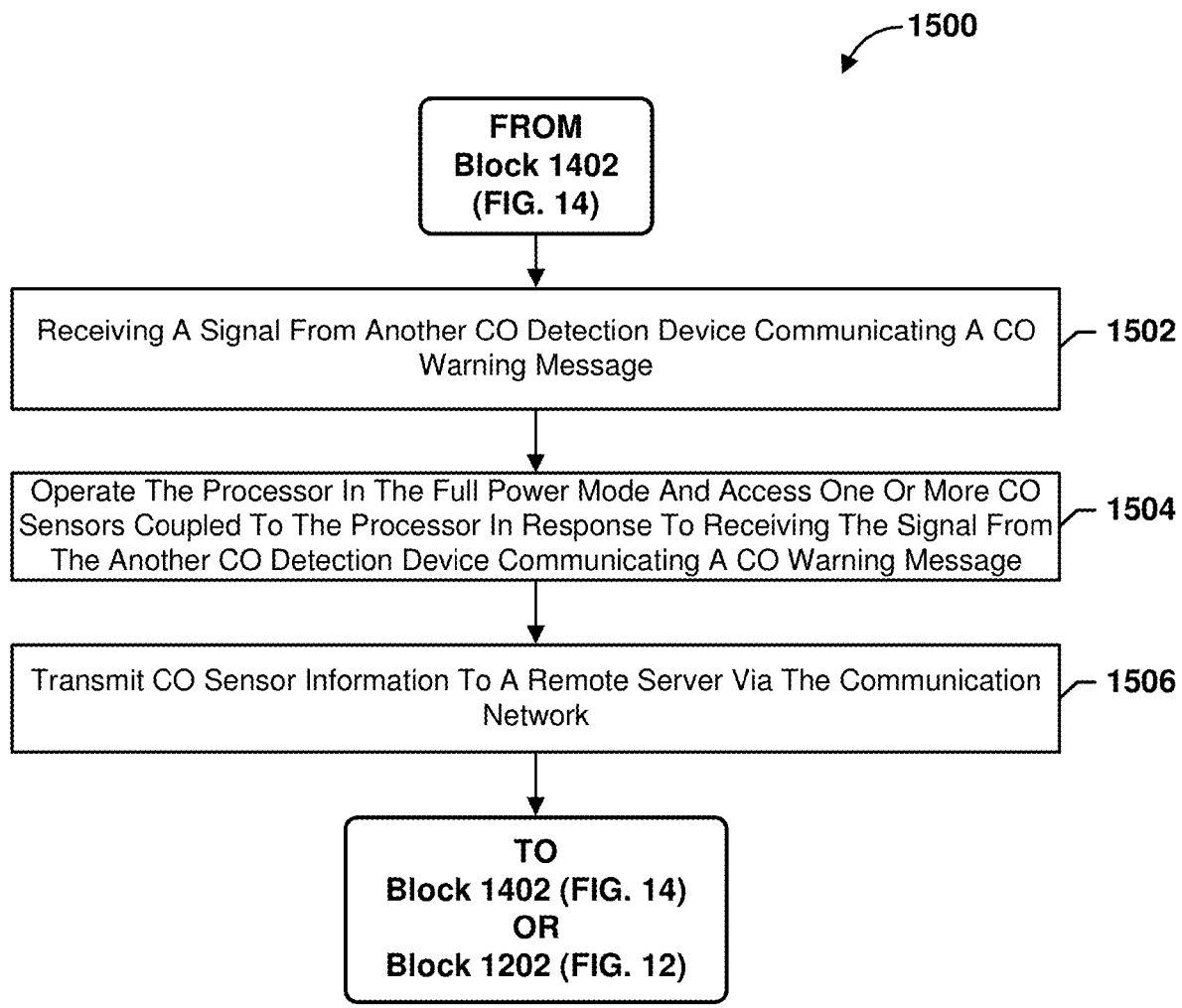

FIG. 15 is a process flow diagram illustrating operations 1500 that may be performed by a processor of a CO detection device as part of the method 1200 for communicating a CO detection to a wireless communication network according to some embodiments. With reference to FIGS. 1-9, means for performing the operations 1500 may be implemented in hardware components of a CO detection device (e.g., 120c, 120d, 200, 300, 402) the operation of which may be controlled by one or more processors (e.g., the processors 312, 314, 316, 318, 352, 366).

In some embodiments, a CO detection device may signal another CO detection device to power up and report sensor information to the wireless communication network. For example, a CO detection device that detects CO concentrations at or near a warning threshold may send a signal to nearby CO detection device(s) to detect and report CO concentrations in their vicinity. In this manner, a CO detection device that detects CO may also request or instruct other CO detection devices to provide information that may enable early and accurate mapping of CO concentrations, such as in various rooms or floors of a building.

In some embodiments, following the performance of the operations of block 1402 (FIG. 14), the processor may receive a signal from another CO detection device communicating a fire and/or CO warning message in block 1502. For example, the processor may recognize a fire and/or CO warning message that is being relayed via a mesh network of CO detection devices to a communication network for delivery to a remote server. In some embodiments, means for performing functions of the operations in block 1502 may include the processor (e.g., 312, 314, 316, 318, 352, 366) coupled to the wireless transceiver (e.g., 208).

In block 1504, the processor may operate the processor in the full-power mode and access CO sensor(s) coupled to the processor in response to receiving the signal from another CO detection device communicating a fire and/or CO warning message. In some embodiments, means for performing functions of the operations in block 1504 may include the processor (e.g., 312, 314, 316, 318, 352, 366) coupled to the wireless transceiver (e.g., 208) and one or more CO sensor(s) (e.g., 252.)

In block 1506, the processor may transmit sensor information to a remote server via the communication network. As described, processor may transmit sensor information via a wired communication network, a wireless communication network (e.g., a WWAN or a wireless mesh network), or both a wired communication network and a wireless communication network. In some embodiments, means for performing functions of the operations in block 1506 may include the processor (e.g., 312, 314, 316, 318, 352, 366) coupled to the wireless transceiver (e.g., 208).

In some embodiments, the processor may perform the operations of block 1402 of the operations 1400 (FIG. 14) to operate in the low-power mode FIG. as described. In some embodiments, the processor may perform the operations of block 1202 of the method 1200 (FIG. 12) to receive information from CO sensor(s) as described.

Figure 16:
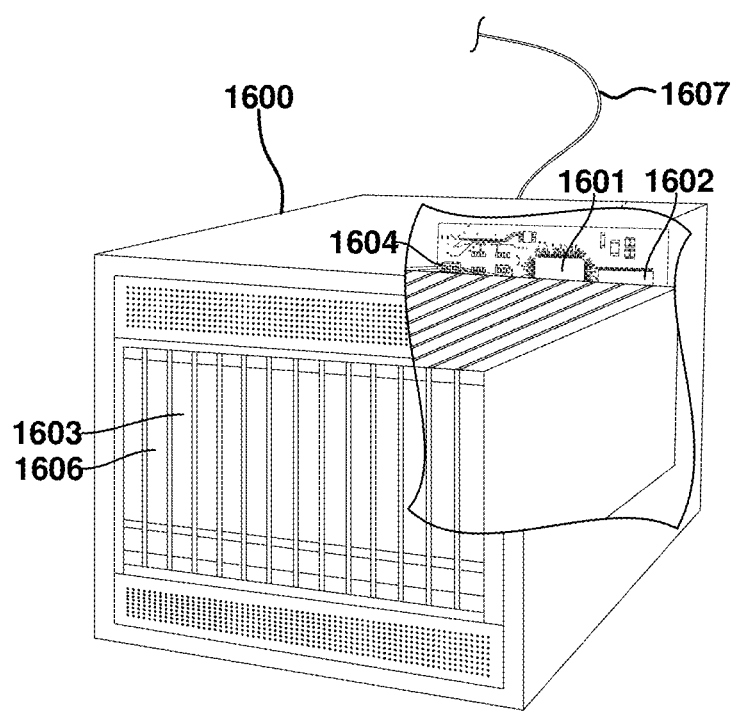
FIG. 16 is a component diagram of an example server suitable for use with various embodiments.

Various embodiments (including, but not limited to, embodiments discussed above with reference to FIGS. 1-15) may also be implemented on any of a variety of commercially available server devices, such as the server 1600 illustrated in FIG. 16. Such a server 1600 typically includes a processor 1601 coupled to volatile memory 1602 and a large capacity nonvolatile memory, such as a disk drive 1603. The server 1600 may also include a floppy disc drive, compact disc (CD) or digital versatile disc (DVD) drive 1606 coupled to the processor 1601. The server 1600 may also include one or more network transceivers 1604, such as a network access port, coupled to the processor 1601 for establishing network interface connections with a wireless communication network 1607, such as a local area network coupled to other announcement system computers and servers, the Internet, the public switched telephone network, and/or a cellular network (e.g., CDMA, TDMA, GSM, PCS, 3G, 4G, 5G, LTE, or any other type of cellular network).

The processors used in any embodiments may be any programmable microprocessor, microcomputer or multiple processor chip or chips that can be configured by software instructions (applications) to perform a variety of functions, including the functions of various embodiments described in this application. In some FDS or CO detection devices, multiple processors may be provided, such as one processor dedicated to wireless communication functions (e.g., in SOC 304) and one processor dedicated to running other applications (e.g., in SOC 302). Typically, software applications may be stored in the internal memory (e.g., 206, 320, 358) before they are accessed and loaded into a processor. The processor may include internal memory sufficient to store the application software instructions.

As used in this application, the terms "component," "module," "system," and the like are intended to include a computer-related entity, such as, but not limited to, hardware, firmware, a combination of hardware and software, software, or software in execution, which are configured to perform particular operations or functions. For example, a component may be, but is not limited to, a process running on a processor, a processor, an object, an executable, a thread of execution, a program, and/or a computer. By way of illustration, both an application running on an IoT device and the IoT device may be referred to as a component. One or more components may reside within a process and/or thread of execution and a component may be localized on one processor or core and/or distributed between two or more processors or cores. In addition, these components may execute from various non-transitory computer readable media having various instructions and/or data structures stored thereon. Components may communicate by way of local and/or remote processes, function or procedure calls, electronic signals, data packets, memory read/writes, and other known network, computer, processor, and/or process related communication methodologies.

A number of different cellular and mobile communication services and standards are available or contemplated in the future, all of which may implement and benefit from various embodiments. Such services and standards include, e.g., third generation partnership project (3GPP), long term evolution (LTE) systems, third generation wireless mobile communication technology (3G), fourth generation wireless mobile communication technology (4G), fifth generation wireless mobile communication technology (5G), global system for mobile communications (GSM), universal mobile telecommunications system (UMTS), 3GSM, general packet radio service (GPRS), code division multiple access (CDMA) systems (e.g., cdmaOne, CDMA1020TM), enhanced data rates for GSM evolution (EDGE), advanced mobile phone system (AMPS), digital AMPS (IS-136/TDMA), evolution-data optimized (EV-DO), digital enhanced cordless telecommunications (DECT), Worldwide Interoperability for Microwave Access (WiMAX), wireless local area network (WLAN), Wi-Fi Protected Access I & II (WPA, WPA2), and integrated digital enhanced network (IDEN). Each of these technologies involves, for example, the transmission and reception of voice, data, signaling, and/or content messages. It should be understood that any references to terminology and/or technical details related to an individual telecommunication standard or technology are for illustrative purposes only, and are not intended to limit the scope of the claims to a particular communication system or technology unless specifically recited in the claim language.

Various embodiments illustrated and described are provided merely as examples to illustrate various features of the claims. However, features shown and described with respect to any given embodiment are not necessarily limited to the associated embodiment and may be used or combined with other embodiments that are shown and described. Further, the claims are not intended to be limited by any one example embodiment. For example, one or more of the operations of the methods may be substituted for or combined with one or more operations of the methods.

Implementation examples are described in the following paragraphs. While some of the following implementation examples are described in terms of example methods, further example implementations may include: the example methods discussed in the following paragraphs implemented by an FDS or CO detection system including a processor configured with processor-executable instructions to perform operations of the methods of the following implementation examples; the example methods discussed in the following paragraphs implemented by an FDS or CO detection system including means for performing functions of the methods of the following implementation examples; and the example methods discussed in the following paragraphs may be implemented as a non-transitory processor-readable storage medium having stored thereon processor-executable instructions configured to cause a processor of an FDS or CO detection system to perform the operations of the methods of the following implementation examples.

Example 1. A method for communicating a carbon monoxide (CO) detection to a communication network performed by a processor of a CO detection device, including receiving information from one or more CO sensors configured to detect CO; determining whether the information received from the one or more CO sensors satisfies one or more threshold criteria indicative of CO detection; generating a CO warning message including a CO alarm object in response to determining that the information received from the one or more CO sensors satisfies one or more threshold criteria indicative of CO detection; and sending the generated CO warning message to a remote server via a communication network.

Example 2. The method of example 1, in CO alarm object includes a Lightweight Machine-to-Machine (LwM2M) object.

Example 3. The method of either of examples 1 or 2, in which the CO alarm object is configured to indicate one or more resource definition identifiers (IDs).

Example 4. The method of any of examples 1-3, in which CO alarm object is configured to indicate a permissible operation for a resource of the CO alarm object.

Example 5. The method of any of examples 1-4, in which the CO alarm object is configured to indicate a permitted number of instances of a resource of the CO alarm object.

Example 6. The method of any of examples 1-5, in which the CO alarm object is configured to indicate whether an operation related to a resource of the CO alarm object is mandatory or optional.

Example 7. The method of any of examples 1-6, in which the CO alarm object is configured to indicate a data type of a resource of the CO alarm object.

Example 8. The method of any of examples 1-7, in which the CO alarm object is configured to indicate a permitted range for or enumeration of information of a resource of the CO alarm object.

Example 9. The method of any of examples 1-8, in which CO alarm object is configured to indicate permissible units for information represented in a resource of the CO alarm object.

Example 10. The method of any of examples 1-9, in which the CO alarm object is configured to include a description of one or more values associated with a resource of the CO alarm object.

Example 11. The method of any of examples 1-10, in which sending the generated CO warning message to a remote server via a communication network includes activating a transceiver; and sending the generated CO warning message to the remote server via the communication network using the activated transceiver.

Example 12. The method of any of examples 1-11, in which the communication network includes a wireless communication network.

Example 13. The method of any of examples 1-11, in which the communication network includes a wired communication network.

The foregoing method descriptions and the process flow diagrams are provided merely as illustrative examples and are not intended to require or imply that the operations of various embodiments must be performed in the order presented. As will be appreciated by one of skill in the art the order of operations in the foregoing embodiments may be performed in any order. Words such as "thereafter," "then," "next," etc. are not intended to limit the order of the operations; these words are used to guide the reader through the description of the methods. Further, any reference to claim elements in the singular, for example, using the articles "a," "an," or "the" is not to be construed as limiting the element to the singular.

Various illustrative logical blocks, modules, components, circuits, and algorithm operations described in connection with the embodiments disclosed herein may be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such embodiment decisions should not be interpreted as causing a departure from the scope of the claims.

The hardware used to implement various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of receiver smart objects, e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

In one or more embodiments, the functions described may be implemented in hardware, software, firmware, or any combination thereof. If implemented in software, the functions may be stored as one or more instructions or code on a non-transitory computer-readable storage medium or non-transitory processor-readable storage medium. The operations of a method or algorithm disclosed herein may be embodied in a processor-executable software module or processor-executable instructions, which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, FLASH memory, CD-ROM or other optical disk storage, magnetic disk storage or other magnetic storage smart objects, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer program product.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the present disclosure is not intended to be limited to the embodiments shown herein but is to be accorded the widest scope consistent with the following claims and the principles and novel features disclosed herein.

What is claimed is:

1. A method for communicating a carbon monoxide (CO) detection to a communication network performed by a processor of a CO detection device, comprising:
   receiving information from one or more CO sensors configured to detect CO;
   determining whether the information received from the one or more CO sensors satisfies one or more threshold criteria indicative of CO detection;
   generating a CO warning message comprising a CO alarm object in response to determining that the information received from the one or more CO sensors satisfies one or more threshold criteria indicative of CO detection, wherein the CO alarm object comprises a Lightweight Machine-to-Machine (LwM2M) object;
   sending the generated CO warning message to a remote server via a communication network.

2. The method of claim 1, wherein the CO alarm object is configured to indicate one or more resource definition identifiers (IDs).

3. The method of claim 1, wherein the CO alarm object is configured to indicate a permissible operation for a resource of the CO alarm object.

4. The method of claim 1, wherein the CO alarm object is configured to indicate a permitted number of instances of a resource of the CO alarm object.

5. The method of claim 1, wherein the CO alarm object is configured to indicate whether an operation related to a resource of the CO alarm object is mandatory or optional.

6. The method of claim 1, wherein the CO alarm object is configured to indicate a data type of a resource of the CO alarm object.

7. The method of claim 1, wherein the CO alarm object is configured to indicate a permitted range for or enumeration of information of a resource of the CO alarm object.

8. The method of claim 1, wherein the CO alarm object is configured to indicate permissible units for information represented in a resource of the CO alarm object.

9. The method of claim 1, wherein the CO alarm object is configured to include a description of one or more values associated with a resource of the CO alarm object.

10. The method of claim 1, wherein sending the generated CO warning message to a remote server via a communication network comprises:
activating a transceiver; and
sending the generated CO warning message to the remote server via the communication network using the activated transceiver.

11. A carbon monoxide (CO) detection device, comprising:
a processor configured with processor-executable instructions to:
receive information from one or more CO sensors configured to detect CO;
determine whether the information received from the one or more CO sensors satisfies one or more threshold criteria indicative of CO detection;
generate a CO warning message comprising a CO alarm object in response to determining that the information received from the one or more CO sensors satisfies one or more threshold criteria indicative of CO detection, wherein the CO alarm object comprises a Lightweight Machine-to-Machine (LwM2M) object;
send the generated CO warning message to a remote server via a communication network.

12. The CO detection device of claim 11, wherein the processor is further configured with processor-executable instructions such that the CO alarm object is configured to indicate one or more resource definition identifiers (IDs).

13. The CO detection device of claim 11, wherein the processor is further configured with processor-executable instructions such that the CO alarm object is configured to indicate a permissible operation for a resource of the CO alarm object.

14. The CO detection device of claim 11, wherein the processor is further configured with processor-executable instructions such that the CO alarm object is configured to indicate a permitted number of instances of a resource of the CO alarm object.

15. The CO detection device of claim 11, wherein the processor is further configured with processor-executable instructions such that the CO alarm object is configured to indicate whether an operation related to a resource of the CO alarm object is mandatory or optional.

16. The CO detection device of claim 11, wherein the processor is further configured with processor-executable instructions such that the CO alarm object is configured to indicate a data type of a resource of the CO alarm object.

17. The CO detection device of claim 11, wherein the processor is further configured with processor-executable instructions such that the CO alarm object is configured to indicate a permitted range for or enumeration of information of a resource of the CO alarm object.

18. The CO detection device of claim 11, wherein the processor is further configured with processor-executable instructions such that the CO alarm object is configured to indicate permissible units for information represented in a resource of the CO alarm object.

19. The CO detection device of claim 11, wherein the processor is further configured with processor-executable instructions such that the CO alarm object is configured to include a description of one or more values associated with a resource of the CO alarm object.

20. The CO detection device of claim 11, wherein the processor is further configured with processor-executable instructions to:
activate a transceiver; and
send the generated CO warning message to the remote server via the communication network using the activated transceiver.

21. A carbon monoxide (CO) detection device, comprising:
means for receiving information from one or more CO sensors configured to detect CO;
means for determining whether the information received from the one or more CO sensors satisfies one or more threshold criteria indicative of fire event or CO detection;
means for generating a CO warning message comprising a CO alarm object in response to determining that the information received from the one or more CO sensors satisfies one or more threshold criteria indicative of CO detection, wherein the CO alarm object comprises a Lightweight Machine-to-Machine (LwM2M) object;
means for sending the generated CO warning message to a remote server via a communication network.

22. The CO detection device of claim 21, wherein the CO alarm object is configured to indicate one or more resource definition identifiers (IDs).

23. The CO detection device of claim 21, wherein the CO alarm object is configured to indicate a permissible operation for a resource of the CO alarm object.

24. The CO detection device of claim 21, wherein the CO alarm object is configured to indicate a permitted number of instances of a resource of the CO alarm object.

25. The CO detection device of claim 21, wherein the CO alarm object is configured to indicate whether an operation related to a resource of the CO alarm object is mandatory or optional.

26. The CO detection device of claim 21, wherein the CO alarm object is configured to indicate a data type of a resource of the CO alarm object.

27. The CO detection device of claim 21, wherein the CO alarm object is configured to indicate a permitted range for or enumeration of information of a resource of the CO alarm object.

28. The CO detection device of claim 21, wherein the CO alarm object is configured to indicate permissible units for information represented in a resource of the CO alarm object.

29. The CO detection device of claim 21, wherein the CO alarm object is configured to include a description of one or more values associated with a resource of the CO alarm object.

30. The CO detection device of claim 21, further comprising:
means for activating a transceiver; and
means for sending the generated CO warning message to the remote server via the communication network using the activated transceiver.

31. A non-transitory processor-readable medium having stored thereon processor-executable instructions configured to cause a processing device in a carbon monoxide (CO) detection device to perform operations comprising:
receiving information from one or more CO sensors configured to detect CO;

determining whether the information received from the one or more CO sensors satisfies one or more threshold criteria indicative of CO detection;

generating a CO warning message comprising a CO alarm object in response to determining that the information received from the one or more CO sensors satisfies one or more threshold criteria indicative of CO detection, wherein the CO alarm object comprises a Lightweight Machine-to-Machine (LwM2M) object;

sending the generated CO warning message to a remote server via a communication network.

* * * * *